US010584175B2

(12) United States Patent
Casey

(10) Patent No.: US 10,584,175 B2
(45) Date of Patent: Mar. 10, 2020

(54) FN14-BINDING PROTEINS AND USES THEREOF

(71) Applicant: La Trobe University, Bundoora (AU)

(72) Inventor: Joanne Casey, Greensborough (AU)

(73) Assignee: La Trobe University, Bundoora (AU)

(*) Notice: Subject to any disclaimer, the term of this patent is extended or adjusted under 35 U.S.C. 154(b) by 83 days.

(21) Appl. No.: 15/520,836

(22) PCT Filed: Oct. 23, 2015

(86) PCT No.: PCT/AU2015/050658
§ 371 (c)(1),
(2) Date: Apr. 20, 2017

(87) PCT Pub. No.: WO2016/061632
PCT Pub. Date: Apr. 28, 2016

(65) Prior Publication Data
US 2017/0335004 A1 Nov. 23, 2017

(30) Foreign Application Priority Data
Oct. 23, 2014 (AU) ................................ 2014904235

(51) Int. Cl.
| A61K 39/395 | (2006.01) |
| C07K 16/28 | (2006.01) |
| C07K 16/30 | (2006.01) |
| C07K 19/00 | (2006.01) |
| A61K 39/00 | (2006.01) |

(52) U.S. Cl.
CPC ........ *C07K 16/2878* (2013.01); *A61K 39/395* (2013.01); *C07K 16/30* (2013.01); *C07K 19/00* (2013.01); *A61K 2039/505* (2013.01); *C07K 2317/21* (2013.01); *C07K 2317/55* (2013.01); *C07K 2317/92* (2013.01)

(58) Field of Classification Search
None
See application file for complete search history.

(56) References Cited

U.S. PATENT DOCUMENTS

| 4,196,265 A | 4/1980 | Koprowski et al. |
| 4,676,980 A | 6/1987 | Segal et al. |
| 4,816,567 A | 3/1989 | Cabilly et al. |
| 5,194,594 A | 3/1993 | Khawli et al. |
| 5,485,277 A | 1/1996 | Foster |
| 5,492,840 A | 2/1996 | Malmqvist et al. |
| 5,565,332 A | 10/1996 | Hoogenboom et al. |
| 5,567,301 A | 10/1996 | Stetter et al. |
| 5,731,168 A | 3/1998 | Carter et al. |
| 5,821,047 A | 10/1998 | Garrard et al. |
| 5,885,793 A | 3/1999 | Griffiths et al. |
| 6,190,908 B1 | 2/2001 | Kang |
| 6,248,516 B1 | 6/2001 | Winter et al. |
| 6,300,064 B1 | 10/2001 | Knappik et al. |
| 6,306,610 B1 | 10/2001 | Bawendi et al. |
| 6,737,056 B1 | 5/2004 | Presta |
| 7,022,500 B1 | 4/2006 | Queen et al. |
| 7,317,091 B2 | 1/2008 | Lazar et al. |
| 7,923,221 B1 | 4/2011 | Cabilly et al. |
| 2006/0228364 A1 | 10/2006 | Dennis et al. |
| 2006/0263367 A1 | 11/2006 | Fey et al. |
| 2008/0260757 A1 | 10/2008 | Holt et al. |

FOREIGN PATENT DOCUMENTS

| AU | 2014203658 A1 | 7/2014 | |
| EP | 0368684 A1 | 5/1990 | |
| EP | 0569141 A2 | 11/1993 | |
| WO | WO-90/05144 A1 | 5/1990 | |
| WO | WO-93/21232 A1 | 10/1993 | |
| WO | WO-94/04678 A1 | 3/1994 | |
| WO | WO-94/07921 A1 | 4/1994 | |
| WO | WO-94/09817 A1 | 5/1994 | |
| WO | WO-97/49805 A2 | 12/1997 | |
| WO | WO-98/44001 A1 | 10/1998 | |
| WO | WO-99/56126 A2 | 11/1999 | |
| WO | WO-99/57134 A1 | 11/1999 | |
| WO | WO-00/34317 A2 | 6/2000 | |
| WO | WO 2001/58956 | * 8/2001 | ......... A61K 39/3955 |
| WO | WO-02/26292 A1 | 4/2002 | |
| WO | WO-2002/066630 A1 | 8/2002 | |
| WO | WO-2003/086311 A2 | 10/2003 | |
| WO | WO-2004/058820 A2 | 7/2004 | |
| WO | WO-2004/064724 A2 | 8/2004 | |
| WO | WO-2004/108158 A1 | 12/2004 | |
| WO | WO-2005/118629 A1 | 12/2005 | |
| WO | WO-2008/129058 A1 | 10/2008 | |
| WO | WO-2008/142124 A1 | 11/2008 | |
| WO | WO-2009/020933 A2 | 2/2009 | |

(Continued)

OTHER PUBLICATIONS

Gefter, ML et al., A simple method for polyethylene glycol-promoted hybridization of mouse myeloma cells, Somatic Cell Genet, 3(2):231-6 (1977).
Al-Lazikani, B, et al., Standard conformations for the canonical structures of immunoglobulins, J Mol Biol, 273(4):927-48 (1997).
Bork, P., et al., The immunoglobulin fold. Structural classification, sequence patterns and common core, J Mol Biol, 242(4):309-20 (1994).
Brinkmann, U. et al., A recombinant immunotoxin containing a disulfide-stabilized Fv fragment, Proc Natl Acad Sci USA, 90(16):7538-42 (1993).
Chothia, C. and Lesk, Am., Canonical structures for the hypervariable regions of immunoglobulins, J Mol Biol, 196(4):901-17 (1987).
Chothia, C. et al., Conformations of immunoglobulin hypervariable regions, Nature, 342(6252):877-83 (1989).

(Continued)

Primary Examiner — Christine J Saoud
(74) Attorney, Agent, or Firm — Choate, Hall & Stewart LLP

(57) ABSTRACT

The present invention provides an isolated or recombinant Fn14-binding protein comprising an antigen binding domain, wherein the antigen binding domain binds specifically to Fn14 or a cell expressing Fn14.

10 Claims, 9 Drawing Sheets

Specification includes a Sequence Listing.

(56) References Cited

FOREIGN PATENT DOCUMENTS

| WO | WO-2009/140177 A2 | 11/2009 |
| WO | WO-2010/080538 A1 | 7/2010 |
| WO | WO-2011/097500 A2 | 8/2011 |
| WO | WO-2012/122513 A2 | 9/2012 |
| WO | WO-2013/026099 A1 | 2/2013 |
| WO | WO-2014/198817 A1 | 12/2014 |

OTHER PUBLICATIONS

Coia, G. et al., Construction of recombinant extended single-chain antibody peptide conjugates for use in the diagnosis of HIV-1 and HIV-2, J Immunol Methods, 192(1-2):13-23 (1996).
De Haard, H. et al., A Large Non-immunized Human Fab Fragment Phage Library That Permits Rapid Isolation and Kinetic Analysis of High Affinity Antibodies, The Journal of Biological Chemistry, 274(26):18218-18230 (1999).
De Kruif, J. and Logtenberg, T., Leucine Zipper Dimerized Bivalent and Bispecific scFv Antibodies from a Semi-synthetic Antibody Phage Display Library, The Journal of Biological Chemistry, 271(13):7630-7634 (1996).
Dharmapatni, AA., TWEAK and Fn14 expression in the pathogenesis of joint inflammation and bone erosion in rheumatoid arthritis, Arthritis Res Ther, 13(2):R51 (2011).
Frauenknecht, K. et al., Neuroprotective effect of Fn14 deficiency is associated with induction of the granulocyte-colony stimulating factor (G-CSF) pathway in experimental stroke and enhanced by a pathogenic human antiphospholipid antibody, J Neuroimmunol, 227(1-2):1-9 (2010).
Giudicelli, V. et al., IMGT, the international ImMunoGeneTics database, Nucleic Acids Res, 25(1):206-11 (1997).
Guan, L. et al., Homogeneous immunoconjugates for boron neutron-capture therapy: design, synthesis, and preliminary characterization, Proc Natl Acad Sci USA, 95(22):13206-10 (1998).
Honegger, A. and Plückthun, A., Yet another numbering scheme for immunoglobulin variable domains: an automatic modeling and analysis tool, J Mol Biol, 309(3):657-70 (2001).
Inta, I. et al., Induction of the cytokine TWEAK and its receptor Fn14 in ischemic stroke, Journal of the Neurological Sciences, 275:117-120 (2008).
International Search Report for PCT/AU2015/050658, 8 pages (dated Dec. 10, 2015).
Johnston, A.J. et al., Targeting of Fn14 Prevents Cancer-Induced Cachexia and Prolongs Survival, Cell, 162:1365-1378 (2015).
Kumar, A., bcl2 and v-abl oncogenes cooperate to immortalize murine B cells that secrete antigen specific antibodies, Immunol Lett, 65(3):153-9 (1999).
Köhler, G. and Milstein, C., Derivation of specific antibody-producing tissue culture and tumor lines by cell fusion, Eur J Immunol, 6(7):511-519 (1976).
Köhler, G., and Milstein, C., Continuous cultures of fused cells secreting antibody of predefined specificity, Nature, 256(5517):495-7 (1975).
Marks, J.D. et al., By-passing immunization: building high affinity human antibodies by chain shuffling, Biotechnology (NY), 10(7):779-83 (1992).
Natsume, A. et al., Engineered antibodies of IgG1/IgG3 mixed isotype with enhanced cytotoxic activities, Cancer Res, 68(10):3863-72 (2008).
Padlan, E. et al., Identification of specificity-determining residues in antibodies, The FASEB Journal, 9:133-139 (1995).
Sakaguchi, N. et al., Altered thymic T-cell selection due to a mutation of the ZAP-70 gene causes autoimmune arthritis in mice, Nature, 426(6965):454-60 (2003).
Shalaby, MR. et al., Development of humanized bispecific antibodies reactive with cytotoxic lymphocytes and tumor cells overexpressing the HER2 protooncogene, J Exp Med, 175(1):217-25 (1992).
Trenado, A., et al., Recipient-type specific CD4+CD25+ regulatory T cells favor immune reconstitution and control graft-versus-host disease while maintaining graft-versus-leukemia, J Clin Invest, 112(11):1688-96 (2003).
Vince, JE. et al., TWEAK-FN14 signaling induces lysosomal degradation of a cIAP1-TRAF2 complex to sensitize tumor cells to TNFalpha, J Cell Biol, 182(1):171-84 (2008).
Written Opinion for PCT/AU2015/050658, 5 pages (dated Dec. 10, 2015).
Yamane-Ohnuki, N. et al., Establishment of FUT8 knockout Chinese hamster ovary cells: an ideal host cell line for producing completely defucosylated antibodies with enhanced antibody-dependent cellular cytotoxicity, Biotechnol Bioeng, 87(5):614-22 (2004).
Zhao, Z. et al., TWEAK/Fn14 interactions are instrumental in the pathogenesis of nephritis in the chronic graft-versus-host model of systemic lupus erythematosus, J Immunol, 179(11):7949-58 (2007).
Culp, P. et al., Antibodies to TWEAK Receptor Inhibit Human Tumor Growth through Dual Mechanisms, Clinical Cancer Research, 16(2):497-508 (2010).
Drescher, Dr. Anja, Characterization of biological interactions with Biacore, Internet Citation, pp. 1-26 (2011).
Extended European Search Report for EP15853070.9, 13 pages (dated May 4, 2018).
Jackson, J. et al., In Vitro Antibody Maturation Improvement of a High Affinity, Neutralizing Antibody Against IL-1 beta, The Journal of Immunology, 154:3310-3319 (1995).
No Author Listed, Dissociation constant—Wikipedia, the free encyclopedia, (Jun. 27, 2016), Retrieved from the Internet: URL:https://en.wikipedia.org/wiki/Dissociation_constant [retrieved on Jul. 13, 2016].
Rudikoff, S. et al., Single Amino Acid Substitution Altering Antigen-Binding Specificity, PNAS, 79:1979-1983 (1982).
Salzmann, S. et al., Fibroblast Growth Factor Inducible (Fn14)-specific Antibodies Concomitantly Display Signaling Pathway-specific Agonistic and Antagonistic Activity, Journal of Biological Chemistry, 288(19):13455-13466 (2013).
Wong, Y. W. et al., Structural Requirements for a Specificity Switch and for Maintenance of Affinity Using Mutational Analysis of a Phage-Displayed Anti-Arsonate Antibody of Fab Heavy Chain First Complementarity-Determining Region, The Journal of Immuno, 160:5990-5997 (1998).
International Preliminary Report on Patentabilty for PCT/AU2015/050568, 6 pages (dated Apr. 25, 2017).

* cited by examiner

| | FR1 | CDR1 | FR2 | CDR2 | FR3 | CDR3 | FR4 |
|---|---|---|---|---|---|---|---|
| m001 | QVQLQQSGGGLVQPGGSMKLSCIASGFTFS | SYWMS | WVRQSPEKGLEWVA | EIRSKSDNYATHYAESVKG | KFTISRDDSKSRFFLQMNNLRAEDTGIYYCSS | TYADYFHY | WGQGTDLVTVSS |
| m002 | EVKLQQSGGGLVQPGGSMKLSCVASGFTFS | YYWMN | WVRQSPEQGLEWIA | EIRLQSNDYPTHYAESVKG | RFTISRDDSKNSVYLQMNNLRPEDTGIYYCAC | RYADYFDH | WGQGTTLTVSS |
| m005 | QVQLQESGGGLVQPGGSMKLSCVASGFTFS | YYWMN | WVRQSPEQGLEWIA | EIRLQSNDYPTHYAESVKG | RFTISRDDSKNSVYLQMNNLRPEDTGIYYCAC | RYADYFDH | WGQGTTLFVSS |
| m006 | QVQLQESGGGLVQPGGSMKLSCVASGFTFS | YYWMN | WVRQSPEKGLEWVS | EIRLQSNDYPTHYAESVKG | RFTISRDDSKNSVYLQMNNLRPEDTGIYYCAC | RYADYFDH | WGQGTTLTVSS |
| m007 | QVKLEESGGGLVQPGGSMKLSCIASGFSFS | KYWMN | WVRQSPEKGLEWVA | EIRVKSNNYATHYAESVKG | RFTISRDDSKSSVYLQMNNLRAEDTGIYYCTK | SYADYFDY | WGQGTTLTVSS |
| m003 | QVKLEQSGGGLVQPGGSMKLSCVASGFTFS | HYWMS | WVRQSPEKGLEWVA | EIRLKSDNYATHYAESVKG | RFTISRDDSKSRLYLQMSSLRAEDTGIYYCTG | RYSDYFDY | WGQGTTLTVSS |
| m004 | QVQLQQSGGGLVQPGGSMKLSCVASGFTFS | HYWMS | WVRQSPEKGLEWVA | EIRLKSDNYATHYAESVKG | KFTISRDDSKSRLYLQMSSLRAEDTGIYYCTG | RYSDYFDY | WGQGTTLFVSS |
| hPDL192 | EVQLVESGGGLVQPGGSLRLSCAASGFTFS | SYWMS | WVRQAPGKGLEWVA | EIRLKSDNYATHYAESVKG | RFTISRDDSKNSLYLQMNSLRAEDTAVYYCTG | YYADAMDY | WGQGTLVTVSS |
| hPDL19.2.1 | EVKLEESGGGLVQPGGSMKLSCVASGFTFS | SYWMS | WVRQSPEKGLEWVA | EIRLKSDNYATHYAESVKG | KFTISRDDSKSRLYLQMSLRAEDTGIYYCTG | YYADAMDY | WGQGTSVTVSS |
| Biogen09 | QVQLQQSGPEVVRPGGVSVKISCKGSGYFTDYGMH | | WVKQSHARSLEWIG | VISTYNG-Y-TNYNQKFKG | KATMTVDKSSTAYMELARLTSEDSAIYYCAR | AYYGNLYYAMDY | WGQGTSVTVSS |
| hFab 6.5 | QVQLVQSGGGLVKPGGSLRLSCAASGFTFT | SYAMS | WVRQAPGKGLEWVS | AISGSGGGSTYYAD | SVKG RFTISRDNPKNTLYLQMNSLRAEDTAVYYCAR | VRANYYYGMDV | WGQGTLVTVSS |
| hFab 6.11 | QVQLVESGGGLVQPGGSLRLSCAASGFTFS | SYAMS | WVRQAPGKGLEWVS | AISGGGGGSTYYAD | SVKG RFTISRDKSKNTLYLQMNSLRAEDTAVYYCAK | AENDFWSGYHQV | WGQGTLVTVSS |
| hFab 5.4 | EVQLVESGGGLVQPGGSLRLSCAASGFTFS | SYAMS | WVRQAPGKGLEWVS | AISGSGGSTYYAD | SVKG RFTISRDNSKNTLYLQMNSLRAEDTAVYYCAK | DVSGGDYAAGYFDG | WGMGTTVTAST |
| hFab 5.5 | QVQLVQSGGGLVKPGGSLRLSCAASGFTFS | SYAMS | WVRQAPGKGLEWVS | AISGSGGSTYYAD | SVKG RFTISRDNSKNTLYLQMNSLRAEDTAVYYCAK | DAGYYYGMDV | WGQGTVTVSS |
| hFab 5.6 | EVQLVESGGGLVQPGGSLRLSCAASGFTFS | SYAMS | WVRQAPGKGLEWVS | AISGSGGGSTYYAD | SVKG RFTISRDNSKNTLYLQMNSLRAEDTAVYYCAK | AGYSSGYGAFDI | WGQGTMVTVSS |
| hFab 5.7 | EVQLVESGGGLVQPGGSLRLSCAASGFTFS | SYAMS | WVRQAPGKGKGLE-VS | AISGSGGGSTYYAD | SVKG RFTISRDNSKNTLYLQMNSLRAEDTAVYYCAK | DKNYYDSSGYSPDAFDI | WGQGTMVTVSS |
| hFab 5.8 | EVQLVESGGGLVQPGGSLRLSCAASGFTFS | NYAMH | WVRQAPGKGLEYVS | AITGSGGNYYAD | SVKG RFTISRDNAKNSLYLQMNSLRDEDTAVYYCAR | EVDGRAGMFMDV | WGQGTVVTVSS |
| hFab 5.9 | EVQLVESGGGLVQPRGGSLRLSCAASGFTFS | RYAMS | WVRQAPGKGLEWVS | AISGSGGGSTYYAD | SVKG RFTISRDNSKNTLYLQMNSLRAEDTAVYYCAK | GLGSSRSLGAFDI | WGQGTMVTVSS |
| hFab 5.10 | EVQLVQSGRGLVKPGGSLRLSCAASGFTFS | SYAMS | WVRQAPGKGLEWVS | AISGSGGGSTYYAD | SVKG RFTISRDNSKNTLYLQMNSLRAEDTAVYYCAK | ARNFGAFDI | WGQGTLVTVSS |
| hFab 5.15 | QVQLVESGGGLVQPGGSLRLSCAASGFTFS | SYAMS | WVRQAPGKGLEWVS | AISGSGGGSTYYAD | SVKG RFTISRDKSKNTLYLQMNSLRAEDTAVYYCAK | AENDFWSGYHQV | WGRGTLVTVST |
| hFab 5.17 | QVQLVESGGGLVQPGGSLRLSCAASGFTFS | SYAMS | WVRQAPGKGLEWVS | AISGSGGGSTYYAD | SVKG RFTISRDNSKNTLYLQMNSLRAEDTAVYYCAK | DENDFWSGYHHG | WGQGTTVTVSS |
| hFab 5.18 | EVQLVESGGGLVQPGGSLRLSCAASGFTFS | SYAMS | WVRQAPGKGLEWVS | AISGSGGGSTYYAD | SVKG RFTISRDNSKNTLYLQMNSLRAEDTAVYYCAR | DYNDYDYGYAFDV | WGQGTFVTVSS |
| hFab 5.22 | EVQLVQSGGGLVQPGGSLRLSCAASGFTFS | SYGMN | WVRQAPGKGLEWVS | AISGSGGSTYYAD | SVKG RFTISRDNSKNTLYLQMNSLRAEDTAVYYCAR | GGPFSPNIGRTFDS | WGLGTLVSVSA |
| hFab 5.23 | EVQLVQSGGGLVQPGGSLRLSCAASGFTFS | SYAMN | WVRQAPGKGLEWVS | AISGSGGGSTYYAD | SVKG RFTISRDNSKNTLYLQMNSLRAEDTAVYYCAK | DKNYYDGSDYSADAFDI | WGQGTMVTVSS |
| hFab 5.24 | EVQLVESGGGLVQPGGSLRLSCAASGFTFS | SYAMN | WVRQAPGKGLEWVS | AISGNGGSGGSTYYAD | SVKG RFTISRDNSKNTLYLQMNSLRAEDTAVYYCAR | GIYYIDGHGYFAPDA | WGQGTVVTVSS |

FIGURE 2

| | FR1 | CDR1 | FR2 | CDR2 | FR3 | CDR3 | FR4 |
|---|---|---|---|---|---|---|---|
| m001 | DIVMTQTPASLAVSLGQRATISC | RASQSVSTSTYSYMH | WYQQKPGQPPKLLIK | YASSLES | GVPARFSGSGSGTDFTLNIHPVEEEDTATYYC | QHSWEIPYT | FGGGTKLEIKR |
| m002 | DTVLTQSPASLVVSLGQRATISC | RASQSVSTSDYSIH | WYQQKPGQPPKFLIK | YASNRDS | GVPARFSGSGSGTDFTLNIHPVEEEDTAIYYC | QHSWEIPPT | FGAGTKLELQR |
| m005 | DIVLTQTTASLTVSLGQRATISC | RASQSVSTSTYSYMH | WYQQTPGQPPTVLIK | YASSLES | GVPTRFSGSGSGTDFTLNIHPVEEEDTATYYC | QHSWEIPYT | FGGGTKLEIKR |
| m006 | DIVITQSPASLVSLGQRATISC | RASQSVSTSTYSYMH | WYQQTPGQPPTVLIK | YASSLES | GVPTRFSGSGSGTDFTLNIHPVEEEDTATYYC | QHSWEIPYT | FGGGTKLEIKR |
| m007 | DIVMTQSTASLAVSLGQRATISC | RASQSVSTSSYSYMH | WYQQKPGQPPKVLIK | YASNLES | GVPARFSGSGSGTDFTLNIHPVEEEDAATYYC | QHSWEIPYT | FGGGTKLEIKR |
| hPDL192 | DRVTITC | RASQSVSTSSYSYMH | WYQQKPGKAPKLLIK | YASNLES | GVPSRFSGSGSGTDFTLTISSLQPEDFATYYC | QHSWEIPYT | FGGGTKVEIKR |
| hPDL19.2.1 | QRATISC | RASQSVSTSSYSYMH | WYQQKPGQPPKLLIK | YASNLES | GVPARFSGSGSGTDFTLNIHPVEEEDTATYYC | QHSWEIPYT | FGGGTKLEIKR |
| Biogen09 | DIVLTQSPASLAVSLGQRATISC | RASKSVSTSSYSYMH | WYQQKPGQPPKLLIK | YASNLES | GVPARFSGSGSGTDFTLNIHPVEEEDAATYYC | QHSRELPFT | FGSGTKLEIKR |
| hFab 6.5 | LTQSPGTLSLSPGERATLSC | RASQSVSSSTLA | WYQQKPGQTPRLLIY | GASTRAT | GIPARFSGSGSGTDFTLTISRLEPEDFAVYYC | QQYGSSRLT | FGGGTKVEIKR |
| hFab 6.11 | LTQSPATLSVSPGERATLSC | RASQSVSSSNLA | WYQQKPGQAPRLLIY | GASTRAT | GIPARFSGSGSGTDFTLTISRLEPEDFAVYYC | QQYGSSRLT | FGGGTKVEIKR |
| hFab 5.4 | LTHPSPVSGAPMQRVTISC | TGSTSHIGARIDVH | WYQQLPGTAPKLLIY | GNTMRPS | GVPDRFSGSKSGTSSSLAITGLQAEDEADYYC | QSYDSSLSGSWV | FGGGTKLTVLG |
| hFab 5.5 | MTQSPGTLSLSPGERATLSC | RASQNVTNSYVG | WYQKKPGQAPMLLIY | GASRRAA | GIPDRFSGSGSGTDFTLTISRLEAEDFAVYYC | QQYGSSPLT | FGGGTKVEIKR |
| hFab 5.7 | LTQSPATLSVSPGERVTLSC | RASQSINRNLA | WYQQKPGQAPRLLIY | GASTRAT | GIPARFSGSGSGTDFTLTINRLEPENFAVYYC | QQYGGSSFT | FGPGTKVDIKR |
| hFab 5.9 | MTQSPGTLSLSPGERATLSC | RASQSVSSTYLS | WYQQKPGQAPRLLIY | GASSRAT | GTPDRFSGSGSGKYFTLTISRLEPEDFAVYYC | QHYGSSPYT | FGQGTKLEIKR |
| hFab 5.1 | LTQSPGTLSLSPGERATLSC | GASQSVSNSYLA | WYQQKPGLAPRLLIY | GASSRAT | GIPDRFSGSGSGTDFTLTISRLEPEDFAVYYC | QQYGSSPLT | FGPGTKVEIKR |
| hFab 5.2 | LTQPSSVSGAPGQRVTISC | TGSSSNIGARIDVH | WYQQLPGTAPKLLIY | GNSNRPS | GVPDRFSGSKSGTSASLAITGLQAEDEADYYC | QSYDSSLSGSWV | FGGGTKLTVLG |
| hFab 5.3 | LTQSPGTLSLSPGERATLSC | RASQSVSSSYLA | WYQQKPGQAPRLLIY | GASSRAT | GTPDRFSGSGSGTDFTLTISRLEPEDFAVYYC | QQYGSSPYT | FGQGTKLEIKR |
| hFab 5.6 | LTQSPLSLPVTLGQPASISC | RSRQSLIVYSDGNTYFNW | FHQRPGQSPRRLIY | RVSNRDS | GVPDRFSGSGSGTDFTLTISRVEAEDVGLYYC | MQGSHWPPT | FGQGTKLEIKR |
| hFab 5.12 | LTQPSSVSGTPGQRVTISC | SGGSSNIGRNTVD | WYQQFPGTAPKLLIY | TNNQRPS | GVPDRFPGSKSGTSASLAISGLQSADEADYYC | ATWDDNLNGAV | FGGGTQVTVLG |
| hFab5.13 | LTQSPGTLSLSPGERATLSC | RASQSVNRNDLA | WYQQKPGQAPRLLIY | AASTRAT | GIPDRFSASGSGTDFTLTISRLEPEDFAMYYC | QHYGSSLFT | FGPGTKVDIKR |

SEQUENCE LISTING

<160> NUMBER OF SEQ ID NOS: 82

<210> SEQ ID NO 1
<211> LENGTH: 102
<212> TYPE: PRT
<213> ORGANISM: Homo sapiens

<400> SEQUENCE: 1

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu Leu Trp Pro Ile Leu Gly Gly Ala Leu Ser Leu Thr Phe Val
    50                  55                  60

Leu Gly Leu Leu Ser Gly Phe Leu Val Trp Arg Arg Cys Arg Arg Arg
65                  70                  75                  80

Glu Lys Phe Thr Thr Pro Ile Glu Glu Thr Gly Gly Glu Gly Cys Pro
                85                  90                  95

Ala Val Ala Leu Ile Gln
            100

<210> SEQ ID NO 2
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: X
<222> LOCATION: (1)..(1)
<223> OTHER INFORMATION: S or N or R
<220> FEATURE:
<221> NAME/KEY: X
<222> LOCATION: (2)..(2)
<223> OTHER INFORMATION: Y or G
<220> FEATURE:
<221> NAME/KEY: X
<222> LOCATION: (5)..(5)
<223> OTHER INFORMATION: S or H or N

<400> SEQUENCE: 2

Xaa Xaa Ala Met Xaa
1               5

<210> SEQ ID NO 3
<211> LENGTH: 17
<212> TYPE: PRT
<213> ORGANISM: Artificial Sequence
<220> FEATURE:
<223> OTHER INFORMATION: synthetic
<220> FEATURE:
<221> NAME/KEY: X
<222> LOCATION: (3)..(3)
<223> OTHER INFORMATION: S or T
<220> FEATURE:
<221> NAME/KEY: X
<222> LOCATION: (5)..(5)
<223> OTHER INFORMATION: S or G or N
<220> FEATURE:
<221> NAME/KEY: X
<222> LOCATION: (8)..(8)
<223> OTHER INFORMATION: S or N

<400> SEQUENCE: 3

Ala Ile Xaa Gly Xaa Gly Gly Xaa Thr Tyr Tyr Ala Asp Ser Val Lys
1               5                   10                  15

Gly

<210> SEQ ID NO 4
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: X
<222> LOCATION: (1)..(1)
<223> OTHER INFORMATION: R or G
<220> FEATURE:
<221> NAME/KEY: X
<222> LOCATION: (3)..(3)
<223> OTHER INFORMATION: S or R
<220> FEATURE:
<221> NAME/KEY: X
<222> LOCATION: (4)..(4)
<223> OTHER INFORMATION: Q or P or R
<220> FEATURE:
<221> NAME/KEY: X
<222> LOCATION: (5)..(5)
<223> OTHER INFORMATION: S or N
<220> FEATURE:

```
<221> NAME/KEY: X
<222> LOCATION: (6)..(6)
<223> OTHER INFORMATION: V or I or L
<220> FEATURE:
<221> NAME/KEY: X
<222> LOCATION: (7)..(7)
<223> OTHER INFORMATION: S or T or N or G
<220> FEATURE:
<221> NAME/KEY: X
<222> LOCATION: (8)..(8)
<223> OTHER INFORMATION: S or R or N
<220> FEATURE:
<221> NAME/KEY: X
<222> LOCATION: (9)..(9)
<223> OTHER INFORMATION: S or R or T or N
<220> FEATURE:
<221> NAME/KEY: X
<222> LOCATION: (10)..(10)
<223> OTHER INFORMATION: T or N or S or Y or L or absent
<220> FEATURE:
<221> NAME/KEY: X
<222> LOCATION: (11)..(11)
<223> OTHER INFORMATION: L or V
<220> FEATURE:
<221> NAME/KEY: X
<222> LOCATION: (12)..(12)
<223> OTHER INFORMATION: A or S or G

<400> SEQUENCE: 4

Xaa Ala Xaa Xaa Xaa Xaa Xaa Xaa Xaa Xaa Xaa Xaa
1               5                   10

<210> SEQ ID NO 5
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: X
<222> LOCATION: (5)..(5)
<223> OTHER INFORMATION: S or T
<220> FEATURE:
<221> NAME/KEY: X
<222> LOCATION: (8)..(8)
<223> OTHER INFORMATION: R or A or S
<220> FEATURE:
<221> NAME/KEY: X
<222> LOCATION: (9)..(9)
<223> OTHER INFORMATION: L or N
<220> FEATURE:
<221> NAME/KEY: X
<222> LOCATION: (10)..(10)
<223> OTHER INFORMATION: A or L
<220> FEATURE:
<221> NAME/KEY: X
<222> LOCATION: (11)..(11)
<223> OTHER INFORMATION: A or absent

<400> SEQUENCE: 5

Arg Ala Ser Gln Xaa Val Ser Xaa Xaa Xaa Xaa
1               5                   10

<210> SEQ ID NO 6
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: X
<222> LOCATION: (1)..(1)
<223> OTHER INFORMATION: G or A
<220> FEATURE:
<221> NAME/KEY: X
```

```
<222> LOCATION: (2)..(2)
<223> OTHER INFORMATION: A or T
<220> FEATURE:
<221> NAME/KEY: X
<222> LOCATION: (4)..(4)
<223> OTHER INFORMATION: T or R or S or N
<220> FEATURE:
<221> NAME/KEY: X
<222> LOCATION: (7)..(7)
<223> OTHER INFORMATION: T or A

<400> SEQUENCE: 6

Xaa Xaa Ser Xaa Arg Ala Xaa
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: X
<222> LOCATION: (2)..(2)
<223> OTHER INFORMATION: Q or H
<220> FEATURE:
<221> NAME/KEY: X
<222> LOCATION: (3)..(3)
<223> OTHER INFORMATION: Y or F
<220> FEATURE:
<221> NAME/KEY: X
<222> LOCATION: (4)..(4)
<223> OTHER INFORMATION: G or R
<220> FEATURE:
<221> NAME/KEY: X
<222> LOCATION: (5)..(5)
<223> OTHER INFORMATION: S or G or N
<220> FEATURE:
<221> NAME/KEY: X
<222> LOCATION: (7)..(7)
<223> OTHER INFORMATION: R or P or S or L or P
<220> FEATURE:
<221> NAME/KEY: X
<222> LOCATION: (8)..(8)
<223> OTHER INFORMATION: L or F or Y or F or E
<220> FEATURE:
<221> NAME/KEY: X
<222> LOCATION: (9)..(9)
<223> OTHER INFORMATION: T

<400> SEQUENCE: 7

Gln Xaa Xaa Xaa Xaa Ser Xaa Xaa Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: synthetic

<400> SEQUENCE: 8

Gln Gln Phe Arg Asn Ser Leu Leu Thr
1               5

<210> SEQ ID NO 9
<211> LENGTH: 120
<212> TYPE: PRT
<213> ORGANISM: Artificial Sequence
<220> FEATURE:
<223> OTHER INFORMATION: synthetic

<400> SEQUENCE: 9
```

```
Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Ala Asn Tyr Tyr Tyr Gly Met Asp Val Trp Gly Gln
            100                 105                 110

Gly Thr Leu Val Thr Val Ser Ser
            115                 120

<210> SEQ ID NO 10
<211> LENGTH: 121
<212> TYPE: PRT
<213> ORGANISM: Artificial Sequence
<220> FEATURE:
<223> OTHER INFORMATION: synthetic

<400> SEQUENCE: 10

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Gly Ser Thr Tyr Tyr Ala Asp Ser Val
    50                  55                  60

Lys Gly Arg Phe Thr Ile Ser Arg Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Glu Asn Asp Phe Trp Ser Gly Tyr His Gly Val Trp Gly
            100                 105                 110

Gln Gly Thr Leu Val Thr Val Ser Ser
            115                 120

<210> SEQ ID NO 11
<211> LENGTH: 123
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Val Ser Gly Asp Tyr Ala Ala Gly Tyr Phe Asp Gly
             100                 105                 110

Trp Gly Met Gly Thr Thr Val Thr Ala Ser Thr
         115                 120
```

<210> SEQ ID NO 12
<211> LENGTH: 120
<212> TYPE: PRT
<213> ORGANISM: Artificial Sequence
<220> FEATURE:
<223> OTHER INFORMATION: synthetic

<400> SEQUENCE: 12

```
Gln Val Gln Leu Val Gln Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Gly Tyr Tyr Tyr Gly Met Asp Val Trp Gly Gln
             100                 105                 110

Gly Thr Thr Val Thr Val Ser Ser
         115                 120
```

<210> SEQ ID NO 13
<211> LENGTH: 121
<212> TYPE: PRT
<213> ORGANISM: Artificial Sequence
<220> FEATURE:
<223> OTHER INFORMATION: synthetic

<400> SEQUENCE: 13

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Gly Tyr Ser Ser Gly Tyr Gly Ala Phe Asp Ile Trp Gly
             100                 105                 110
```

```
Gln Gly Thr Met Val Thr Val Ser Ser
        115                 120
```

<210> SEQ ID NO 14
<211> LENGTH: 125
<212> TYPE: PRT
<213> ORGANISM: Artificial Sequence
<220> FEATURE:
<223> OTHER INFORMATION: synthetic

<400> SEQUENCE: 14

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Val Ser
        35                  40                  45

Ala Ile Ser Gly Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Lys Asn Tyr Tyr Asp Ser Ser Gly Tyr Ser Pro Asp Ala Phe
            100                 105                 110

Asp Ile Trp Gly Gln Gly Thr Met Val Thr Val Ser Ser
        115                 120                 125
```

<210> SEQ ID NO 15
<211> LENGTH: 121
<212> TYPE: PRT
<213> ORGANISM: Artificial Sequence
<220> FEATURE:
<223> OTHER INFORMATION: synthetic

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Tyr Val
        35                  40                  45

Ser Ala Ile Thr Gly Ser Gly Gly Asn Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Val Asp Gly Arg Ala Gly Met Phe Met Asp Val Trp Gly
            100                 105                 110

Gln Gly Thr Thr Val Thr Val Ser Ser
        115                 120
```

<210> SEQ ID NO 16
<211> LENGTH: 122
<212> TYPE: PRT
<213> ORGANISM: Artificial Sequence
<220> FEATURE:
<223> OTHER INFORMATION: synthetic

```
<400> SEQUENCE: 16

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Phe Ser Arg Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Gly Ser Ser Arg Ser Leu Gly Ala Phe Asp Ile Trp
            100                 105                 110

Gly Gln Gly Thr Met Val Thr Val Ser Ser
            115                 120

<210> SEQ ID NO 17
<211> LENGTH: 118
<212> TYPE: PRT
<213> ORGANISM: Artificial Sequence
<220> FEATURE:
<223> OTHER INFORMATION: synthetic

<400> SEQUENCE: 17

Glu Val Gln Leu Val Gln Ser Gly Arg Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Asn Phe Gly Ala Phe Asp Ile Trp Gly Gln Gly Thr
            100                 105                 110

Thr Val Thr Val Ser Ser
        115

<210> SEQ ID NO 18
<211> LENGTH: 121
<212> TYPE: PRT
<213> ORGANISM: Artificial Sequence
<220> FEATURE:
<223> OTHER INFORMATION: synthetic

<400> SEQUENCE: 18

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ser Ala Ile Ser Gly Gly Gly Ser Thr Tyr Tyr Ala Asp Ser Val
    50                  55                  60

Lys Gly Arg Phe Thr Ile Ser Arg Asp Lys Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Glu Asn Asp Phe Trp Ser Gly Tyr His Gln Val Trp Gly
            100                 105                 110

Gln Gly Thr Leu Val Thr Val Ser Ser
            115                 120

<210> SEQ ID NO 19
<211> LENGTH: 121
<212> TYPE: PRT
<213> ORGANISM: Artificial Sequence
<220> FEATURE:
<223> OTHER INFORMATION: synthetic

<400> SEQUENCE: 19

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Glu Asn Asp Phe Trp Ser Gly Tyr His His Gly Trp Gly
            100                 105                 110

Arg Gly Thr Leu Val Thr Val Ser Thr
            115                 120

<210> SEQ ID NO 20
<211> LENGTH: 124
<212> TYPE: PRT
<213> ORGANISM: Artificial Sequence
<220> FEATURE:
<223> OTHER INFORMATION: synthetic

<400> SEQUENCE: 20

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Asn Asp Tyr Tyr Asp Tyr Tyr Gly Tyr Ala Phe Asp
            100                 105                 110

-continued

Val Trp Gly Gln Gly Thr Thr Val Thr Val Ser Ser
        115                 120

<210> SEQ ID NO 21
<211> LENGTH: 123
<212> TYPE: PRT
<213> ORGANISM: Artificial Sequence
<220> FEATURE:
<223> OTHER INFORMATION: synthetic

<400> SEQUENCE: 21

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Phe Ser Pro Asn Ile Arg Thr Phe Asp Ser
            100                 105                 110

Trp Gly Leu Gly Thr Leu Val Ser Val Ser Ala
        115                 120

<210> SEQ ID NO 22
<211> LENGTH: 126
<212> TYPE: PRT
<213> ORGANISM: Artificial Sequence
<220> FEATURE:
<223> OTHER INFORMATION: synthetic

<400> SEQUENCE: 22

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Lys Asn Tyr Tyr Asp Gly Ser Asp Tyr Ser Ala Asp Ala
            100                 105                 110

Phe Asp Ile Trp Gly Gln Gly Thr Met Val Thr Val Ser Ser
        115                 120                 125

<210> SEQ ID NO 23
<211> LENGTH: 124
<212> TYPE: PRT
<213> ORGANISM: Artificial Sequence
<220> FEATURE:
<223> OTHER INFORMATION: synthetic

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ile Tyr Tyr Ile Asp Gly His Gly Tyr Phe Ala Phe Asp
            100                 105                 110

Ala Trp Gly Gln Gly Thr Val Val Thr Val Ser Ser
            115                 120

<210> SEQ ID NO 24
<211> LENGTH: 106
<212> TYPE: PRT
<213> ORGANISM: Artificial Sequence
<220> FEATURE:
<223> OTHER INFORMATION: synthetic

<400> SEQUENCE: 24

Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Ser Thr Leu Ala
            20                  25                  30

Trp Tyr Gln Gln Lys Pro Gly Gln Thr Pro Arg Leu Leu Ile Tyr Gly
        35                  40                  45

Ala Ser Thr Arg Ala Thr Gly Ile Pro Ala Arg Phe Ser Gly Ser Gly
    50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Arg Leu Thr Phe
                85                  90                  95

Gly Gly Gly Thr Lys Val Glu Ile Lys Arg
            100                 105

<210> SEQ ID NO 25
<211> LENGTH: 105
<212> TYPE: PRT
<213> ORGANISM: Artificial Sequence
<220> FEATURE:
<223> OTHER INFORMATION: synthetic

<400> SEQUENCE: 25

Leu Thr Gln Ser Pro Ala Thr Leu Ser Val Ser Pro Gly Glu Arg Ala
1               5                   10                  15

Thr Leu Ser Cys Arg Ala Ser Gln Ser Val Ser Ser Asn Leu Ala Trp
            20                  25                  30

Tyr Gln Gln Lys Pro Gly Gln Ala Pro Arg Leu Leu Ile Tyr Gly Ala
        35                  40                  45

Ser Thr Arg Ala Thr Gly Ile Pro Ala Arg Phe Ser Gly Ser Gly Ser
    50                  55                  60

```
Gly Thr Asp Phe Thr Leu Thr Ile Ser Arg Leu Glu Pro Glu Asp Phe
 65                  70                  75                  80

Ala Val Tyr Tyr Cys Gln Gln Tyr Gly Ser Ser Arg Leu Thr Phe Gly
                 85                  90                  95

Gly Gly Thr Lys Val Glu Ile Lys Arg
            100                 105

<210> SEQ ID NO 26
<211> LENGTH: 110
<212> TYPE: PRT
<213> ORGANISM: Artificial Sequence
<220> FEATURE:
<223> OTHER INFORMATION: synthetic

<400> SEQUENCE: 26

Leu Thr His Pro Ser Pro Val Ser Gly Ala Pro Trp Gln Arg Val Thr
  1               5                  10                  15

Ile Ser Cys Thr Gly Ser Thr Ser His Ile Gly Ala Arg Tyr Asp Val
                 20                  25                  30

His Trp Tyr Gln Gln Leu Pro Gly Thr Ala Pro Lys Leu Leu Ile Tyr
             35                  40                  45

Gly Asn Thr Asn Arg Pro Ser Gly Val Pro Asp Arg Phe Ser Gly Ser
         50                  55                  60

Lys Ser Gly Thr Ser Ser Leu Ala Ile Thr Gly Leu Gln Ala Glu
 65                  70                  75                  80

Asp Glu Ala Asp Tyr Tyr Cys Gln Ser Tyr Asp Ser Ser Leu Ser Gly
                 85                  90                  95

Ser Trp Val Phe Gly Gly Gly Thr Lys Leu Thr Val Leu Gly
            100                 105                 110

<210> SEQ ID NO 27
<211> LENGTH: 106
<212> TYPE: PRT
<213> ORGANISM: Artificial Sequence
<220> FEATURE:
<223> OTHER INFORMATION: synthetic

<400> SEQUENCE: 27

Met Thr Gln Ser Pro Gly Thr Leu Ser Leu Ser Pro Gly Glu Arg Ala
  1               5                  10                  15

Thr Leu Ser Cys Arg Ala Ser Gln Asn Val Thr Asn Ser Tyr Val Gly
                 20                  25                  30

Trp Tyr Gln Lys Lys Pro Gly Gln Ala Pro Met Leu Leu Ile Tyr Gly
             35                  40                  45

Ala Ser Arg Arg Ala Ala Gly Ile Pro Asp Arg Phe Ser Gly Ser Gly
         50                  55                  60

Ser Gly Thr Tyr Phe Thr Leu Thr Ile Ser Arg Leu Asp Ala Glu Asp
 65                  70                  75                  80

Phe Ala Val Tyr Tyr Cys Gln Gln Tyr Gly Ser Ser Pro Leu Thr Phe
                 85                  90                  95

Gly Gly Gly Thr Lys Val Glu Ile Lys Arg
            100                 105

<210> SEQ ID NO 28
<211> LENGTH: 105
<212> TYPE: PRT
<213> ORGANISM: Artificial Sequence
<220> FEATURE:
<223> OTHER INFORMATION: synthetic
```

<400> SEQUENCE: 28

Leu Thr Gln Ser Pro Ala Thr Leu Ser Val Ser Pro Gly Glu Arg Val
1               5                   10                  15

Thr Leu Ser Cys Arg Ala Ser Gln Ser Ile Asn Arg Asn Leu Ala Trp
            20                  25                  30

Tyr Gln Gln Lys Pro Gly Gln Ala Pro Arg Leu Leu Ile Tyr Gly Ala
        35                  40                  45

Ser Thr Arg Ala Thr Gly Ile Pro Ala Arg Phe Ser Gly Ser Gly Ser
50                  55                  60

Gly Thr Asp Phe Thr Leu Thr Ile Asn Arg Leu Glu Pro Glu Asn Phe
65                  70                  75                  80

Ala Val Tyr Tyr Cys Gln Gln Tyr Gly Gly Ser Ser Phe Thr Phe Gly
                85                  90                  95

Pro Gly Thr Lys Val Asp Ile Lys Arg
            100                 105

<210> SEQ ID NO 29
<211> LENGTH: 106
<212> TYPE: PRT
<213> ORGANISM: Artificial Sequence
<220> FEATURE:
<223> OTHER INFORMATION: synthetic

<400> SEQUENCE: 29

Met Thr Gln Ser Pro Gly Thr Leu Ser Leu Ser Pro Gly Glu Arg Ala
1               5                   10                  15

Thr Leu Ser Cys Arg Ala Ser Gln Ser Val Ser Ser Thr Tyr Leu Ser
            20                  25                  30

Trp Tyr Gln Gln Lys Pro Gly Gln Ala Pro Arg Leu Leu Ile Tyr Gly
        35                  40                  45

Ala Ser Ser Arg Ala Thr Gly Thr Pro Asp Arg Phe Ser Gly Ser Gly
50                  55                  60

Ser Gly Lys Tyr Phe Thr Leu Thr Ile Ser Arg Leu Glu Pro Glu Asp
65                  70                  75                  80

Phe Ala Val Tyr Tyr Cys Gln His Tyr Gly Ser Ser Pro Tyr Thr Phe
                85                  90                  95

Gly Gln Gly Thr Lys Leu Glu Ile Lys Arg
            100                 105

<210> SEQ ID NO 30
<211> LENGTH: 104
<212> TYPE: PRT
<213> ORGANISM: Artificial Sequence
<220> FEATURE:
<223> OTHER INFORMATION: synthetic

<400> SEQUENCE: 30

Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Arg Leu Ala Trp Tyr
            20                  25                  30

Gln Gln Lys Pro Gly Gln Ala Pro Arg Leu Leu Ile Tyr Gly Thr Ser
        35                  40                  45

Ser Arg Ala Thr Gly Ile Pro Asp Arg Phe Ser Gly Ser Gly Ser Gly
50                  55                  60

Thr Asp Phe Thr Leu Thr Ile Ser Arg Leu Glu Pro Glu Asp Phe Ala
65                  70                  75                  80

```
Val Tyr Tyr Cys Gln Gln Phe Arg Asn Ser Leu Leu Thr Phe Gly Gly
                85                  90                  95

Gly Thr Lys Val Glu Ile Thr Arg
            100

<210> SEQ ID NO 31
<211> LENGTH: 104
<212> TYPE: PRT
<213> ORGANISM: Artificial Sequence
<220> FEATURE:
<223> OTHER INFORMATION: synthetic

<400> SEQUENCE: 31

Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Arg Leu Ala Trp Tyr
            20                  25                  30

Gln Gln Lys Pro Gly Gln Ala Pro Arg Leu Leu Ile Tyr Gly Thr Ser
        35                  40                  45

Ser Arg Ala Thr Gly Ile Pro Asp Arg Phe Ser Gly Ser Gly Ser Gly
    50                  55                  60

Thr Asp Phe Thr Leu Thr Ile Ser Arg Leu Glu Pro Glu Asp Phe Ala
65                  70                  75                  80

Val Tyr Tyr Cys Gln Gln Phe Arg Asn Ser Leu Leu Thr Phe Gly Gly
                85                  90                  95

Gly Thr Lys Val Glu Ile Thr Arg
            100

<210> SEQ ID NO 32
<211> LENGTH: 106
<212> TYPE: PRT
<213> ORGANISM: Artificial Sequence
<220> FEATURE:
<223> OTHER INFORMATION: synthetic

<400> SEQUENCE: 32

Leu Thr Gln Ser Pro Gly Thr Leu Ser Leu Ser Pro Gly Asp Arg Ala
1               5                   10                  15

Thr Leu Ser Cys Arg Ala Arg Gln Ser Leu Ser Ser Arg Ser Leu Ala
            20                  25                  30

Trp Tyr Gln Gln Arg Pro Gly Gln Ala Pro Arg Leu Leu Ile Tyr Gly
        35                  40                  45

Ala Ser Thr Arg Ala Thr Gly Ile Pro Asp Arg Phe Ser Gly Ser Gly
    50                  55                  60

Ser Gly Thr Glu Phe Thr Leu Thr Ile Ser Arg Leu Glu Pro Glu Asp
65                  70                  75                  80

Phe Ala Val Tyr Tyr Cys Gln Gln Tyr Gly Ser Ser Arg Leu Thr Phe
                85                  90                  95

Gly Gly Gly Thr Lys Val Glu Ile Lys Arg
            100                 105

<210> SEQ ID NO 33
<211> LENGTH: 105
<212> TYPE: PRT
<213> ORGANISM: Artificial Sequence
<220> FEATURE:
<223> OTHER INFORMATION: synthetic

<400> SEQUENCE: 33
```

Leu Thr Gln Ser Pro Gly Thr Leu Ser Leu Ser Pro Gly Glu Ser Ala
1               5                   10                  15

Thr Leu Ser Cys Arg Ala Ser Pro Ser Val Thr Arg Ser Leu Ala Trp
            20                  25                  30

Tyr Gln Gln Lys Pro Gly Gln Ser Pro Arg Leu Leu Ile Tyr Gly Ala
        35                  40                  45

Ser Thr Arg Ala Thr Gly Ile Pro Asp Arg Phe Ser Gly Ser Gly Ser
50                  55                  60

Gly Thr Asp Phe Thr Leu Thr Ile Ser Arg Leu Glu Pro Glu Asp Phe
65                  70                  75                  80

Ala Val Tyr Tyr Cys Gln Gln Tyr Gly Ser Ser Arg Leu Thr Phe Gly
                85                  90                  95

Gly Gly Thr Lys Val Glu Ile Lys Arg
            100                 105

<210> SEQ ID NO 34
<211> LENGTH: 104
<212> TYPE: PRT
<213> ORGANISM: Artificial Sequence
<220> FEATURE:
<223> OTHER INFORMATION: synthetic

<400> SEQUENCE: 34

Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Arg Leu Ala Trp Tyr
            20                  25                  30

Gln Gln Lys Pro Gly Gln Ala Pro Arg Leu Leu Ile Tyr Gly Thr Ser
        35                  40                  45

Ser Arg Ala Thr Gly Ile Pro Asp Arg Phe Ser Gly Ser Gly Ser Gly
50                  55                  60

Thr Asp Phe Thr Leu Thr Ile Ser Arg Leu Glu Pro Glu Asp Phe Ala
65                  70                  75                  80

Val Tyr Tyr Cys Gln Gln Phe Arg Asn Ser Leu Leu Thr Phe Gly Gly
                85                  90                  95

Gly Thr Lys Val Glu Ile Thr Arg
            100

<210> SEQ ID NO 35
<211> LENGTH: 106
<212> TYPE: PRT
<213> ORGANISM: Artificial Sequence
<220> FEATURE:
<223> OTHER INFORMATION: synthetic

<400> SEQUENCE: 35

Leu Thr Gln Ser Pro Asp Thr Leu Ser Leu Ser Pro Gly Glu Arg Ala
1               5                   10                  15

Thr Leu Ser Cys Arg Ala Ser Arg Ser Ile Gly Ser Thr Asn Leu Ala
            20                  25                  30

Trp Tyr Gln Gln Lys Ala Gly Gln Ala Pro Met Leu Leu Ile Tyr Gly
        35                  40                  45

Thr Ser Asn Arg Ala Thr Gly Ile Pro Asp Arg Phe Ser Gly Ser Gly
        50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Leu Phe Thr Phe
                85                  90                  95

```
Gly Pro Gly Thr Lys Val Asp Ile Lys Arg
            100                 105

<210> SEQ ID NO 36
<211> LENGTH: 105
<212> TYPE: PRT
<213> ORGANISM: Artificial Sequence
<220> FEATURE:
<223> OTHER INFORMATION: synthetic

<400> SEQUENCE: 36

Leu Thr Gln Ser Pro Gly Thr Leu Ser Leu Ser Pro Gly Glu Ser Ala
1               5                   10                  15

Thr Leu Ser Cys Arg Ala Ser Pro Ser Val Thr Arg Ser Leu Ala Trp
            20                  25                  30

Tyr Gln Gln Lys Pro Gly Gln Ser Pro Arg Leu Leu Ile Tyr Gly Ala
        35                  40                  45

Ser Thr Arg Ala Thr Gly Ile Pro Asp Arg Phe Ser Gly Ser Gly Ser
    50                  55                  60

Gly Thr Asp Phe Thr Leu Thr Ile Ser Arg Leu Glu Pro Glu Asp Phe
65                  70                  75                  80

Ala Val Tyr Tyr Cys Gln Gln Tyr Gly Ser Ser Arg Leu Thr Phe Gly
                85                  90                  95

Gly Gly Thr Lys Val Glu Ile Lys Arg
            100                 105

<210> SEQ ID NO 37
<211> LENGTH: 106
<212> TYPE: PRT
<213> ORGANISM: Artificial Sequence
<220> FEATURE:
<223> OTHER INFORMATION: synthetic

<400> SEQUENCE: 37

Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Ser Ser Thr Leu Ala
            20                  25                  30

Trp Tyr Gln Gln Lys Pro Gly Gln Thr Pro Arg Leu Leu Ile Tyr Gly
        35                  40                  45

Ala Ser Ser Arg Ala Thr Gly Ile Pro Asp Arg Phe Ser Gly Ser Gly
    50                  55                  60

Ser Gly Ala Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Arg Leu Thr Phe
                85                  90                  95

Gly Gly Gly Thr Lys Val Glu Ile Lys Arg
            100                 105

<210> SEQ ID NO 38
<211> LENGTH: 106
<212> TYPE: PRT
<213> ORGANISM: Artificial Sequence
<220> FEATURE:
<223> OTHER INFORMATION: synthetic

<400> SEQUENCE: 38

Leu Thr Gln Ser Pro Gly Thr Leu Ser Leu Ser Pro Gly Glu Arg Ala
1               5                   10                  15
```

```
Thr Leu Ser Cys Arg Ala Ser Gln Ser Val Ser Arg Ser Leu Ala
            20                  25                  30

Trp Tyr Gln Gln Lys Pro Gly Gln Ala Pro Arg Leu Leu Ile Tyr Gly
        35                  40                  45

Ala Ser Thr Arg Ala Thr Gly Ile Pro Asp Arg Phe Ser Gly Ser Gly
    50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Arg Phe Thr Phe
                85                  90                  95

Gly Gly Gly Thr Lys Val Glu Ile Lys Arg
            100                 105
```

<210> SEQ ID NO 39
<211> LENGTH: 106
<212> TYPE: PRT
<213> ORGANISM: Artificial Sequence
<220> FEATURE:
<223> OTHER INFORMATION: synthetic

<400> SEQUENCE: 39

```
Leu Thr Gln Ser Pro Asp Thr Leu Ser Leu Ser Pro Gly Glu Arg Ala
1               5                   10                  15

Thr Leu Ser Cys Arg Ala Ser Arg Ser Ile Gly Ser Thr Asn Leu Ala
            20                  25                  30

Trp Tyr Gln Gln Lys Ala Gly Gln Ala Pro Met Leu Leu Ile Tyr Gly
        35                  40                  45

Thr Ser Asn Arg Ala Thr Gly Ile Pro Asp Arg Phe Ser Gly Ser Gly
    50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Leu Phe Thr Phe
                85                  90                  95

Pro Gly Gly Thr Lys Asp Glu Ile Lys Arg
            100                 105
```

<210> SEQ ID NO 40
<211> LENGTH: 107
<212> TYPE: PRT
<213> ORGANISM: Artificial Sequence
<220> FEATURE:
<223> OTHER INFORMATION: synthetic

<400> SEQUENCE: 40

```
Leu Thr Gln Ser Pro Ala Thr Leu Ser Leu Ser Pro Gly Gly Arg Ala
1               5                   10                  15

Thr Leu Ser Cys Arg Ala Ser Gln Ser Val Gly Ser Ser Leu Ala
            20                  25                  30

Trp Tyr Gln Gln Lys Pro Gly Gln Ala Pro Arg Leu Leu Ile Tyr Ala
        35                  40                  45

Thr Ser Thr Arg Ala Thr Gly Ile Pro Asp Arg Phe Ser Gly Ser Gly
    50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Pro Leu Phe Thr
                85                  90                  95

Phe Gly Pro Gly Thr Lys Val Asp Ile Lys Arg
            100                 105
```

<210> SEQ ID NO 41
<211> LENGTH: 104
<212> TYPE: PRT
<213> ORGANISM: Artificial Sequence
<220> FEATURE:
<223> OTHER INFORMATION: synthetic

<400> SEQUENCE: 41

Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Arg Leu Thr Trp Tyr
            20                  25                  30

Gln Gln Lys Pro Gly Gln Ala Pro Arg Leu Leu Ile Tyr Gly Thr Ser
        35                  40                  45

Ser Arg Ala Thr Gly Ile Pro Asn Arg Phe Ser Gly Ser Gly Ser Gly
    50                  55                  60

Thr Asp Phe Thr Leu Thr Ile Thr Arg Leu Glu Pro Glu Asp Phe Ala
65                  70                  75                  80

Val Tyr Tyr Cys Gln Gln Phe Arg Asn Ser Leu Leu Thr Phe Gly Gly
                85                  90                  95

Gly Thr Lys Val Glu Ile Lys Arg
            100

<210> SEQ ID NO 42
<211> LENGTH: 104
<212> TYPE: PRT
<213> ORGANISM: Artificial Sequence
<220> FEATURE:
<223> OTHER INFORMATION: synthetic

<400> SEQUENCE: 42

Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Arg Leu Thr Trp Tyr
            20                  25                  30

Gln Gln Lys Pro Gly Gln Ala Pro Arg Leu Leu Ile Tyr Gly Thr Ser
        35                  40                  45

Ser Arg Ala Thr Gly Ile Pro Asn Arg Phe Ser Gly Ser Gly Ser Gly
    50                  55                  60

Thr Asp Phe Thr Leu Thr Ile Thr Arg Leu Glu Pro Glu Asp Phe Ala
65                  70                  75                  80

Val Tyr Tyr Cys Gln Gln Phe Arg Asn Ser Leu Leu Thr Phe Gly Gly
                85                  90                  95

Gly Thr Lys Val Glu Ile Thr Arg
            100

<210> SEQ ID NO 43
<211> LENGTH: 106
<212> TYPE: PRT
<213> ORGANISM: Artificial Sequence
<220> FEATURE:
<223> OTHER INFORMATION: synthetic

<400> SEQUENCE: 43

Leu Thr Gln Ser Leu Gly Thr Leu Ser Leu Ser Pro Gly Glu Arg Ala
1               5                   10                  15

Thr Leu Ser Cys Arg Ala Ser Gln Ser Val Ser Ser Thr Leu Ala
            20                  25                  30

Trp Tyr Gln Gln Lys Pro Gly Gln Ala Pro Arg Leu Leu Ile Tyr Gly
            35                  40                  45

Ala Ser Ser Arg Ala Thr Gly Ile Pro Asp Arg Phe Ser Gly Ser Gly
 50                  55                  60

Ser Gly Thr Asp Phe Thr Leu Thr Ile Ser Arg Leu Glu Pro Glu Asp
 65                  70                  75                  80

Phe Ala Val Tyr Tyr Cys Gln Gln Tyr Gly Ser Ser Lys Ile Thr Phe
                 85                  90                  95

Gly Gln Gly Thr Arg Leu Glu Ile Lys Arg
            100                 105

<210> SEQ ID NO 44
<211> LENGTH: 106
<212> TYPE: PRT
<213> ORGANISM: Artificial Sequence
<220> FEATURE:
<223> OTHER INFORMATION: synthetic

<400> SEQUENCE: 44

Leu Thr Gln Ser Pro Gly Thr Leu Ser Leu Ser Pro Gly Asp Arg Ala
 1               5                  10                  15

Thr Leu Ser Cys Arg Ala Arg Gln Ser Leu Ser Ser Arg Ser Leu Ala
            20                  25                  30

Trp Tyr Gln Gln Arg Pro Gly Gln Ala Pro Arg Leu Leu Ile Tyr Gly
            35                  40                  45

Ala Ser Thr Arg Ala Thr Gly Ile Pro Asp Arg Phe Ser Gly Ser Gly
 50                  55                  60

Ser Gly Thr Glu Phe Thr Leu Thr Ile Ser Arg Leu Glu Pro Glu Asp
 65                  70                  75                  80

Phe Ala Val Tyr Tyr Cys Gln Gln Tyr Gly Ser Ser Arg Leu Thr Phe
                 85                  90                  95

Gly Gly Gly Thr Lys Val Glu Ile Lys Arg
            100                 105

<210> SEQ ID NO 45
<211> LENGTH: 105
<212> TYPE: PRT
<213> ORGANISM: Artificial Sequence
<220> FEATURE:
<223> OTHER INFORMATION: synthetic

<400> SEQUENCE: 45

Leu Thr Gln Ser Pro Ser Ser Val Ser Ala Ser Val Gly Asp Arg Val
 1               5                  10                  15

Thr Ile Thr Cys Arg Ala Ser Gln Gly Ile Ser Ser Trp Leu Ala Trp
            20                  25                  30

Tyr Gln Gln Arg Pro Gly Lys Ala Pro Lys Leu Leu Ile Tyr Gly Ala
            35                  40                  45

Ser Asn Leu Gln Ser Gly Val Pro Ser Arg Phe Ser Gly Ser Gly Ser
 50                  55                  60

Gly Thr Asp Phe Thr Leu Thr Ile Ser Ser Leu Gln Pro Glu Asp Val
 65                  70                  75                  80

Ala Thr Tyr Tyr Cys Gln His Ala Asn Ser Phe Pro Arg Thr Phe Gly
                 85                  90                  95

Gly Gly Thr Lys Val Glu Val Lys Arg
            100                 105

<210> SEQ ID NO 46

```
<211> LENGTH: 109
<212> TYPE: PRT
<213> ORGANISM: Artificial Sequence
<220> FEATURE:
<223> OTHER INFORMATION: synthetic

<400> SEQUENCE: 46

Leu Thr Gln Pro His Ser Val Ser Glu Ser Pro Gly Lys Thr Val Thr
1               5                   10                  15

Ile Ser Cys Thr Arg Ser Ser Gly Ser Ile Ala Ser Asn Tyr Val Gln
            20                  25                  30

Trp Tyr Gln Gln Arg Pro Gly Ser Ala Pro Thr Thr Val Ile Tyr Glu
        35                  40                  45

Asp Thr Gln Arg Pro Ser Gly Val Pro Asp Arg Phe Ser Gly Ser Ile
50                  55                  60

Asp Thr Ser Ser Asn Ser Ala Ser Leu Arg Ile Ser Gly Leu Lys Pro
65                  70                  75                  80

Glu Asp Glu Ala Asp Tyr Tyr Cys Gln Ser Tyr Ala Ser Gly Ser Leu
                85                  90                  95

Ile Val Phe Gly Gly Gly Thr Lys Leu Thr Val Leu Gly
            100                 105

<210> SEQ ID NO 47
<211> LENGTH: 105
<212> TYPE: PRT
<213> ORGANISM: Artificial Sequence
<220> FEATURE:
<223> OTHER INFORMATION: synthetic

<400> SEQUENCE: 47

Leu Thr Gln Ser Pro Ala Thr Leu Ser Gly Ser Pro Gly Glu Arg Ala
1               5                   10                  15

Thr Leu Ser Cys Arg Ala Ser Gln Thr Val Ser Ser Asn Leu Ala Trp
            20                  25                  30

Tyr Gln Gln Lys Pro Gly Gln Ala Pro Arg Leu Leu Ile Tyr Gly Ser
        35                  40                  45

Ser Thr Arg Ala Thr Gly Ile Pro Ala Arg Phe Ser Gly Ser Gly Ser
50                  55                  60

Gly Thr Asp Phe Thr Leu Thr Ile Ser Arg Leu Glu Pro Glu Asp Phe
65                  70                  75                  80

Ala Val Tyr Tyr Cys Gln Gln Tyr Gly Ser Ser Arg Leu Thr Phe Gly
                85                  90                  95

Gly Gly Thr Lys Val Glu Ile Lys Arg
            100                 105

<210> SEQ ID NO 48
<211> LENGTH: 109
<212> TYPE: PRT
<213> ORGANISM: Artificial Sequence
<220> FEATURE:
<223> OTHER INFORMATION: synthetic

<400> SEQUENCE: 48

Leu Thr Gln Pro Pro Ser Val Ser Gly Ala Pro Gly Gln Arg Val Thr
1               5                   10                  15

Ile Ser Cys Thr Gly Ser Ser Ser Asn Ile Gly Ala Gly Tyr Asp Val
            20                  25                  30

His Trp Tyr Gln Gln Leu Pro Gly Thr Ala Pro Lys Leu Leu Ile Tyr
        35                  40                  45
```

```
Gly Asn Ser Asn Arg Pro Ser Gly Val Pro Asp Arg Phe Ser Gly Ser
        50                  55                  60
Lys Ser Gly Thr Ser Ala Ser Leu Ala Ile Thr Gly Leu Gln Ala Glu
 65                  70                  75                  80
Asp Glu Ala Asp Tyr Tyr Cys Gln Ser Tyr Asp Ser Ser Leu Ser Gly
                 85                  90                  95
Ser Val Phe Gly Gly Gly Thr Lys Leu Thr Val Leu Gly
                100                 105
```

<210> SEQ ID NO 49
<211> LENGTH: 210
<212> TYPE: PRT
<213> ORGANISM: Artificial Sequence
<220> FEATURE:
<223> OTHER INFORMATION: synthetic

<400> SEQUENCE: 49

```
Leu Thr Gln Ser Pro Gly Thr Leu Ser Leu Ser Pro Gly Glu Arg Ala
 1               5                  10                  15
Thr Leu Ser Cys Arg Ala Ser Gln Ser Val Ser Arg Leu Ala Trp Tyr
             20                  25                  30
Gln Gln Lys Pro Gly Gln Ala Pro Arg Leu Leu Ile Tyr Gly Thr Ser
         35                  40                  45
Ser Arg Ala Thr Gly Ile Pro Asp Arg Phe Ser Gly Ser Gly Ser Gly
     50                  55                  60
Thr Asp Phe Thr Leu Thr Ile Ser Arg Leu Glu Pro Glu Asp Phe Ala
 65                  70                  75                  80
Val Tyr Tyr Cys Gln Gln Phe Arg Asn Ser Leu Leu Thr Phe Gly Gly
                 85                  90                  95
Gly Thr Lys Val Glu Ile Thr Arg Thr Val Ala Ala Pro Ser Val Phe
                100                 105                 110
Ile Phe Pro Pro Ser Asp Glu Gln Leu Lys Ser Gly Thr Ala Ser Val
            115                 120                 125
Val Cys Leu Leu Asn Asn Phe Tyr Pro Arg Glu Ala Lys Val Gln Trp
        130                 135                 140
Lys Val Asp Asn Ala Leu Gln Ser Gly Asn Ser Gln Glu Ser Val Thr
145                 150                 155                 160
Glu Gln Asp Ser Lys Asp Ser Thr Tyr Ser Leu Ser Ser Thr Leu Thr
                165                 170                 175
Leu Ser Lys Ala Asp Tyr Glu Lys His Lys Val Tyr Ala Cys Glu Val
                180                 185                 190
Thr His Gln Gly Leu Ser Ser Pro Val Thr Lys Ser Phe Asn Arg Gly
            195                 200                 205
Glu Cys
    210
```

<210> SEQ ID NO 50
<211> LENGTH: 210
<212> TYPE: PRT
<213> ORGANISM: Artificial Sequence
<220> FEATURE:
<223> OTHER INFORMATION: synthetic

<400> SEQUENCE: 50

```
Leu Thr Gln Ser Pro Gly Thr Leu Ser Leu Ser Pro Gly Glu Arg Ala
 1               5                  10                  15
Thr Leu Ser Cys Arg Ala Ser Gln Ser Val Ser Arg Leu Ala Trp Tyr
             20                  25                  30
```

Gln Gln Lys Pro Gly Gln Ala Pro Arg Leu Leu Ile Tyr Gly Thr Ser
                35                  40                  45

Ser Arg Ala Thr Gly Ile Pro Asp Arg Phe Ser Gly Ser Gly Ser Gly
 50                  55                  60

Thr Asp Phe Thr Leu Thr Ile Ser Arg Leu Glu Pro Glu Asp Phe Ala
 65                  70                  75                  80

Val Tyr Tyr Cys Gln Gln Phe Arg Asn Ser Leu Leu Thr Phe Gly Gly
                85                  90                  95

Gly Thr Lys Val Glu Ile Thr Arg Thr Val Ala Ala Pro Ser Val Phe
               100                 105                 110

Ile Phe Pro Pro Ser Asp Glu Gln Leu Lys Ser Gly Thr Ala Ser Val
               115                 120                 125

Val Cys Leu Leu Asn Asn Phe Tyr Pro Arg Glu Ala Lys Val Gln Trp
           130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
               165                 170                 175

Leu Ser Lys Ala Asp Tyr Glu Lys His Lys Val Tyr Ala Cys Glu Val
           180                 185                 190

Thr His Gln Gly Leu Ser Ser Pro Val Thr Lys Ser Phe Asn Arg Gly
           195                 200                 205

Glu Cys
   210

<210> SEQ ID NO 51
<211> LENGTH: 212
<212> TYPE: PRT
<213> ORGANISM: Artificial Sequence
<220> FEATURE:
<223> OTHER INFORMATION: synthetic

<400> SEQUENCE: 51

Leu Thr Gln Ser Pro Gly Thr Leu Ser Leu Ser Pro Gly Asp Arg Ala
 1               5                  10                  15

Thr Leu Ser Cys Arg Ala Arg Gln Ser Leu Ser Ser Arg Ser Leu Ala
                20                  25                  30

Trp Tyr Gln Gln Arg Pro Gly Gln Ala Pro Arg Leu Leu Ile Tyr Gly
                35                  40                  45

Ala Ser Thr Arg Ala Thr Gly Ile Pro Asp Arg Phe Ser Gly Ser Gly
 50                  55                  60

Ser Gly Thr Glu Phe Thr Leu Thr Ile Ser Arg Leu Glu Pro Glu Asp
 65                  70                  75                  80

Phe Ala Val Tyr Tyr Cys Gln Gln Tyr Gly Ser Ser Arg Leu Thr Phe
                85                  90                  95

Gly Gly Gly Thr Lys Val Glu Ile Lys Arg Thr Val Ala Ala Pro Ser
               100                 105                 110

Val Phe Ile Phe Pro Pro Ser Asp Glu Gln Leu Lys Ser Gly Thr Ala
           115                 120                 125

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
               165                 170                 175

```
Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 52
<211> LENGTH: 211
<212> TYPE: PRT
<213> ORGANISM: Artificial Sequence
<220> FEATURE:
<223> OTHER INFORMATION: synthetic

<400> SEQUENCE: 52

Leu Thr Gln Ser Pro Gly Thr Leu Ser Leu Ser Pro Gly Glu Ser Ala
1               5                   10                  15

Thr Leu Ser Cys Arg Ala Ser Pro Ser Val Thr Arg Ser Leu Ala Trp
            20                  25                  30

Tyr Gln Gln Lys Pro Gly Gln Ser Pro Arg Leu Leu Ile Tyr Gly Ala
        35                  40                  45

Ser Thr Arg Ala Thr Gly Ile Pro Asp Arg Phe Ser Gly Ser Gly Ser
50                  55                  60

Gly Thr Asp Phe Thr Leu Thr Ile Ser Arg Leu Glu Pro Glu Asp Phe
65                  70                  75                  80

Ala Val Tyr Tyr Cys Gln Gln Tyr Gly Ser Ser Arg Leu Thr Phe Gly
                85                  90                  95

Gly Gly Thr Lys Val Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 53
<211> LENGTH: 210
<212> TYPE: PRT
<213> ORGANISM: Artificial Sequence
<220> FEATURE:
<223> OTHER INFORMATION: synthetic

<400> SEQUENCE: 53

Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Arg Leu Ala Trp Tyr
            20                  25                  30

Gln Gln Lys Pro Gly Gln Ala Pro Arg Leu Leu Ile Tyr Gly Thr Ser
```

```
                35                  40                  45
Ser Arg Ala Thr Gly Ile Pro Asp Arg Phe Ser Gly Ser Gly
 50                  55                  60

Thr Asp Phe Thr Leu Thr Ile Ser Arg Leu Glu Pro Glu Asp Phe Ala
65                  70                  75                  80

Val Tyr Tyr Cys Gln Gln Phe Arg Asn Ser Leu Leu Thr Phe Gly Gly
                85                  90                  95

Gly Thr Lys Val Glu Ile Thr Arg Thr Val Ala Ala Pro Ser Val Phe
                100                 105                 110

Ile Phe Pro Pro Ser Asp Glu Gln Leu Lys Ser Gly Thr Ala Ser Val
                115                 120                 125

Val Cys Leu Leu Asn Asn Phe Tyr Pro Arg Glu Ala Lys Val Gln Trp
        130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
                180                 185                 190

Thr His Gln Gly Leu Ser Ser Pro Val Thr Lys Ser Phe Asn Arg Gly
                195                 200                 205

Glu Cys
    210

<210> SEQ ID NO 54
<211> LENGTH: 212
<212> TYPE: PRT
<213> ORGANISM: Artificial Sequence
<220> FEATURE:
<223> OTHER INFORMATION: synthetic

<400> SEQUENCE: 54

Leu Thr Gln Ser Pro Asp Thr Leu Ser Leu Ser Pro Gly Glu Arg Ala
1               5                   10                  15

Thr Leu Ser Cys Arg Ala Ser Arg Ser Ile Gly Ser Thr Asn Leu Ala
                20                  25                  30

Trp Tyr Gln Gln Lys Ala Gly Gln Ala Pro Met Leu Leu Ile Tyr Gly
            35                  40                  45

Thr Ser Asn Arg Ala Thr Gly Ile Pro Asp Arg Phe Ser Gly Ser Gly
 50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Leu Phe Thr Phe
                85                  90                  95

Gly Pro Gly Thr Lys Val Asp Ile Lys Arg Thr Val Ala Ala Pro Ser
                100                 105                 110

Val Phe Ile Phe Pro Pro Ser Asp Glu Gln Leu Lys Ser Gly Thr Ala
            115                 120                 125

Ser Val Val Cys Leu Leu Asn Asn Phe Tyr Pro Arg Glu Ala Lys Val
        130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
```

```
                180            185                190
Glu Val Thr His Gln Gly Leu Ser Ser Pro Val Thr Lys Ser Phe Asn
                195                200                205

Arg Gly Glu Cys
    210

<210> SEQ ID NO 55
<211> LENGTH: 211
<212> TYPE: PRT
<213> ORGANISM: Artificial Sequence
<220> FEATURE:
<223> OTHER INFORMATION: synthetic

<400> SEQUENCE: 55

Leu Thr Gln Ser Pro Gly Thr Leu Ser Leu Ser Pro Gly Glu Ser Ala
1               5                   10                  15

Thr Leu Ser Cys Arg Ala Ser Pro Ser Val Thr Arg Ser Leu Ala Trp
                20                  25                  30

Tyr Gln Gln Lys Pro Gly Gln Ser Pro Arg Leu Leu Ile Tyr Gly Ala
            35                  40                  45

Ser Thr Arg Ala Thr Gly Ile Pro Asp Arg Phe Ser Gly Ser Gly Ser
50                  55                  60

Gly Thr Asp Phe Thr Leu Thr Ile Ser Arg Leu Glu Pro Glu Asp Phe
65                  70                  75                  80

Ala Val Tyr Tyr Cys Gln Gln Tyr Gly Ser Ser Arg Leu Thr Phe Gly
                85                  90                  95

Gly Gly Thr Lys Val Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 56
<211> LENGTH: 212
<212> TYPE: PRT
<213> ORGANISM: Artificial Sequence
<220> FEATURE:
<223> OTHER INFORMATION: synthetic

<400> SEQUENCE: 56

Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Ser Ser Thr Leu Ala
                20                  25                  30

Trp Tyr Gln Gln Lys Pro Gly Gln Thr Pro Arg Leu Leu Ile Tyr Gly
            35                  40                  45
```

Ala Ser Ser Arg Ala Thr Gly Ile Pro Asp Arg Phe Ser Gly Ser Gly
    50                  55                  60

Ser Gly Ala Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Arg Leu Thr Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 57
<211> LENGTH: 212
<212> TYPE: PRT
<213> ORGANISM: Artificial Sequence
<220> FEATURE:
<223> OTHER INFORMATION: synthetic

<400> SEQUENCE: 57

Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Ser Arg Ser Leu Ala
            20                  25                  30

Trp Tyr Gln Gln Lys Pro Gly Gln Ala Pro Arg Leu Leu Ile Tyr Gly
        35                  40                  45

Ala Ser Thr Arg Ala Thr Gly Ile Pro Asp Arg Phe Ser Gly Ser Gly
    50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Arg Phe Thr Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Asn Ser Phe Asn
                195                 200                 205

Arg Gly Glu Cys
    210

<210> SEQ ID NO 58
<211> LENGTH: 212
<212> TYPE: PRT
<213> ORGANISM: Artificial Sequence
<220> FEATURE:
<223> OTHER INFORMATION: synthetic

<400> SEQUENCE: 58

Leu Thr Gln Ser Pro Asp Thr Leu Ser Leu Ser Pro Gly Glu Arg Ala
1               5                   10                  15

Thr Leu Ser Cys Arg Ala Ser Arg Ser Ile Gly Ser Thr Asn Leu Ala
            20                  25                  30

Trp Tyr Gln Gln Lys Ala Gly Gln Ala Pro Met Leu Leu Ile Tyr Gly
        35                  40                  45

Thr Ser Asn Arg Ala Thr Gly Ile Pro Asp Arg Phe Ser Gly Ser Gly
    50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Leu Phe Thr Phe
                85                  90                  95

Gly Pro Gly Thr Lys Val Asp Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 59
<211> LENGTH: 211
<212> TYPE: PRT
<213> ORGANISM: Artificial Sequence
<220> FEATURE:
<223> OTHER INFORMATION: synthetic

<400> SEQUENCE: 59

Leu Thr Gln Ser Pro Ser Ser Val Ser Ala Ser Val Gly Asp Arg Val
1               5                   10                  15

Thr Ile Thr Cys Arg Ala Ser Gln Gly Ile Ser Ser Trp Leu Ala Trp
            20                  25                  30

Tyr Gln Gln Arg Pro Gly Lys Ala Pro Lys Leu Leu Ile Tyr Gly Ala
        35                  40                  45

Ser Asn Leu Gln Ser Gly Val Pro Ser Arg Phe Ser Gly Ser Gly Ser
    50                  55                  60

```
Gly Thr Asp Phe Thr Leu Thr Ile Ser Ser Leu Gln Pro Glu Asp Val
 65                  70                  75                  80

Ala Thr Tyr Tyr Cys Gln His Ala Asn Ser Phe Pro Arg Thr Phe Gly
                 85                  90                  95

Gly Gly Thr Lys Val Glu Val Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 60
<211> LENGTH: 214
<212> TYPE: PRT
<213> ORGANISM: Artificial Sequence
<220> FEATURE:
<223> OTHER INFORMATION: synthetic

<400> SEQUENCE: 60

Leu Thr Gln Pro His Ser Val Ser Glu Ser Pro Gly Lys Thr Val Thr
  1               5                  10                  15

Ile Ser Cys Thr Arg Ser Ser Gly Ser Ile Ala Ser Asn Tyr Val Gln
             20                  25                  30

Trp Tyr Gln Gln Arg Pro Gly Ser Ala Pro Thr Thr Val Ile Tyr Glu
         35                  40                  45

Asp Thr Gln Arg Pro Ser Gly Val Pro Asp Arg Phe Ser Gly Ser Ile
 50                  55                  60

Asp Thr Ser Ser Asn Ser Ala Ser Leu Arg Ile Ser Gly Leu Lys Pro
 65                  70                  75                  80

Glu Asp Glu Ala Asp Tyr Tyr Cys Gln Ser Tyr Ala Ser Gly Ser Leu
                 85                  90                  95

Ile Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Val Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
            180                 185                 190

Tyr Ser Cys Gln Val Thr His Glu Gly Ser Thr Val Glu Lys Thr Val
        195                 200                 205
```

Ala Pro Ala Glu Cys Ser
        210

<210> SEQ ID NO 61
<211> LENGTH: 211
<212> TYPE: PRT
<213> ORGANISM: Artificial Sequence
<220> FEATURE:
<223> OTHER INFORMATION: synthetic

<400> SEQUENCE: 61

Leu Thr Gln Ser Pro Ala Thr Leu Ser Gly Ser Pro Gly Glu Arg Ala
1               5                   10                  15

Thr Leu Ser Cys Arg Ala Ser Gln Thr Val Ser Ser Asn Leu Ala Trp
            20                  25                  30

Tyr Gln Gln Lys Pro Gly Gln Ala Pro Arg Leu Leu Ile Tyr Gly Ser
        35                  40                  45

Ser Thr Arg Ala Thr Gly Ile Pro Ala Arg Phe Ser Gly Ser Gly Ser
    50                  55                  60

Gly Thr Asp Phe Thr Leu Thr Ile Ser Arg Leu Glu Pro Glu Asp Phe
65                  70                  75                  80

Ala Val Tyr Tyr Cys Gln Gln Tyr Gly Ser Ser Arg Leu Thr Phe Gly
                85                  90                  95

Gly Gly Thr Lys Val Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
        210

<210> SEQ ID NO 62
<211> LENGTH: 214
<212> TYPE: PRT
<213> ORGANISM: Artificial Sequence
<220> FEATURE:
<223> OTHER INFORMATION: synthetic

<400> SEQUENCE: 62

Leu Thr Gln Pro Pro Ser Val Ser Gly Ala Pro Gly Gln Arg Val Thr
1               5                   10                  15

Ile Ser Cys Thr Gly Ser Ser Ser Asn Ile Gly Ala Gly Tyr Asp Val
            20                  25                  30

His Trp Tyr Gln Gln Leu Pro Gly Thr Ala Pro Lys Leu Leu Ile Tyr
        35                  40                  45

Gly Asn Ser Asn Arg Pro Ser Gly Val Pro Asp Arg Phe Ser Gly Ser
    50                  55                  60

Lys Ser Gly Thr Ser Ala Ser Leu Ala Ile Thr Gly Leu Gln Ala Glu

```
                65                  70                  75                  80
Asp Glu Ala Asp Tyr Tyr Cys Gln Ser Tyr Asp Ser Ser Leu Ser Gly
                    85                  90                  95

Ser Val Phe Gly Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
                115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
                180                 185                 190

Tyr Ser Cys Gln Val Thr His Glu Gly Ser Thr Val Glu Lys Thr Val
                195                 200                 205

Ala Pro Thr Glu Cys Ser
                210

<210> SEQ ID NO 63
<211> LENGTH: 213
<212> TYPE: PRT
<213> ORGANISM: Artificial Sequence
<220> FEATURE:
<223> OTHER INFORMATION: synthetic

<400> SEQUENCE: 63

Leu Thr Gln Ser Pro Ala Thr Leu Ser Leu Ser Pro Gly Gly Arg Ala
1               5                   10                  15

Thr Leu Ser Cys Arg Ala Ser Gln Ser Val Gly Ser Ser Leu Ala
                20                  25                  30

Trp Tyr Gln Gln Lys Pro Gly Gln Ala Pro Arg Leu Leu Ile Tyr Ala
                35                  40                  45

Thr Ser Thr Arg Ala Thr Gly Ile Pro Asp Arg Phe Ser Gly Ser Gly
            50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Pro Leu Phe Thr
                85                  90                  95

Phe Gly Pro Gly Thr Lys Val Asp Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
```

210

<210> SEQ ID NO 64
<211> LENGTH: 210
<212> TYPE: PRT
<213> ORGANISM: Artificial Sequence
<220> FEATURE:
<223> OTHER INFORMATION: synthetic

<400> SEQUENCE: 64

```
Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Arg Leu Thr Trp Tyr
            20                  25                  30

Gln Gln Lys Pro Gly Gln Ala Pro Arg Leu Leu Ile Tyr Gly Thr Ser
        35                  40                  45

Ser Arg Ala Thr Gly Ile Pro Asn Arg Phe Ser Gly Ser Gly Ser Gly
    50                  55                  60

Thr Asp Phe Thr Leu Thr Ile Thr Arg Leu Glu Pro Glu Asp Phe Ala
65                  70                  75                  80

Val Tyr Tyr Cys Gln Gln Phe Arg Asn Ser Leu Leu Thr Phe Gly Gly
                85                  90                  95

Gly Thr Lys Val Glu Ile Thr Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Lys Glu Ala Lys Val Gln Trp
    130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Thr Asn Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys
    210
```

<210> SEQ ID NO 65
<211> LENGTH: 210
<212> TYPE: PRT
<213> ORGANISM: Artificial Sequence
<220> FEATURE:
<223> OTHER INFORMATION: synthetic

<400> SEQUENCE: 65

```
Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Arg Leu Thr Trp Tyr
            20                  25                  30

Gln Gln Lys Pro Gly Gln Ala Pro Arg Leu Leu Ile Tyr Gly Thr Ser
        35                  40                  45

Ser Arg Ala Thr Gly Ile Pro Asn Arg Phe Ser Gly Ser Gly Ser Gly
    50                  55                  60

Thr Asp Phe Thr Leu Thr Ile Thr Arg Leu Glu Pro Glu Asp Phe Ala
65                  70                  75                  80
```

Val Tyr Tyr Cys Gln Gln Phe Arg Asn Ser Leu Leu Thr Phe Gly Gly
                85                  90                  95

Gly Thr Lys Val Glu Ile Thr Arg Thr Val Ala Ala Pro Ser Val Phe
            100                 105                 110

Ile Phe Pro Pro Ser Asp Glu Gln Leu Lys Ser Gly Thr Ala Ser Val
            115                 120                 125

Val Cys Leu Leu Asn Asn Phe Tyr Pro Lys Glu Ala Lys Val Gln Trp
        130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Thr Asn Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys
    210

<210> SEQ ID NO 66
<211> LENGTH: 212
<212> TYPE: PRT
<213> ORGANISM: Artificial Sequence
<220> FEATURE:
<223> OTHER INFORMATION: synthetic

<400> SEQUENCE: 66

Leu Thr Gln Ser Leu Gly Thr Leu Ser Leu Ser Pro Gly Glu Arg Ala
1               5                   10                  15

Thr Leu Ser Cys Arg Ala Ser Gln Ser Val Ser Ser Ser Thr Leu Ala
            20                  25                  30

Trp Tyr Gln Gln Lys Pro Gly Gln Ala Pro Arg Leu Leu Ile Tyr Gly
        35                  40                  45

Ala Ser Ser Arg Ala Thr Gly Ile Pro Asp Arg Phe Ser Gly Ser Gly
    50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Lys Ile Thr Phe
                85                  90                  95

Gly Gln Gly Thr Arg Leu Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

```
<210> SEQ ID NO 67
<211> LENGTH: 212
<212> TYPE: PRT
<213> ORGANISM: Artificial Sequence
<220> FEATURE:
<223> OTHER INFORMATION: synthetic

<400> SEQUENCE: 67

Leu Thr Gln Ser Pro Gly Thr Leu Ser Leu Ser Pro Gly Asp Arg Ala
1               5                   10                  15

Thr Leu Ser Cys Arg Ala Arg Gln Ser Leu Ser Ser Arg Ser Leu Ala
            20                  25                  30

Trp Tyr Gln Gln Arg Pro Gly Gln Ala Pro Arg Leu Leu Ile Tyr Gly
        35                  40                  45

Ala Ser Thr Arg Ala Thr Gly Ile Pro Asp Arg Phe Ser Gly Ser Gly
    50                  55                  60

Ser Gly Thr Glu Phe Thr Leu Thr Ile Ser Arg Leu Glu Pro Glu Asp
65                  70                  75                  80

Phe Ala Val Tyr Tyr Cys Gln Gln Tyr Gly Ser Ser Arg Leu Thr Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
        210

<210> SEQ ID NO 68
<211> LENGTH: 226
<212> TYPE: PRT
<213> ORGANISM: Artificial Sequence
<220> FEATURE:
<223> OTHER INFORMATION: synthetic

<400> SEQUENCE: 68

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Thr Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Val Arg Ala Asn Tyr Tyr Gly Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Ala
    210                 215                 220

Ala Ala
225

<210> SEQ ID NO 69
<211> LENGTH: 107
<212> TYPE: PRT
<213> ORGANISM: Artificial Sequence
<220> FEATURE:
<223> OTHER INFORMATION: synthetic
<220> FEATURE:
<221> NAME/KEY: X
<222> LOCATION: (1)..(1)
<223> OTHER INFORMATION: L or M
<220> FEATURE:
<221> NAME/KEY: X
<222> LOCATION: (5)..(5)
<223> OTHER INFORMATION: P or L
<220> FEATURE:
<221> NAME/KEY: X
<222> LOCATION: (6)..(6)
<223> OTHER INFORMATION: G or D or A
<220> FEATURE:
<221> NAME/KEY: X
<222> LOCATION: (10)..(10)
<223> OTHER INFORMATION: L or G or V
<220> FEATURE:
<221> NAME/KEY: X
<222> LOCATION: (14)..(14)
<223> OTHER INFORMATION: E or G or D
<220> FEATURE:
<221> NAME/KEY: X
<222> LOCATION: (15)..(15)
<223> OTHER INFORMATION: R or S
<220> FEATURE:
<221> NAME/KEY: X
<222> LOCATION: (16)..(16)
<223> OTHER INFORMATION: A or V
<220> FEATURE:
<221> NAME/KEY: X
<222> LOCATION: (21)..(21)
<223> OTHER INFORMATION: R or G
<220> FEATURE:
<221> NAME/KEY: X
<222> LOCATION: (23)..(23)
<223> OTHER INFORMATION: R or S
<220> FEATURE:
<221> NAME/KEY: X
<222> LOCATION: (24)..(24)
<223> OTHER INFORMATION: Q or P or R
<220> FEATURE:
<221> NAME/KEY: X
<222> LOCATION: (25)..(25)
<223> OTHER INFORMATION: S or T or N -continued

```
<220> FEATURE:
<221> NAME/KEY: X
<222> LOCATION: (26)..(26)
<223> OTHER INFORMATION: V or L or I
<220> FEATURE:
<221> NAME/KEY: X
<222> LOCATION: (27)..(27)
<223> OTHER INFORMATION: S or T or G or N or absent
<220> FEATURE:
<221> NAME/KEY: X
<222> LOCATION: (28)..(28)
<223> OTHER INFORMATION: S or T or R or N or absent
<220> FEATURE:
<221> NAME/KEY: X
<222> LOCATION: (29)..(29)
<223> OTHER INFORMATION: S or R or T or N or absent
<220> FEATURE:
<221> NAME/KEY: X
<222> LOCATION: (30)..(30)
<223> OTHER INFORMATION: R or T or S or N or D or Y
<220> FEATURE:
<221> NAME/KEY: X
<222> LOCATION: (31)..(31)
<223> OTHER INFORMATION: V or L
<220> FEATURE:
<221> NAME/KEY: X
<222> LOCATION: (32)..(32)
<223> OTHER INFORMATION: A or T or S or G
<220> FEATURE:
<221> NAME/KEY: X
<222> LOCATION: (36)..(36)
<223> OTHER INFORMATION: K or Q
<220> FEATURE:
<221> NAME/KEY: X
<222> LOCATION: (37)..(37)
<223> OTHER INFORMATION: K or R
<220> FEATURE:
<221> NAME/KEY: X
<222> LOCATION: (38)..(38)
<223> OTHER INFORMATION: P or A
<220> FEATURE:
<221> NAME/KEY: X
<222> LOCATION: (40)..(40)
<223> OTHER INFORMATION: Q or L
<220> FEATURE:
<221> NAME/KEY: X
<222> LOCATION: (41)..(41)
<223> OTHER INFORMATION: A or T or S
<220> FEATURE:
<221> NAME/KEY: X
<222> LOCATION: (43)..(43)
<223> OTHER INFORMATION: R or M
<220> FEATURE:
<221> NAME/KEY: X
<222> LOCATION: (48)..(48)
<223> OTHER INFORMATION: G or A
<220> FEATURE:
<221> NAME/KEY: X
<222> LOCATION: (49)..(49)
<223> OTHER INFORMATION: T or A
<220> FEATURE:
<221> NAME/KEY: X
<222> LOCATION: (51)..(51)
<223> OTHER INFORMATION: S or T or N or R
<220> FEATURE:
<221> NAME/KEY: X
<222> LOCATION: (54)..(54)
<223> OTHER INFORMATION: T or A
<220> FEATURE:
<221> NAME/KEY: X
<222> LOCATION: (56)..(56)
<223> OTHER INFORMATION: T or I
<220> FEATURE:
<221> NAME/KEY: X
<222> LOCATION: (58)..(58)
<223> OTHER INFORMATION: N or A or D
<220> FEATURE:
<221> NAME/KEY: X
<222> LOCATION: (62)..(62)
```

```
<223> OTHER INFORMATION: G or A
<220> FEATURE:
<221> NAME/KEY: X
<222> LOCATION: (67)..(67)
<223> OTHER INFORMATION: T or A or K
<220> FEATURE:
<221> NAME/KEY: X
<222> LOCATION: (68)..(68)
<223> OTHER INFORMATION: D or E or Y
<220> FEATURE:
<221> NAME/KEY: X
<222> LOCATION: (74)..(74)
<223> OTHER INFORMATION: T or S or N
<220> FEATURE:
<221> NAME/KEY: X
<222> LOCATION: (77)..(77)
<223> OTHER INFORMATION: E or D
<220> FEATURE:
<221> NAME/KEY: X
<222> LOCATION: (78)..(78)
<223> OTHER INFORMATION: P or A
<220> FEATURE:
<221> NAME/KEY: X
<222> LOCATION: (80)..(80)
<223> OTHER INFORMATION: D or N
<220> FEATURE:
<221> NAME/KEY: X
<222> LOCATION: (83)..(83)
<223> OTHER INFORMATION: M or V
<220> FEATURE:
<221> NAME/KEY: X
<222> LOCATION: (88)..(88)
<223> OTHER INFORMATION: Q or H
<220> FEATURE:
<221> NAME/KEY: X
<222> LOCATION: (89)..(89)
<223> OTHER INFORMATION: F or Y
<220> FEATURE:
<221> NAME/KEY: X
<222> LOCATION: (90)..(90)
<223> OTHER INFORMATION: R or G
<220> FEATURE:
<221> NAME/KEY: X
<222> LOCATION: (91)..(91)
<223> OTHER INFORMATION: N or S
<220> FEATURE:
<221> NAME/KEY: X
<222> LOCATION: (93)..(93)
<223> OTHER INFORMATION: R or L or P or K or S
<220> FEATURE:
<221> NAME/KEY: X
<222> LOCATION: (94)..(94)
<223> OTHER INFORMATION: L or absent
<220> FEATURE:
<221> NAME/KEY: X
<222> LOCATION: (95)..(95)
<223> OTHER INFORMATION: L or I or F or Y
<220> FEATURE:
<221> NAME/KEY: X
<222> LOCATION: (99)..(99)
<223> OTHER INFORMATION: G or Q or P
<220> FEATURE:
<221> NAME/KEY: X
<222> LOCATION: (102)..(102)
<223> OTHER INFORMATION: K or R
<220> FEATURE:
<221> NAME/KEY: X
<222> LOCATION: (103)..(103)
<223> OTHER INFORMATION: V or L
<220> FEATURE:
<221> NAME/KEY: X
<222> LOCATION: (104)..(104)
<223> OTHER INFORMATION: E or D
<220> FEATURE:
<221> NAME/KEY: X
<222> LOCATION: (106)..(106)
<223> OTHER INFORMATION: K or T

<400> SEQUENCE: 69
```

```
Xaa Thr Gln Ser Xaa Xaa Thr Leu Ser Xaa Ser Pro Gly Xaa Xaa Xaa
1               5                   10                  15

Thr Leu Ser Cys Xaa Ala Xaa Xaa Xaa Xaa Xaa Xaa Xaa Xaa
            20                  25                  30

Trp Tyr Gln Xaa Xaa Xaa Gly Xaa Xaa Pro Xaa Leu Leu Ile Tyr Xaa
                35                  40                  45

Xaa Ser Xaa Arg Ala Xaa Gly Xaa Pro Xaa Arg Phe Ser Xaa Ser Gly
        50                  55                  60

Ser Gly Xaa Xaa Phe Thr Leu Thr Ile Xaa Arg Leu Xaa Xaa Glu Xaa
65                  70                  75                  80

Phe Ala Xaa Tyr Tyr Cys Gln Xaa Xaa Xaa Ser Xaa Xaa Xaa Thr
            85                  90                  95

Phe Gly Xaa Gly Thr Xaa Xaa Xaa Ile Xaa Arg
            100                 105
```

<210> SEQ ID NO 70
<211> LENGTH: 106
<212> TYPE: PRT
<213> ORGANISM: Artificial Sequence
<220> FEATURE:
<223> OTHER INFORMATION: synthetic

<400> SEQUENCE: 70

```
Leu Thr Gln Ser Pro Gly Thr Leu Ser Leu Ser Pro Gly Glu Arg Ala
1               5                   10                  15

Thr Leu Ser Cys Gly Ala Ser Gln Ser Val Ser Asn Ser Tyr Leu Ala
            20                  25                  30

Trp Tyr Gln Gln Lys Pro Gly Leu Ala Pro Arg Leu Leu Ile Tyr Gly
                35                  40                  45

Ala Ser Ser Arg Ala Thr Gly Ile Pro Asp Arg Phe Ser Gly Ser Gly
        50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Pro Leu Thr Phe
            85                  90                  95

Gly Gly Gly Thr Lys Val Glu Ile Lys Arg
            100                 105
```

<210> SEQ ID NO 71
<211> LENGTH: 110
<212> TYPE: PRT
<213> ORGANISM: Artificial Sequence
<220> FEATURE:
<223> OTHER INFORMATION: synthetic

<400> SEQUENCE: 71

```
Leu Thr Gln Pro Ser Ser Val Ser Gly Ala Pro Gly Gln Arg Val Thr
1               5                   10                  15

Ile Ser Cys Thr Gly Ser Ser Asn Ile Gly Ala Arg Tyr Asp Val
            20                  25                  30

His Trp Tyr Gln Gln Leu Pro Gly Thr Ala Pro Lys Leu Leu Ile Tyr
                35                  40                  45

Gly Asn Ser Asn Arg Pro Ser Gly Val Pro Asp Arg Phe Ser Gly Ser
        50                  55                  60

Lys Ser Gly Thr Ser Ala Ser Leu Ala Ile Thr Gly Leu Gln Ala Glu
65                  70                  75                  80

Asp Glu Ala Asp Tyr Tyr Cys Gln Ser Tyr Asp Ser Ser Leu Ser Gly
```

```
                    85                  90                  95

Ser Trp Val Phe Gly Gly Gly Thr Lys Leu Thr Val Leu Gly
            100                 105                 110
```

<210> SEQ ID NO 72
<211> LENGTH: 106
<212> TYPE: PRT
<213> ORGANISM: Artificial Sequence
<220> FEATURE:
<223> OTHER INFORMATION: synthetic

<400> SEQUENCE: 72

```
Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Ser Ser Tyr Leu Ala
            20                  25                  30

Trp Tyr Gln Gln Lys Pro Gly Gln Ala Pro Arg Leu Leu Ile Tyr Gly
        35                  40                  45

Ala Ser Ser Arg Ala Thr Gly Thr Pro Asp Arg Phe Ser Gly Ser Gly
    50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Pro Tyr Thr Phe
                85                  90                  95

Gly Gln Gly Thr Lys Leu Glu Ile Lys Arg
            100                 105
```

<210> SEQ ID NO 73
<211> LENGTH: 110
<212> TYPE: PRT
<213> ORGANISM: Artificial Sequence
<220> FEATURE:
<223> OTHER INFORMATION: synthetic

<400> SEQUENCE: 73

```
Leu Thr Gln Ser Pro Leu Ser Leu Pro Val Thr Leu Gly Gln Pro Ala
1               5                   10                  15

Ser Ile Ser Cys Arg Ser Arg Gln Ser Leu Val Tyr Ser Asp Gly Asn
            20                  25                  30

Thr Tyr Phe Asn Trp Phe His Gln Arg Pro Gly Gln Ser Pro Arg Arg
        35                  40                  45

Leu Ile Tyr Arg Val Ser Asn Arg Asp Ser Gly Val Pro Asp Arg Phe
    50                  55                  60

Ser Gly Ser Gly Ser Gly Thr Asp Phe Thr Leu Thr Ile Ser Arg Val
65                  70                  75                  80

Glu Ala Glu Asp Val Gly Leu Tyr Tyr Cys Met Gln Gly Ser His Trp
                85                  90                  95

Pro Pro Thr Phe Gly Gln Gly Thr Lys Leu Glu Ile Lys Arg
            100                 105                 110
```

<210> SEQ ID NO 74
<211> LENGTH: 108
<212> TYPE: PRT
<213> ORGANISM: Artificial Sequence
<220> FEATURE:
<223> OTHER INFORMATION: synthetic

<400> SEQUENCE: 74

```
Leu Thr Gln Pro Ser Ser Val Ser Gly Thr Pro Gly Gln Arg Val Thr
1               5                   10                  15
```

Ile Ser Cys Ser Gly Gly Ser Ser Asn Ile Gly Arg Asn Thr Val Asp
                20                  25                  30

Trp Tyr Gln Gln Phe Pro Gly Thr Ala Pro Lys Leu Leu Ile Tyr Thr
            35                  40                  45

Asn Asn Gln Arg Pro Ser Gly Val Pro Asp Arg Phe Phe Gly Ser Lys
 50                  55                  60

Ser Gly Thr Ser Ala Ser Leu Ala Ile Ser Gly Leu Gln Ser Ala Asp
 65                  70                  75                  80

Glu Ala Asp Tyr Tyr Cys Ala Thr Trp Asp Asp Asn Leu Asn Gly Ala
                85                  90                  95

Val Phe Gly Gly Gly Thr Gln Val Thr Val Leu Gly
            100                 105

<210> SEQ ID NO 75
<211> LENGTH: 106
<212> TYPE: PRT
<213> ORGANISM: Artificial Sequence
<220> FEATURE:
<223> OTHER INFORMATION: synthetic

<400> SEQUENCE: 75

Leu Thr Gln Ser Pro Gly Thr Leu Ser Leu Ser Pro Gly Glu Arg Ala
1               5                   10                  15

Thr Leu Ser Cys Arg Ala Ser Gln Ser Val Asn Arg Asn Asp Leu Ala
                20                  25                  30

Trp Tyr Gln Gln Lys Pro Gly Gln Ala Pro Arg Leu Leu Ile Tyr Ala
            35                  40                  45

Ala Ser Thr Arg Ala Thr Gly Ile Pro Asp Arg Phe Ser Ala Ser Gly
 50                  55                  60

Ser Gly Thr Asp Phe Thr Leu Thr Ile Ser Arg Leu Glu Pro Glu Asp
 65                  70                  75                  80

Phe Ala Met Tyr Tyr Cys Gln His Tyr Gly Ser Ser Leu Phe Thr Phe
                85                  90                  95

Gly Pro Gly Thr Lys Val Asp Ile Lys Arg
            100                 105

<210> SEQ ID NO 76
<211> LENGTH: 212
<212> TYPE: PRT
<213> ORGANISM: Artificial Sequence
<220> FEATURE:
<223> OTHER INFORMATION: synthetic

<400> SEQUENCE: 76

Leu Thr Gln Ser Pro Gly Thr Leu Ser Leu Ser Pro Gly Glu Arg Ala
1               5                   10                  15

Thr Leu Ser Cys Gly Ala Ser Gln Ser Val Ser Asn Ser Tyr Leu Ala
                20                  25                  30

Trp Tyr Gln Gln Lys Pro Gly Leu Ala Pro Arg Leu Leu Ile Tyr Gly
            35                  40                  45

Ala Ser Ser Arg Ala Thr Gly Ile Pro Asp Arg Phe Ser Gly Ser Gly
 50                  55                  60

Ser Gly Thr Asp Phe Thr Leu Thr Ile Ser Arg Leu Glu Pro Glu Asp
 65                  70                  75                  80

Phe Ala Val Tyr Tyr Cys Gln Gln Tyr Gly Ser Ser Pro Leu Thr Phe
                85                  90                  95

Gly Gly Gly Thr Lys Val Glu Ile Lys Arg Thr Val Ala Ala Pro Ser

```
                100             105             110
Val Phe Ile Phe Pro Ser Asp Glu Gln Leu Lys Ser Gly Thr Ala
            115             120             125

Ser Val Val Cys Leu Leu Asn Asn Phe Tyr Pro Arg Glu Ala Lys Val
        130                 135             140

Gln Trp Lys Val Asp Asn Ala Leu Gln Ser Gly Asn Ser Gln Glu Ser
145                 150             155                 160

Val Thr Glu Gln Asp Ser Lys Asp Ser Thr Tyr Ser Leu Ser Ser Thr
                165             170             175

Leu Thr Leu Ser Lys Ala Asp Tyr Glu Lys His Lys Val Tyr Ala Cys
            180             185             190

Glu Val Thr His Gln Gly Leu Ser Ser Pro Val Thr Lys Ser Phe Asn
        195                 200             205

Arg Gly Glu Cys
    210

<210> SEQ ID NO 77
<211> LENGTH: 215
<212> TYPE: PRT
<213> ORGANISM: Artificial Sequence
<220> FEATURE:
<223> OTHER INFORMATION: synthetic

<400> SEQUENCE: 77

Leu Thr Gln Pro Ser Ser Val Ser Gly Ala Pro Gly Gln Arg Val Thr
1               5                   10                  15

Ile Ser Cys Thr Gly Ser Ser Asn Ile Gly Ala Arg Tyr Asp Val
            20                  25                  30

His Trp Tyr Gln Gln Leu Pro Gly Thr Ala Pro Lys Leu Leu Ile Tyr
            35                  40                  45

Gly Asn Ser Asn Arg Pro Ser Gly Val Pro Asp Arg Phe Ser Gly Ser
    50                  55                  60

Lys Ser Gly Thr Ser Ala Ser Leu Ala Ile Thr Gly Leu Gln Ala Glu
65                  70                  75                  80

Asp Glu Ala Asp Tyr Tyr Cys Gln Ser Tyr Asp Ser Ser Leu Ser Gly
                85                  90                  95

Ser Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Lys
            180                 185                 190

Ser Tyr Ser Cys Gln Val Thr His Glu Gly Ser Thr Val Glu Lys Thr
            195                 200                 205

Val Ala Pro Thr Glu Cys Ser
    210                 215

<210> SEQ ID NO 78
<211> LENGTH: 212
<212> TYPE: PRT
```

<213> ORGANISM: Artificial Sequence
<220> FEATURE:
<223> OTHER INFORMATION: synthetic

<400> SEQUENCE: 78

```
Leu Thr Gln Ser Pro Gly Thr Leu Ser Leu Ser Pro Gly Glu Arg Ala
1               5                   10                  15

Thr Leu Ser Cys Arg Ala Ser Gln Ser Val Ser Ser Ser Tyr Leu Ala
            20                  25                  30

Trp Tyr Gln Gln Lys Pro Gly Gln Ala Pro Arg Leu Leu Ile Tyr Gly
        35                  40                  45

Ala Ser Ser Arg Ala Thr Gly Thr Pro Asp Arg Phe Ser Gly Ser Gly
    50                  55                  60

Ser Gly Thr Asp Phe Thr Leu Thr Ile Ser Arg Leu Glu Pro Glu Asp
65                  70                  75                  80

Phe Ala Val Tyr Tyr Cys Gln Gln Tyr Gly Ser Ser Pro Tyr Thr Phe
                85                  90                  95

Gly Gln Gly Thr Lys Leu Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210
```

<210> SEQ ID NO 79
<211> LENGTH: 216
<212> TYPE: PRT
<213> ORGANISM: Artificial Sequence
<220> FEATURE:
<223> OTHER INFORMATION: synthetic

<400> SEQUENCE: 79

```
Leu Thr Gln Ser Pro Leu Ser Leu Pro Val Thr Leu Gly Gln Pro Ala
1               5                   10                  15

Ser Ile Ser Cys Arg Ser Arg Gln Ser Leu Val Tyr Ser Asp Gly Asn
            20                  25                  30

Thr Tyr Phe Asn Trp Phe His Gln Arg Pro Gly Gln Ser Pro Arg Arg
        35                  40                  45

Leu Ile Tyr Arg Val Ser Asn Arg Asp Ser Gly Val Pro Asp Arg Phe
    50                  55                  60

Ser Gly Ser Gly Ser Gly Thr Asp Phe Thr Leu Thr Ile Ser Arg Val
65                  70                  75                  80

Glu Ala Glu Asp Val Gly Leu Tyr Tyr Cys Met Gln Gly Ser His Trp
                85                  90                  95

Pro Pro Thr Phe Gly Gln Gly Thr Lys Leu Glu Ile Lys Arg Thr Val
            100                 105                 110
```

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 80
<211> LENGTH: 213
<212> TYPE: PRT
<213> ORGANISM: Artificial Sequence
<220> FEATURE:
<223> OTHER INFORMATION: synthetic

<400> SEQUENCE: 80

Leu Thr Gln Pro Ser Ser Val Ser Gly Thr Pro Gly Gln Arg Val Thr
1               5                   10                  15

Ile Ser Cys Ser Gly Gly Ser Ser Asn Ile Gly Arg Asn Thr Val Asp
            20                  25                  30

Trp Tyr Gln Gln Phe Pro Gly Thr Ala Pro Lys Leu Leu Ile Tyr Thr
        35                  40                  45

Asn Asn Gln Arg Pro Ser Gly Val Pro Asp Arg Phe Phe Gly Ser Lys
    50                  55                  60

Ser Gly Thr Ser Ala Ser Leu Ala Ile Ser Gly Leu Gln Ser Ala Asp
65                  70                  75                  80

Glu Ala Asp Tyr Tyr Cys Ala Thr Trp Asp Asp Asn Leu Asn Gly Ala
                85                  90                  95

Val Phe Gly Gly Gly Thr Gln Val Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Val Ser Asp Phe Tyr Pro Gly Ala
    130                 135                 140

Val Thr Val Ala Trp Lys Ala Asp Gly Ser Pro Val Lys Val Gly Val
145                 150                 155                 160

Glu Thr Thr Lys Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Arg Val Thr His Glu Gly Ser Thr Val Glu Lys Thr Val Ala
        195                 200                 205

Pro Ala Glu Cys Ser
    210

<210> SEQ ID NO 81
<211> LENGTH: 212
<212> TYPE: PRT
<213> ORGANISM: Artificial Sequence
<220> FEATURE:

<223> OTHER INFORMATION: synthetic

<400> SEQUENCE: 81

```
Leu Thr Gln Ser Pro Gly Thr Leu Ser Leu Ser Pro Gly Glu Arg Ala
1               5                   10                  15

Thr Leu Ser Cys Arg Ala Ser Gln Ser Val Asn Arg Asn Asp Leu Ala
            20                  25                  30

Trp Tyr Gln Gln Lys Pro Gly Gln Ala Pro Arg Leu Leu Ile Tyr Ala
        35                  40                  45

Ala Ser Thr Arg Ala Thr Gly Ile Pro Asp Arg Phe Ser Ala Ser Gly
    50                  55                  60

Ser Gly Thr Asp Phe Thr Leu Thr Ile Ser Arg Leu Glu Pro Glu Asp
65                  70                  75                  80

Phe Ala Met Tyr Tyr Cys Gln His Tyr Gly Ser Ser Leu Phe Thr Phe
                85                  90                  95

Gly Pro Gly Thr Lys Val Asp Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
210
```

<210> SEQ ID NO 82
<211> LENGTH: 50
<212> TYPE: PRT
<213> ORGANISM: artificial sequence
<220> FEATURE:
<223> OTHER INFORMATION: Ectodomain of Fn14 comprising an alanine substituted for the arginine at a position corresponding to position 58 of human Fn14

<400> SEQUENCE: 82

```
Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Ala Pro
            20                  25                  30

His Ser Asp Phe Cys Leu Gly Cys Ala Ala Ala Pro Pro Ala Pro Phe
        35                  40                  45

Arg Leu
    50
```

FN14-BINDING PROTEINS AND USES THEREOF

RELATED APPLICATION DATA

This application is a U.S. National Phase Entry of International Application No. PCT/AU2015/050658, filed Oct. 23, 2015, which claims priority from Australian Provisional Application No. 2014904235 entitled "Fn14 binding proteins and uses thereof" filed on 23 Oct. 2014, the contents of each of which are incorporated herein by reference in their entirety.

SEQUENCE LISTING

In accordance with 37 CFR 1.52(e)(5), a Sequence Listing in the form of a text file (entitled "2009214-0002 Sequence Listing ST25", created on Apr. 21, 2017, and having a size of 107,300 bytes) is hereby incorporated by reference in its entirety. In the case of any discrepancy between a sequence in the Drawings and a sequence in the Sequence Listing, the sequence in the Drawings is to take precedence.

FIELD

The present invention relates to Fn14-binding proteins comprising antigen binding sites that bind to Fn14 and uses thereof and methods of treating, preventing, diagnosing or prognosing various conditions including wasting disorders, such as cachexia.

BACKGROUND

Fibroblast Growth Factor Inducible 14

Fibroblast growth factor inducible 14 (Fn14, also known as TNF-like weak inducer of apoptosis receptor [Tweak-R] or TNFRSF12A), is a member of the Tumor Necrosis Factor receptor superfamily. Expression of Fn14 is up-regulated by growth factors in vitro and in vivo in response to tissue injury, regeneration, and inflammation. As one of the names for Fn14 suggests, this protein is a receptor for the protein designated Tweak. Tweak binding to Fn14, or constitutive Fn14 overexpression, activates the NFκB signaling pathway, which is known to play an important role in immune and inflammatory processes, oncogenesis, and cancer therapy resistance. This interaction also controls many cellular activities including, proliferation, migration, differentiation, apoptosis, angiogenesis and inflammation. Tweak and Fn14 are also involved in tissue repair and regulation of immune functions and tumor growth. Accordingly, Fn14-mediated signaling is involved in pathways that play important roles in human diseases. Fn14-mediated signaling has been suggested to play a role in numerous diseases, including, cancer, metastasis, immunological disorders (including autoimmune diseases, graft rejection and graft versus host disease, and chronic and acute neurological conditions [including stroke]).

Fn14 is expressed by many non-lymphoid cell types (epithelial, mesenchymal, endothelial cells and neurons), by many tissue progenitor cells, including all progenitor cells of the mesenchymal lineage. This protein is highly inducible by growth factors e.g., in serum, that are encountered in vivo at sites of tissue injuries and/or tissue remodeling. As a consequence, Fn14 expression is relatively low in most healthy tissues, but increased in injured and/or diseased tissues.

Based on the foregoing description, the skilled artisan will be aware that compounds that bind to Fn14 are desirable. These compounds can be used to treat, prevent, diagnose or prognose Fn14-mediated conditions.

SUMMARY

In producing the present disclosure, the inventors sought to produce reagents (e.g. binding proteins and antibodies that bind to Fn14 and can provide a therapeutic benefit).

The inventors have produced human anti-Fn14 Fab fragments. These antibody fragments were affinity matured to nano-molar level. The inventors also reformatted some Fab fragments to whole IgG and compared them functionally to murine anti-human Fn14 antibodies in vitro and in vivo.

The antibodies were shown to interact with a mutant form of Fn14 comprising an alanine in place of the arginine at a position corresponding to amino acid residue 58 of human Fn14 (position 31 of SEQ ID NO: 1).

The antibodies were also shown to prevent cachexia in a mouse model and increase survival rate compared to controls, consistent with a previously identified mouse monoclonal anti-Fn14 antibody.

In one example, the present disclosure provides an isolated or recombinant human Fn14-binding protein comprising an antigen binding domain, wherein the antigen binding domain binds specifically to Fn14 or a cell expressing Fn14. In one example, the antigen binding domain additionally binds to a mutant form of Fn14 comprising an alanine in place of the arginine at a position corresponding to amino acid residue 58 of human Fn14 (position 31 of SEQ ID NO: 1). For example, the antigen binding domain additionally binds to a polypeptide comprising or consisting of a sequence set forth in SEQ ID NO: 82 (optionally with a Hexa-His tag at the N- or C-terminus).

In one example, the present disclosure provides an isolated or recombinant Fn14-binding protein comprising an antigen binding domain, wherein the antigen binding domain binds specifically to Fn14 or a cell expressing Fn14 and wherein the antigen binding domain comprises:

i) a heavy chain variable region ($V_H$) comprising CDRs 1 and 2 in the sequence set forth in SEQ ID NOs:2 or 3; or a sequence of at least 50% identity thereto; or a deimmunized or germlined version thereof; or an affinity matured form thereof; and/or ii) a light chain variable region ($V_L$) comprising CDRs 1, 2 and 3 in the sequence set forth in any one of SEQ ID NOs:4, 5, 6, 7 or 8; or a sequence of at least 50% identity thereto; or a deimmunized or germlined version thereof; or an affinity matured form thereof.

In one example, the present disclosure provides an isolated or recombinant Fn14-binding protein comprising an antigen binding domain of an anti-Fn14 antibody, wherein the antigen binding domain comprises:

i) a $V_H$ comprising CDRs 1 and 2 in the sequence set forth in SEQ ID NOs:2 and 3; or a sequence of at least 50% identity thereto; or a deimmunized or germlined version thereof; or an affinity matured form thereof; and/or ii) a $V_L$ comprising CDRs 1, 2 and 3 in the sequence set forth in any one of SEQ ID NOs:4, 5, 6, 7 or 8; or a sequence of at least 50% identity thereto; or a deimmunized or germlined version thereof; or an affinity matured form thereof.

In one example, the disclosure provides a Fn14-binding protein, wherein the antigen binding domain comprises a $V_H$ comprising CDR3 in the sequence set forth in any one of SEQ ID NOs:9 to 23; or a sequence of at least 50% identity thereto; or a deimmunized or germlined version thereof; or an affinity matured form thereof.

In one example, the disclosure provides a Fn14-binding protein, wherein the antigen binding domain comprises a $V_L$ comprising CDR1 in the sequence set forth in SEQ ID NO:24; or a sequence of at least 45%, or at least 50%, or at least 54%, or at least 58%, or at least 66%, or at least 75%, or at least 83%, or at least 91% identity thereto; or a deimmunized or germlined version thereof; or an affinity matured form thereof. In one example, the antigen binding domain comprises a $V_L$ comprising CDR1 in the sequence set forth in SEQ ID NO:24; or a sequence of at least 45% identity thereto. In one example, the antigen binding domain comprises a $V_L$ comprising CDR1 in the sequence set forth in SEQ ID NO:24; or a sequence of at least 50% identity thereto. In one example, the antigen binding domain comprises a $V_L$ comprising CDR1 in the sequence set forth in SEQ ID NO:24; or a sequence of at least 54% identity thereto. In one example, the antigen binding domain comprises a $V_L$ comprising CDR1 in the sequence set forth in SEQ ID NO:24; or a sequence of at least 58% identity thereto. In one example, the antigen binding domain comprises a $V_L$ comprising CDR1 in the sequence set forth in SEQ ID NO:24; or a sequence of at least 66% identity thereto. In one example, the antigen binding domain comprises a $V_L$ comprising CDR1 in the sequence set forth in SEQ ID NO:24; or a sequence of at least 75% identity thereto. In one example, the antigen binding domain comprises a $V_L$ comprising CDR1 in the sequence set forth in SEQ ID NO:24; or a sequence of at least 83% identity thereto. In one example, the antigen binding domain comprises a $V_L$ comprising CDR1 in the sequence set forth in SEQ ID NO:24; or a sequence of at least 91% identity thereto.

In one example, the antigen binding domain comprises a $V_L$ comprising CDR2 in the sequence set forth in SEQ ID NO:24; or a sequence of at least 70%, or at least 85% identity thereto; or a deimmunized or germlined version thereof; or an affinity matured form thereof. In one example, the antigen binding domain comprises a $V_L$ comprising CDR2 in the sequence set forth in SEQ ID NO:24; or a sequence of at least 70%, identity thereto. In one example, the antigen binding domain comprises a $V_L$ comprising CDR2 in the sequence set forth in SEQ ID NO:24; or a sequence of at least 85%, identity thereto.

In one example, the antigen binding domain comprises a $V_L$ comprising CDR3 in the sequence set forth in SEQ ID NO:24; or a sequence of at least 55%, or at least 66%, or at least 77%, or at least 88% identity thereto; or a deimmunized or germlined version thereof; or an affinity matured form thereof. In one example, the antigen binding domain, comprises a $V_L$ comprising CDR3 in the sequence set forth in SEQ ID NO:24; or a sequence of at least 55% identity thereto. In one example, the antigen binding domain, comprises a $V_L$ comprising CDR3 in the sequence set forth in SEQ ID NO:24; or a sequence of at least 66% identity thereto. In one example, the antigen binding domain, comprises a $V_L$ comprising CDR3 in the sequence set forth in SEQ ID NO:24; or a sequence of at least 77% identity thereto. In one example, the antigen binding domain comprises a $V_L$ comprising CDR3 in the sequence set forth in SEQ ID NO:24; or a sequence of at least 88% identity thereto.

In one example, the antigen binding domain comprises a $V_L$ comprising the sequence set forth in SEQ ID NO:24; or a sequence of at least 55%, or at least 68%, or at least 83%, or at least 84%, or at least 85%, or at least 86%, or at least 88%, or at least 89%, or at least 90%, or at least 91%, or at least 92%, or at least 94%, or at least 95%, or at least 97% identity thereto; or a deimmunized or germlined version thereof; or an affinity matured form thereof. In one example, the antigen binding domain, comprises a $V_L$ in the sequence set forth in SEQ ID NO:24; or a sequence of at least 55% identity thereto. In one example, the antigen binding domain, comprises a VL in the sequence set forth in SEQ ID NO:24; or a sequence of at least 68% identity thereto. In one example, the antigen binding domain, comprises a VL in the sequence set forth in SEQ ID NO:24; or a sequence of at least 83% identity thereto. In one example, the antigen binding domain, comprises a VL in the sequence set forth in SEQ ID NO:24; or a sequence of at least 85% identity thereto. In one example, the antigen binding domain, comprises a VL in the sequence set forth in SEQ ID NO:24; or a sequence of at least 85% identity thereto. In one example, the antigen binding domain, comprises a VL in the sequence set forth in SEQ ID NO:24; or a sequence of at least 86% identity thereto. In one example, the antigen binding domain, comprises a VL in the sequence set forth in SEQ ID NO:24; or a sequence of at least 88% identity thereto. In one example, the antigen binding domain, comprises a VL in the sequence set forth in SEQ ID NO:24; or a sequence of at least 89% identity thereto. In one example, the antigen binding domain, comprises a VL in the sequence set forth in SEQ ID NO:24; or a sequence of at least 90% identity thereto. In one example, the antigen binding domain, comprises a VL in the sequence set forth in SEQ ID NO:24; or a sequence of at least 91% identity thereto. In one example, the antigen binding domain, comprises a VL in the sequence set forth in SEQ ID NO:24; or a sequence of at least 92% identity thereto. In one example, the antigen binding domain, comprises a VL in the sequence set forth in SEQ ID NO:24; or a sequence of at least 94% identity thereto. In one example, the antigen binding domain, comprises a VL in the sequence set forth in SEQ ID NO:24; or a sequence of at least 95% identity thereto. In one example, the antigen binding domain, comprises a VL in the sequence set forth in SEQ ID NO:24; or a sequence of at least 97% identity thereto.

In one example, the Fn14-binding protein binds specifically to an epitope in Fn14 comprising residues contained within the sequence set forth in SEQ ID NO:1.

In one example, the Fn14-binding protein additionally binds to a mutant form of human Fn14 comprising an alanine in place of the arginine at a position corresponding to amino acid residue 58 of human Fn14 (position 31 of SEQ ID NO: 1). For example, the antigen binding domain additionally binds to a polypeptide comprising or consisting of a sequence set forth in SEQ ID NO: 82 (optionally with a Hexa-His tag at the N- or C-terminus).

Described herein according to any example Fn14 is human Fn14, for example comprising the sequence set forth in SEQ ID NO:1 or a protein having at least 50%, or at least 60%, or at least 70%, or at least 80%, or at least 90%, or at least 95%, or at least 99% identity thereto, or is identical thereto.

In one example, the Fn14-binding protein binds specifically to the Fn14 ectodomain as set forth in residues 1 to 50 of Seq ID NO:1.

In one example, the Fn14-binding protein when assessed as a Fab binds to Fn14 with a $K_D$ of between of 0.1 and 900 nM, or between 1 and 500 nM, or between 2 and 400 nM, or between 3 and 300 nM, or between 5 and 230 nM, or between 1 and 10 nM, or between 2 and 8 nM, or between 3 and 7 nM, or between 4 and 6 nM, or between 10 and 1000 nM, or between 20 and 900 nM, or between 30 and 800 nM, or between 40 and 700 nM, or between 50 and 500 nM, or between 100 and 400 nM, or between 150 and 300 nM, or between 200 and 250 nM. In one example, the Fn14-binding protein when assessed as a Fab binds to Fn14 with a $K_D$ of between 5 and 230 nM. In one example, the Fn14-binding protein when assessed as a Fab binds to Fn14 with a $K_D$ of between 5 and 221 nM. In one example, the Fn14-binding protein when assessed as a Fab binds to Fn14 with a $K_D$ of between 4 and 6 nM. In one example, the Fn14-binding protein when assessed as a Fab binds to Fn14 with a $K_D$ of between 200 and 250 nM. In one example, the Fn14-binding protein when assessed as a Fab binds to Fn14 with a $K_D$ of about 220 nM. In one example, the Fn14-binding protein when assessed as a Fab binds to Fn14 with a $K_D$ of about 5.66 nM. In one example, the Fn14-binding protein when assessed as a Fab binds to Fn14 with a $K_D$ of about 5.42 nM. In one example, the Fn14-binding protein when assessed as a Fab binds to Fn14 with a $K_D$ of about 5.91 nM.

In one example, the Fn14-binding protein when assessed as a Fab binds to Fn14 with a Kd ($s^{-1}$) of between $6 \times 10^{-4}$ to $4 \times 10^{-3}$, or between $7 \times 10^{-4}$ to $3 \times 10^{-3}$e, or between $8 \times 10^{-4}$ to $2.1 \times 10^{-3}$. In one example, the Fn14-binding protein when assessed as a Fab binds to Fn14 with a Kd ($s^{-1}$) of at least $2. \times 10^{-3}$. In one example, the Fn14-binding protein when assessed as a Fab binds to Fn14 with a Kd ($s^{-1}$) of at least $8 \times 10^{-4}$. In one example, the Fn14-binding protein when assessed as a Fab binds to Fn14 with a Kd ($s^{-1}$) of at least $9 \times 10^{-4}$.

In one example, the Fn14-binding protein binds to a polypeptide of SEQ ID NO:1 with greater affinity, for example, at least 20, or at least 40, or at least 60, or at least 80, or at least 100, or at least 150, or at least 200, or at least 250, or at least 300, or at least 350, or at least 400, of at least 450, or at least 500, or at least 550, or at least 600, or at least 650, or at least 700, or at least 750, or at least 800, or at least 850, or at least 900, or at least 950, or at least 1000 fold greater affinity than another antigen. In one example, the other antigen is CD38-Fc, Relt-Fc, PI16-Fc, Fc, AMA1-His, MSP2-His, 5 GB IgG1, BSA and/or IGF.

In one example, the antigen binding domain comprises a $V_H$ sequence set forth in any one of SEQ ID NOs:9 to 23; or a sequence of at least 50% identity thereto; or a deimmunized or germlined version thereof; or an affinity matured form thereof.

In one example, the antigen binding domain comprises a $V_L$ sequence set forth in SEQ ID NO:69; or a sequence of at least 50% identity thereto; or a deimmunized or germlined version thereof; or an affinity matured form thereof.

In one example, the antigen binding domain comprises a $V_L$ sequence set forth in any one of SEQ ID NOs:24 to 48 or 70 to 75; or a sequence of at least 50% identity thereto; or a deimmunized or germlined version thereof; or an affinity matured form thereof.

In one example, the antigen binding domain comprises:
 i) a $V_H$ comprising a sequence set forth in any one of SEQ ID NOs:9 to 23; or a sequence of at least 50% identity thereto; or a deimmunized or germlined version thereof; or an affinity matured form thereof; and
 ii) a $V_L$ comprising a sequence set forth in any one of SEQ ID NOs:24 to 48, 69 or 70 to 75; or a sequence of at least 50% identity thereto; or a deimmunized or germlined version thereof; or an affinity matured form thereof.

In one example, the antigen binding domain comprises:
 i) a $V_H$ comprising a sequence set forth in SEQ ID NO:9 and a $V_L$ comprising a sequence set forth in SEQ ID NO:24;
 ii) a $V_H$ comprising a sequence set forth in SEQ ID NO:10 and a $V_L$ comprising a sequence set forth in SEQ ID NO:25;
 iii) a $V_H$ comprising a sequence set forth in SEQ ID NO:11 and a $V_L$ comprising a sequence set forth in SEQ ID NO:26;
 iv) a $V_H$ comprising a sequence set forth in SEQ ID NO:12 and a $V_L$ comprising a sequence set forth in SEQ ID NO:27;
 v) a $V_H$ comprising a sequence set forth in SEQ ID NO:14 and a $V_L$ comprising a sequence set forth in SEQ ID NO:28;
 vi) a $V_H$ comprising a sequence set forth in SEQ ID NO:16 and a $V_L$ comprising a sequence set forth in SEQ ID NO:29;
 vii) a $V_H$ comprising a sequence set forth in SEQ ID NO:9 and a $V_L$ comprising a sequence set forth in SEQ ID NO:30;
 viii) a $V_H$ comprising a sequence set forth in SEQ ID NO:9 and a $V_L$ comprising a sequence set forth in SEQ ID NO:31;
 ix) a $V_H$ comprising a sequence set forth in SEQ ID NO:9 and a $V_L$ comprising a sequence set forth in SEQ ID NO:32;
 x) a $V_H$ comprising a sequence set forth in SEQ ID NO:9 and a $V_L$ comprising a sequence set forth in SEQ ID NO:33;
 xii) a $V_H$ comprising a sequence set forth in SEQ ID NO:9 and a $V_L$ comprising a sequence set forth in SEQ ID NO:34;
 xiii) a $V_H$ comprising a sequence set forth in SEQ ID NO:9 and a $V_L$ comprising a sequence set forth in SEQ ID NO:35;
 xiv) a $V_H$ comprising a sequence set forth in SEQ ID NO:9 and a $V_L$ comprising a sequence set forth in SEQ ID NO:36;
 xv) a $V_H$ comprising a sequence set forth in SEQ ID NO:9 and a $V_L$ comprising a sequence set forth in SEQ ID NO:37;
 xvi) a $V_H$ comprising a sequence set forth in SEQ ID NO:9 and a $V_L$ comprising a sequence set forth in SEQ ID NO:38;
 xvii) a $V_H$ comprising a sequence set forth in SEQ ID NO:9 and a $V_L$ comprising a sequence set forth in SEQ ID NO:39;
 xviii) a $V_H$ comprising a sequence set forth in SEQ ID NO:9 and a $V_L$ comprising a sequence set forth in SEQ ID NO:40;
 xix) a $V_H$ comprising a sequence set forth in SEQ ID NO:9 and a $V_L$ comprising a sequence set forth in SEQ ID NO:41;
 xx) a $V_H$ comprising a sequence set forth in SEQ ID NO:9 and a $V_L$ comprising a sequence set forth in SEQ ID NO:42;
 xxi) a $V_H$ comprising a sequence set forth in SEQ ID NO:9 and a $V_L$ comprising a sequence set forth in SEQ ID NO:43;
 xxii) a $V_H$ comprising a sequence set forth in SEQ ID NO:9 and a $V_L$ comprising a sequence set forth in SEQ ID NO:44;
 xxiii) a $V_H$ comprising a sequence set forth in SEQ ID NO:9 and a $V_L$ comprising a sequence set forth in SEQ ID NO:45;
 xxiv) a $V_H$ comprising a sequence set forth in SEQ ID NO:9 and a $V_L$ comprising a sequence set forth in SEQ ID NO:46;
 xxv) a $V_H$ comprising a sequence set forth in SEQ ID NO:9 and a $V_L$ comprising a sequence set forth in SEQ ID NO:47;
 xxvi) a $V_H$ comprising a sequence set forth in SEQ ID NO:9 and a $V_L$ comprising a sequence set forth in SEQ ID NO:48;
 xxvii) a $V_H$ comprising a sequence set forth in SEQ ID NO:9 and a $V_L$ comprising a sequence set forth in SEQ ID NO:70;

xxviii) a $V_H$ comprising a sequence set forth in SEQ ID NO:9 and a $V_L$ comprising a sequence set forth in SEQ ID NO:71;

xxix) a $V_H$ comprising a sequence set forth in SEQ ID NO:9 and a $V_L$ comprising a sequence set forth in SEQ ID NO:72;

xxx) a $V_H$ comprising a sequence set forth in SEQ ID NO:9 and a $V_L$ comprising a sequence set forth in SEQ ID NO:73;

xxxi) a $V_H$ comprising a sequence set forth in SEQ ID NO:9 and a $V_L$ comprising a sequence set forth in SEQ ID NO:74;

xxxii) a $V_H$ comprising a sequence set forth in SEQ ID NO:9 and a $V_L$ comprising a sequence set forth in SEQ ID NO:75.

In one example, the antigen binding domain comprises a $V_H$ comprising a sequence set forth in SEQ ID NO:9 and a $V_L$ comprising a sequence set forth in any one of SEQ ID NOs:24 to 48 or 70 to 75.

In one example, the antigen binding domain comprises a $V_L$ comprising CDRs, 1, 2 and 3 set forth in any of SEQ ID NOs: 26, 45, 46, 48, 71, 73 or 74; or a sequence of at least 50% identity thereto; or a deimmunized or germlined version thereof; or an affinity matured form thereof.

In one example, the present disclosure provides a Fn14-binding protein, wherein the antigen binding domain comprises a $V_L$ comprising a sequence set forth in any one of SEQ ID NOs: 26, 45, 46, 48, 71, 73 or 74; or a sequence of at least 50% identity thereto; or a deimmunized or germlined version thereof; or an affinity matured form thereof.

In one example, the present disclosure provides a Fn14-binding protein, wherein the antigen binding domain comprises a heavy chain set forth in SEQ ID NO:68; or a sequence of at least 50% identity thereto; or a deimmunized or germlined version thereof; or an affinity matured form thereof.

In one example, the present disclosure provides a Fn14-binding protein, wherein the antigen binding domain comprises the light chain sequence, set forth in any one of SEQ ID NOs:49 to 67 or 76 to 81; or a sequence of at least 50% identity thereto; or a deimmunized or germlined version thereof; or an affinity matured form thereof.

In one example, the present disclosure provides a Fn14-binding protein, wherein the $V_H$ and the $V_L$ are in a single polypeptide chain and the Fn14-binding protein is:
i) a single chain Fv fragment (scFv);
ii) a dimeric scFv (di-scFV);
iii) at least one of i) and/or ii) linked to a heavy chain constant region or an Fc or a heavy chain constant domain ($C_H$) 2 and/or $C_H$3; or
iv) at least one of i) and/or ii) linked to a protein that binds to an immune effector cell; or wherein the $V_L$ and $V_H$ are in separate polypeptide chains and the Fn14-binding protein is:
i) a diabody;
ii) a triabody;
iii) a tetrabody;
iv) a Fab;
v) a F(ab')2;
vi) a Fv;
vii) at least one of i) to vi) linked to a heavy chain constant region or an Fc or a heavy chain constant domain ($C_H$)2 and/or $C_H$3;
viii) at least one of i) to vi) linked to a protein that binds to an immune effector cell; or
ix) an antibody. In one example, the present disclosure provides an anti-Fn14 antibody wherein the antigen binding domain comprises a $V_H$ sequence set forth in any one of SEQ ID NOs:9 to 23; or a sequence of at least 50% identity thereto; or a deimmunized or germlined version thereof; or an affinity matured form thereof.

In one example, the present disclosure provides an anti-Fn14 antibody wherein the antigen binding domain comprises the $V_L$ sequence set forth in SEQ ID NO:69; or a sequence of at least 50% identity thereto; or a deimmunized or germlined version thereof; or an affinity matured form thereof. In one example, the present disclosure provides an anti-Fn14 antibody wherein the antigen binding domain comprises the $V_L$ sequence set forth in any one of SEQ ID NOs:24 to 48 or 70 to 75; or a sequence of at least 50% identity thereto; or a deimmunized or germlined version thereof; or an affinity matured form thereof.

In one example, the present disclosure provides an anti-Fn14 antibody wherein the antigen binding domain comprises the $V_L$ sequence set forth in SEQ ID NO:24; or a sequence of at least 68%, or at least 80%, or at least 83%, or at least 84%, or at least 85%, or at least 86%, or at least 88%, or at least 89% or at least 90%, or at least 91% or at least 92%, or at least 93%, or at least 94%, or at least 95%, or at least 96%, or at least 97% identity thereto; or a deimmunized or germlined version thereof; or an affinity matured form thereof. In one example, the antigen binding domain comprises the $V_L$ sequence set forth in SEQ ID NO:24; or a sequence of at least 63% identity thereto. In one example, the antigen binding domain comprises the $V_L$ sequence set forth in SEQ ID NO:24; or a sequence of at least 80% identity thereto. In one example, the antigen binding domain comprises the $V_L$ sequence set forth in SEQ ID NO:24; or a sequence of at least 83% identity thereto. In one example, the antigen binding domain comprises the $V_L$ sequence set forth in SEQ ID NO:24; or a sequence of at least 84% identity thereto. In one example, the antigen binding domain comprises the $V_L$ sequence set forth in SEQ ID NO:24; or a sequence of at least 85% identity thereto. In one example, the antigen binding domain comprises the $V_L$ sequence set forth in SEQ ID NO:24; or a sequence of at least 86% identity thereto. In one example, the antigen binding domain comprises the $V_L$ sequence set forth in SEQ ID NO:24; or a sequence of at least 88% identity thereto. In one example, the antigen binding domain comprises the $V_L$ sequence set forth in SEQ ID NO:24; or a sequence of at least 90% identity thereto. In one example, the antigen binding domain comprises the $V_L$ sequence set forth in SEQ ID NO:24; or a sequence of at least 91% identity thereto. In one example, the antigen binding domain comprises the $V_L$ sequence set forth in SEQ ID NO:24; or a sequence of at least 92% identity thereto. In one example, the antigen binding domain comprises the $V_L$ sequence set forth in SEQ ID NO:24; or a sequence of at least 93% identity thereto. In one example, the antigen binding domain comprises the $V_L$ sequence set forth in SEQ ID NO:24; or a sequence of at least 94% identity thereto. In one example, the antigen binding domain comprises the $V_L$ sequence set forth in SEQ ID NO:24; or a sequence of at least 95% identity thereto. In one example, the antigen binding domain comprises the $V_L$ sequence set forth in SEQ ID NO:24; or a sequence of at least 96% identity thereto. In one example, the antigen binding domain comprises the $V_L$ sequence set forth in SEQ ID NO:24; or a sequence of at least 97% identity thereto.

In one example, the present disclosure provides an anti-Fn14 antibody wherein the antigen binding domain comprises:
i) a $V_H$ comprising a sequence set forth in any one of SEQ ID NOs:9 to 23; or a sequence of at least 50% identity thereto; or a deimmunized or germlined version thereof; or an affinity matured form thereof; and ii) a $V_L$ comprising a sequence set forth in any one of SEQ ID NOs:24 to 48, 69 or 70 to 75; or a sequence of at least 50% identity thereto; or a deimmunized or germlined version thereof; or an affinity matured form thereof.

In one example, the present disclosure provides an anti-Fn14 antibody, the antibody comprising any one of the following:

i) a $V_H$ comprising a sequence set forth in SEQ ID NO:9 and a $V_L$ comprising a sequence set forth in SEQ ID NO:24;

ii) a $V_H$ comprising a sequence set forth in SEQ ID NO:10 and a $V_L$ comprising a sequence set forth in SEQ ID NO:25;

iii) a $V_H$ comprising a sequence set forth in SEQ ID NO:11 and a $V_L$ comprising a sequence set forth in SEQ ID NO:26;

iv) a $V_H$ comprising a sequence set forth in SEQ ID NO:12 and a $V_L$ comprising a sequence set forth in SEQ ID NO:27;

v) a $V_H$ comprising a sequence set forth in SEQ ID NO:14 and a $V_L$ comprising a sequence set forth in SEQ ID NO:28;

vi) a $V_H$ comprising a sequence set forth in SEQ ID NO:16 and a $V_L$ comprising a sequence set forth in SEQ ID NO:29;

vii) a $V_H$ comprising a sequence set forth in SEQ ID NO:9 and a VL comprising a sequence set forth in SEQ ID NO:30;

viii) a $V_H$ comprising a sequence set forth in SEQ ID NO:9 and a $V_L$ comprising a sequence set forth in SEQ ID NO:31;

ix) a $V_H$ comprising a sequence set forth in SEQ ID NO:9 and a $V_L$ comprising a sequence set forth in SEQ ID NO:32;

x) a $V_H$ comprising a sequence set forth in SEQ ID NO:9 and a $V_L$ comprising a sequence set forth in SEQ ID NO:33;

xii) a $V_H$ comprising a sequence set forth in SEQ ID NO:9 and a $V_L$ comprising a sequence set forth in SEQ ID NO:34;

xiii) a $V_H$ comprising a sequence set forth in SEQ ID NO:9 and a $V_L$ comprising a sequence set forth in SEQ ID NO:35;

xiv) a $V_H$ comprising a sequence set forth in SEQ ID NO:9 and a $V_L$ comprising a sequence set forth in SEQ ID NO:36;

xv) a $V_H$ comprising a sequence set forth in SEQ ID NO:9 and a $V_L$ comprising a sequence set forth in SEQ ID NO:37;

xvi) a $V_H$ comprising a sequence set forth in SEQ ID NO:9 and a $V_L$ comprising a sequence set forth in SEQ ID NO:38;

xvii) a $V_H$ comprising a sequence set forth in SEQ ID NO:9 and a $V_L$ comprising a sequence set forth in SEQ ID NO:39;

xviii) a $V_H$ comprising a sequence set forth in SEQ ID NO:9 and a $V_L$ comprising a sequence set forth in SEQ ID NO:40;

xix) a $V_H$ comprising a sequence set forth in SEQ ID NO:9 and a $V_L$ comprising a sequence set forth in SEQ ID NO:41;

xx) a $V_H$ comprising a sequence set forth in SEQ ID NO:9 and a $V_L$ comprising a sequence set forth in SEQ ID NO:42;

xxi) a $V_H$ comprising a sequence set forth in SEQ ID NO:9 and a $V_L$ comprising a sequence set forth in SEQ ID NO:43;

xxii) a $V_H$ comprising a sequence set forth in SEQ ID NO:9 and a $V_L$ comprising a sequence set forth in SEQ ID NO:44;

xxiii) a $V_H$ comprising a sequence set forth in SEQ ID NO:9 and a $V_L$ comprising a sequence set forth in SEQ ID NO:45;

xxiv) a $V_H$ comprising a sequence set forth in SEQ ID NO:9 and a $V_L$ comprising a sequence set forth in SEQ ID NO:46;

xxv) a $V_H$ comprising a sequence set forth in SEQ ID NO:9 and a $V_L$ comprising a sequence set forth in SEQ ID NO:47;

xxvi) a $V_H$ comprising a sequence set forth in SEQ ID NO:9 and a $V_L$ comprising a sequence set forth in SEQ ID NO:48;

xxvii) a $V_H$ comprising a sequence set forth in SEQ ID NO:9 and a $V_L$ comprising a sequence set forth in SEQ ID NO:70;

xxviii) a $V_H$ comprising a sequence set forth in SEQ ID NO:9 and a $V_L$ comprising a sequence set forth in SEQ ID NO:71;

xxix) a $V_H$ comprising a sequence set forth in SEQ ID NO:9 and a $V_L$ comprising a sequence set forth in SEQ ID NO:72;

xxx) a $V_H$ comprising a sequence set forth in SEQ ID NO:9 and a $V_L$ comprising a sequence set forth in SEQ ID NO:73;

xxxi) a $V_H$ comprising a sequence set forth in SEQ ID NO:9 and a $V_L$ comprising a sequence set forth in SEQ ID NO:74;

xxxii) a $V_H$ comprising a sequence set forth in SEQ ID NO:9 and a $V_L$ comprising a sequence set forth in SEQ ID NO:75.

In one example, the present disclosure provides an anti-Fn14 antibody, the antibody comprising a $V_H$ comprising a sequence set forth in SEQ ID NO:9 and a $V_L$ comprising a sequence set forth in any one of SEQ ID NOs:24 to 48 or 70 to 75.

In one example, the present disclosure provides an anti-Fn14 antibody, the antibody comprising a $V_H$ comprising a sequence set forth in SEQ ID NO:11; or a sequence of at least 50% identity thereto; or a deimmunized or germlined version thereof; or an affinity matured form thereof; and a $V_L$ comprising a sequence set forth in SEQ ID NO:26; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:45; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9 or a sequence of at least 50% identity thereto; or a deimmunized or germlined version thereof; or an affinity matured form thereof; and a $V_L$ comprising a sequence set forth in SEQ ID NO:46; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:48; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:24; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:30; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:31; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:32; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:41; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:42; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:43; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:44; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:45; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:46; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:47; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:48; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:70; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:71; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:72; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:73; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:74; or a sequence of at least 50% identity thereto; or a deimmunized or germlined version thereof; or an affinity matured form thereof.

In one example, the present disclosure provides an anti-Fn14 antibody, the antibody comprising a $V_H$ comprising a sequence set forth in SEQ ID NO:9; or a sequence of at least 50% identity thereto; or a deimmunized or germlined version thereof; or an affinity matured form thereof; and a $V_L$ comprising a sequence set forth in SEQ ID NO:75; or a sequence of at least 50% identity thereto; or a deimmunized or germlined version thereof; or an affinity matured form thereof.

In one example, the present disclosure provides an anti-Fn14 antibody, the antibody comprising any one of the following:

i) a heavy chain comprising a sequence set forth in SEQ ID NO:68 and a light chain comprising a sequence set forth in SEQ ID NO:49;

ii) a heavy chain comprising a sequence set forth in SEQ ID NO:68 and a light chain comprising a sequence set forth in SEQ ID NO:50;

iii) a heavy chain comprising a sequence set forth in SEQ ID NO:68 and a light chain comprising a sequence set forth in SEQ ID NO:51;

iv) a heavy chain comprising a sequence set forth in SEQ ID NO:68 and a light chain comprising a sequence set forth in SEQ ID NO:52;

v) a heavy chain comprising a sequence set forth in SEQ ID NO:68 and a light chain comprising a sequence set forth in SEQ ID NO:53;

vi) a heavy chain comprising a sequence set forth in SEQ ID NO:68 and a light chain comprising a sequence set forth in SEQ ID NO:54;

vii) a heavy chain comprising a sequence set forth in SEQ ID NO:68 and a light chain comprising a sequence set forth in SEQ ID NO:55;

viii) a heavy chain comprising a sequence set forth in SEQ ID NO:68 and a light chain comprising a sequence set forth in SEQ ID NO:56;

ix) a heavy chain comprising a sequence set forth in SEQ ID NO:68 and a light chain comprising a sequence set forth in SEQ ID NO:57;

x) a heavy chain comprising a sequence set forth in SEQ ID NO:68 and a light chain comprising a sequence set forth in SEQ ID NO:58;

xi) a heavy chain comprising a sequence set forth in SEQ ID NO:68 and a light chain comprising a sequence set forth in SEQ ID NO:59;

xii) a heavy chain comprising a sequence set forth in SEQ ID NO:68 and a light chain comprising a sequence set forth in SEQ ID NO:60;

xiii) a heavy chain comprising a sequence set forth in SEQ ID NO:68 and a light chain comprising a sequence set forth in SEQ ID NO:61;

xiv) a heavy chain comprising a sequence set forth in SEQ ID NO:68 and a light chain comprising a sequence set forth in SEQ ID NO:62;

xv) a heavy chain comprising a sequence set forth in SEQ ID NO:68 and a light chain comprising a sequence set forth in SEQ ID NO:63;

xvi) a heavy chain comprising a sequence set forth in SEQ ID NO:68 and a light chain comprising a sequence set forth in SEQ ID NO:64;

xvii) a heavy chain comprising a sequence set forth in SEQ ID NO:68 and a light chain comprising a sequence set forth in SEQ ID NO:65;

xviii) a heavy chain comprising a sequence set forth in SEQ ID NO:68 and a light chain comprising a sequence set forth in SEQ ID NO:66;

xix) a heavy chain comprising a sequence set forth in SEQ ID NO:68 and a light chain comprising a sequence set forth in SEQ ID NO:67;

xx) a heavy chain comprising a sequence set forth in SEQ ID NO:68 and a light chain comprising a sequence set forth in SEQ ID NO:76;

xxi) a heavy chain comprising a sequence set forth in SEQ ID NO:68 and a light chain comprising a sequence set forth in SEQ ID NO:77;

xxii) a heavy chain comprising a sequence set forth in SEQ ID NO:68 and a light chain comprising a sequence set forth in SEQ ID NO:78;

xxiii) a heavy chain comprising a sequence set forth in SEQ ID NO:68 and a light chain comprising a sequence set forth in SEQ ID NO:79;

xxiv) a heavy chain comprising a sequence set forth in SEQ ID NO:68 and a light chain comprising a sequence set forth in SEQ ID NO:80;

xxv) a heavy chain comprising a sequence set forth in SEQ ID NO:68 and a light chain comprising a sequence set forth in SEQ ID NO:81.

In one example, the present disclosure provides an anti-Fn14 antibody, the antibody comprising a heavy chain comprising a sequence set for in SEQ ID NO:68; or a deimmunized or germlined version thereof; or an affinity matured form thereof; and a light chain comprising a sequence set forth in any one of SEQ ID NOs:49 to 67 or 76 to 81; or a deimmunized or germlined version thereof; or an affinity matured form thereof.

In one example, the present disclosure provides an anti-Fn14 antibody, the antibody comprising a heavy chain comprising a sequence set forth in SEQ ID NO:68 and a light chain comprising a sequence set forth in SEQ ID NO:65.

In one example, the present disclosure provides an anti-Fn14 antibody, the antibody comprising a heavy chain comprising a sequence set forth in SEQ ID NO:68 and a light chain comprising a sequence set forth in SEQ ID NO:66.

In one example, the present disclosure provides a conjugate comprising the Fn14-binding protein as described herein according to any example, or an anti-Fn14 antibody described herein according to any example, conjugated to a compound. In one example, the compound is selected from the group consisting from; a radioisotope, a detectable label, a therapeutic compound, a colloid a toxin, a nucleic acid, a peptide, a protein, a compound that increases the half-life of the protein in a subject and mixtures thereof.

In one example, the present disclosure provides a composition. In one example, the composition comprises a Fn14-binding protein, or an anti-Fn14 antibody, or a conjugate as described herein according to any example, and a suitable carrier. In one example, the carrier is pharmaceutically acceptable.

In one example, the present disclosure provides a method for treating or preventing an Fn14-mediated condition in a subject. In one example, the method comprising administering to a subject a Fn14-binding protein, or an anti-Fn14 antibody, or a conjugate, or a composition, or a pharmaceutical composition described herein according to any example.

In one example, the Fn14-mediated condition is cancer, metastasis, excessive vascularization or angiogenesis, an autoimmune disease, an inflammatory disease, a neurodegenerative disease, a wasting disorder, a cardiovascular disease or ischemia.

In one example, the Fn14-mediated condition is an inflammatory disease or an autoimmune disease. In one example, the condition is a connective tissue disease (including inflammatory arthritis, such as rheumatoid arthritis, psoriatic arthritis, reactive arthritis or gout), lupus (including systemic lupus erythematosus), type 1 diabetes, multiple sclerosis, vasculitis (including Wegener's granulomatosis and Henoch Schonlein Syndrome), nephritis (including glomerulonephritis and pneumonitis), atherosclerosis or inflammation of the eye (including uveitis). In one example, the condition is cardiovascular disease. In one example, the Fn14-mediated condition is selected from graft versus host disease, cardiac allograft vasculopathy, intramyocardial infarction, ischemic reperfusion injury, connective tissue disease (such as rheumatoid arthritis) or scleroderma. In one example, the Fn14-mediated condition is cancer. In one example, the Fn14-mediate condition is a wasting disorder. In one example, the wasting disorder is cachexia. In one example, the Fn14-mediated condition is cancer and the method reduces or prevents invasiveness of the cancer into tissue of a subject or reduces or prevents metastasis of the cancer.

In one example, the present disclosure provides a method of treating or preventing a wasting disorder which is associated with a condition, the method comprising administering to a subject a Fn14-binding protein, or an anti-Fn14 antibody, or a conjugate, or a composition of the present disclosure to a subject. In one example, the wasting condition is cachexia. For example, the cachexia is cancer cachexia.

In one example, the Fn14-binding protein or anti-Fn14 antibody comprises a $V_H$ comprising a sequence set forth in SEQ ID NO:9 or comprising the CDRs of the $V_H$ and a $V_L$ comprising a sequence set forth in SEQ ID NO:42 or comprising the CDRs of the $V_L$.

In one example, the Fn14-binding protein or anti-Fn14 antibody comprises a $V_H$ comprising a sequence set forth in SEQ ID NO:9 or comprising the CDRs of the $V_H$ and a $V_L$ comprising a sequence set forth in SEQ ID NO:43 or comprising the CDRs of the $V_L$.

In one example, the Fn14-binding protein or anti-Fn14 antibody comprises a heavy chain comprising a sequence set forth in SEQ ID NO:68 and a light chain comprising a sequence set forth in SEQ ID NO:65.

In one example, the Fn14-binding protein or anti-Fn14 antibody comprises a heavy chain comprising a sequence set forth in SEQ ID NO:68 and a light chain comprising a sequence set forth in SEQ ID NO:66.

In one example, the present disclosure provides a method for detecting Fn14 in a sample, the method comprising contacting a sample with a Fn14-binding protein, or an anti-Fn14 antibody, such that the antigen protein complex forms a detectable complex wherein detecting the complex is indicative of the amount of Fn14 in a sample.

The present disclosure additionally provides a method for diagnosing an Fn14-mediated condition in a subject, the method comprising performing the method described herein for detecting Fn14 in a sample from the subject, wherein detection of Fn14 in the sample is indicative of the condition. In one example, the method comprises determining the level of Fn14 in the sample, wherein an increased or decreased level of Fn14 in the sample compared to a control sample is indicative of the condition. In one example, the sample is a tissue sample. In one example, the sample is a blood sample.

The present disclosure additionally provides a method for localizing and/or detecting and/or diagnosing and/or prognosing an Fn14-mediated condition, the method comprising detecting in vivo the Fn14-binding protein or antibody of the present disclosure bound to Fn14, if present, wherein the Fn14-binding protein or antibody is conjugated to a detectable tag.

In one example, the method additionally comprises administering the binding protein or anti-FN14 antibody to the subject.

In one example of any method of treatment/prophylaxis/diagnosis/prognosis described herein the Fn14-mediated condition is cancer, metastasis, excessive vascularization or angiogenesis, an autoimmune disease, an inflammatory disease, a neurodegenerative diseases, a wasting disorder or ischemia.

In one example, the present disclosure provides use of a Fn14-binding protein, or an anti-Fn14 antibody, or a conjugate, or a composition of the present disclosure in the manufacture of a medicament for treating an Fn14-mediated condition in a subject.

In one example, the present disclosure provides use of a medicament for treating a Fn14-mediated condition, wherein the condition is cancer, metastasis, excessive vascularization or angiogenesis, an autoimmune disease, an inflammatory disease, a neurodegenerative disease, a wasting disorder, a cardiovascular disease or ischemia. In one example, the Fn14-mediated condition is cancer and the method reduces or prevents invasiveness of the cancer into tissue of a subject or reduces or prevents metastasis of the cancer. Accordingly, the present disclosure additionally provides a method of treating or preventing a wasting disorder which is associated with a condition, the method comprising administering to a subject a Fn14-binding protein comprising an antigen binding domain of an anti-Fn14 antibody.

In one example, the Fn14-mediated condition is a wasting disorder.

In one example, the wasting disorder is selected from the group consisting of unintended body weight loss, cachexia, pre-cachexia, muscle wasting and fat wasting. For example, the wasting disorder is cachexia.

In one example, the wasting disorder is associated with a condition selected from the group consisting of cancer, metabolic acidosis, infectious diseases, diabetes, autoimmune immune deficiency syndrome (AIDS), autoimmune disorders, addiction to drugs, cirrhosis of the liver, chronic inflammatory disorders, anorexia, chronic heart failure, chronic kidney disease, osteoporosis, skeletal muscle disease, motor neuron disease, multiple sclerosis, muscle atrophy and neurodegenerative disease. For example, the wasting disorder is cancer cachexia.

In one example, the wasting disorder is cachexia, pre-cachexia or sarcopenia (e.g., wasting associated with aging).

In one example, the wasting disorder is cachexia.

In one example, the cachexia is associated with cancer, infectious disease (e.g., tuberculosis or leprosy), AIDS, autoimmune disease (including rheumatoid arthritis or type 1 diabetes), cystic fibrosis, drug addiction, alcoholism or liver cirrhosis.

In one example, the cachexia is associated with a condition selected from rheumatoid arthritis, diabetes, cardiac disease, chronic kidney disease, chronic pulmonary inflammation, intestinal inflammation, inflammatory bowel disease, age, sepsis or AIDS.

In one example, the wasting disorder is cachexia associated with cancer. Numerous types of cancer are associated with cachexia, including solid tumors, carcinoma, neuroma, melanoma, leukemia, lymphoma, sarcoma, fibroma, thyroid cancer, bladder cancer, lung cancer, blastoma, bone cancer, bone tumor, brain stem glioma, brain tumor, breast cancer, bronchial tumor, cervical cancer, colon cancer, colorectal cancer, neuroepithelial tumor, endometrial cancer, endometrial uterine cancer, fallopian tube cancer, kidney cancer, oral cancer, myeloma, neoplasm, neurinoma, neuroblastoma, ovarian cancer, pancreatic cancer, prostate cancer, rectal cancer or renal cell carcinoma. Additional cancers are described herein.

In one example, the method additionally comprises treating the disorder associated with the wasting disorder.

In one example, the method additionally comprises treating cancer, e.g., a cancer associated with cachexia. For example, the treatment comprises administration of an anti-cancer drug or radiation therapy.

In one example, treatment for the cancer or disorder associated with the wasting disorder is performed or administered at the same time or after administering the Fn14-binding protein. For example, the Fn14-binding protein is administered at least once and the subject's weight permitted to increase prior to performing or administering the treatment for cancer or disorder associated with the wasting disorder.

In one example, the Fn14-binding protein or anti-Fn14 antibody comprises a $V_H$ comprising a sequence set forth in SEQ ID NO:9 or comprising the CDRs of the $V_H$ and a $V_L$ comprising a sequence set forth in SEQ ID NO:42 or comprising the CDRs of the $V_L$.

In one example, the Fn14-binding protein or anti-Fn14 antibody comprises a $V_H$ comprising a sequence set forth in SEQ ID NO:9 or comprising the CDRs of the $V_H$ and a $V_L$ comprising a sequence set forth in SEQ ID NO:43 or comprising the CDRs of the $V_L$.

In one example, the Fn14-binding protein or anti-Fn14 antibody comprises a heavy chain comprising a sequence set forth in SEQ ID NO:68 and a light chain comprising a sequence set forth in SEQ ID NO:65.

In one example, the Fn14-binding protein or anti-Fn14 antibody comprises a heavy chain comprising a sequence set forth in SEQ ID NO:68 and a light chain comprising a sequence set forth in SEQ ID NO:66.

Described herein according to any example, a Fn14-binding protein is a recombinant or isolated binding protein.

Described herein according to any example, an anti-Fn14 antibody is a recombinant or isolated anti-Fn14 antibody Described herein according to any example the Fn14-binding protein or anti-Fn14 antibody can be isolated or purified. In one example, the Fn14-binding protein is an isolated protein. In one example, an anti-Fn14 antibody is an isolated antibody. Methods for purifying a Fn14-binding protein or anti-Fn14 antibody are known in the art and disclosed herein.

Described herein according to any example the Fn14-binding protein or anti-Fn14 antibody comprises a variable light chain ($V_L$) that is a kappa light chain.

Described herein according to any example an anti-Fn14 antibody can be any antibody type, for example; IgG, IgE, IgM, IgD, IgA, or IgY or any class, for example IgG1, IgG2, IgG3, IgG4, IgA1 or IgA2. In one example, an anti-Fn14 antibody of the present disclosure is an IgG antibody. In one example, anti-Fn14 antibody of the present disclosure is an IgG1 antibody. In one example, an anti-Fn14 antibody of the present disclosure is an IgG4 antibody.

KEY TO SEQUENCE LISTING

SEQ ID NO:1 Amino acid sequence of human Fn14
SEQ ID NO:2 Heavy chain $V_H$ CDR1 amino acid consensus sequence
SEQ ID NO:3 Heavy chain $V_H$ CDR2 amino acid consensus sequence
SEQ ID NO:4 Light chain $V_L$ CDR1 amino acid consensus sequence
SEQ IN NO:5 Light chain $V_L$ CDR1 amino acid consensus sequence for hFab 6.11, hFab 2.3, hFab 4.1, hFab 4.2, hFab 4.6, hFab 3.4 and hFab 3.6 only
SEQ ID NO:6 Light chain $V_L$ CDR2 amino acid consensus sequence
SEQ ID NO:7 Light chain $V_L$ CDR3 amino acid consensus sequence
SEQ ID NO:8 Light chain $V_L$ CDR3 amino acid consensus sequence for hFab 4.1, hFab 4.2, hFab 4.6, hFab 3.4 and hFab 3.6 only
SEQ ID NO:9 Heavy chain $V_H$ amino acid sequence hFab 6.5
SEQ ID NO:10 Heavy chain $V_H$ amino acid sequence hFab 6.11
SEQ ID NO:11 Heavy chain $V_H$ amino acid sequence hFab 5.4
SEQ ID NO:12 Heavy chain $V_H$ amino acid sequence hFab 5.5
SEQ ID NO:13 Heavy chain $V_H$ amino acid sequence hFab 5.6
SEQ ID NO:14 Heavy chain $V_H$ amino acid sequence hFab 5.7
SEQ ID NO:15 Heavy chain $V_H$ amino acid sequence hFab 5.8
SEQ ID NO:16 Heavy chain $V_H$ amino acid sequence hFab 5.9
SEQ ID NO:17 Heavy chain $V_H$ amino acid sequence hFab 5.10
SEQ ID NO:18 Heavy chain $V_H$ amino acid sequence hFab 5.15
SEQ ID NO:19 Heavy chain $V_H$ amino acid sequence hFab 5.17
SEQ ID NO:20 Heavy chain $V_H$ amino acid sequence hFab 5.18
SEQ ID NO:21 Heavy chain $V_H$ amino acid sequence hFab 5.22

SEQ ID NO:22 Heavy chain $V_H$ amino acid sequence hFab 5.23
SEQ ID NO:23 Heavy chain $V_H$ amino acid sequence hFab 5.24
SEQ ID NO:24 Light chain $V_L$ amino acid sequence hFab 6.5
SEQ ID NO:25 Light chain $V_L$ amino acid sequence hFab 6.11
SEQ ID NO:26 Light chain $V_L$ amino acid sequence hFab 5.4
SEQ ID NO:27 Light chain $V_L$ amino acid sequence hFab 5.5
SEQ ID NO:28 Light chain $V_L$ amino acid sequence hFab 5.7
SEQ ID NO:29 Light chain $V_L$ amino acid sequence hFab 5.9
SEQ ID NO:30 Light chain $V_L$ amino acid sequence hFab 4.1
SEQ ID NO:31 Light chain $V_L$ amino acid sequence hFab 4.2
SEQ ID NO:32 Light chain $V_L$ amino acid sequence hFab 4.3
SEQ ID NO:33 Light chain $V_L$ amino acid sequence hFab 4.4
SEQ ID NO:34 Light chain $V_L$ amino acid sequence hFab 4.6
SEQ ID NO:35 Light chain $V_L$ amino acid sequence hFab 4.7
SEQ ID NO:36 Light chain $V_L$ amino acid sequence hFab 4.8
SEQ ID NO:37 Light chain $V_L$ amino acid sequence hFab 4.14
SEQ ID NO:38 Light chain $V_L$ amino acid sequence hFab 4.20
SEQ ID NO:39 Light chain $V_L$ amino acid sequence hFab 4.21
SEQ ID NO:40 Light chain $V_L$ amino acid sequence hFab 3.1
SEQ ID NO:41 Light chain $V_L$ amino acid sequence hFab 3.4
SEQ ID NO:42 Light chain $V_L$ amino acid sequence hFab 3.6
SEQ ID NO:43 Light chain $V_L$ amino acid sequence hFab 3.9
SEQ ID NO:44 Light chain $V_L$ amino acid sequence hFab 3.10
SEQ ID NO:45 Light chain $V_L$ amino acid sequence hFab 2.1
SEQ ID NO:46 Light chain $V_L$ amino acid sequence hFab 2.2
SEQ ID NO:47 Light chain $V_L$ amino acid sequence hFab 2.3
SEQ ID NO:48 Light chain $V_L$ amino acid sequence hFab 2.10
SEQ ID NO:49 Light chain amino acid sequence hFab 4.1
SEQ ID NO:50 Light chain amino acid sequence hFab 4.2
SEQ ID NO:51 Light chain amino acid sequence hFab 4.3
SEQ ID NO:52 Light chain amino acid sequence hFab 4.4
SEQ ID NO:53 Light chain amino acid sequence hFab 4.6
SEQ ID NO:54 Light chain amino acid sequence hFab 4.7
SEQ ID NO:55 Light chain amino acid sequence hFab 4.8
SEQ ID NO:56 Light chain amino acid sequence hFab 4.14
SEQ ID NO:57 Light chain amino acid sequence hFab 4.20
SEQ ID NO:58 Light chain amino acid sequence hFab 4.21
SEQ ID NO:59 Light chain amino acid sequence hFab 2.1
SEQ ID NO:60 Light chain amino acid sequence hFab 2.2
SEQ ID NO:61 Light chain amino acid sequence hFab 2.3
SEQ ID NO:62 Light chain amino acid sequence hFab 2.10
SEQ ID NO:63 Light chain amino acid sequence hFab 3.1
SEQ ID NO:64 Light chain amino acid sequence hFab 3.4
SEQ ID NO:65 Light chain amino acid sequence hFab 3.6
SEQ ID NO:66 Light chain amino acid sequence hFab 3.9
SEQ ID NO:67 Light chain amino acid sequence hFab 3.10
SEQ ID NO:68 Heavy chain amino acid sequence hFab 6.5
SEQ ID NO:69 Light chain $V_L$ amino acid consensus sequence
SEQ ID NO:70 Light chain $V_L$ amino acid sequence hFab 5.1
SEQ ID NO:71 Light chain $V_L$ amino acid sequence hFab 5.2
SEQ ID NO:72 Light chain $V_L$ amino acid sequence hFab 5.3
SEQ ID NO:73 Light chain $V_L$ amino acid sequence hFab 5.6
SEQ ID NO:74 Light chain $V_L$ amino acid sequence hFab 5.12
SEQ ID NO:75 Light chain $V_L$ amino acid sequence hFab 5.13
SEQ ID NO:76 Light chain amino acid sequence hFab 5.1
SEQ ID NO:77 Light chain amino acid sequence hFab 5.2
SEQ ID NO:78 Light chain amino acid sequence hFab 5.3
SEQ ID NO:79 Light chain amino acid sequence hFab 5.6
SEQ ID NO:80 Light chain amino acid sequence hFab 5.12
SEQ ID NO:81 Light chain amino acid sequence hFab 5.13
SEQ ID NO:82 Ectodomain of Fn14 comprising an alanine in place of the arginine at a position corresponding to amino acid residue 58 of human Fn14

BRIEF DESCRIPTION OF FIGURES

FIG. 2: $V_H$ sequences of clones isolated from the phage display library. Clones from rounds 5-7 were DNA sequenced, all the different $V_H$ sequences are shown. m001-m007 are CRC-BT mouse antibody sequences (as described in WO2013/026099), hPDL (WO2009/020933) and Biogen (WO2009/140177) humanised sequences are shown.

FIG. 3: $V_L$ sequences of clones isolated from the phage display hFab library. Clones from rounds 5-7 were DNA sequenced, the $V_L$ sequences of only a small number of the clones are shown. m001-m007 are CRC-BT mouse antibody sequences, hPDL and Biogen humanised sequences are shown.

FIG. 6: Sequence alignment of light chain shuffled mutants. Sequencing of $V_L$ light chain shuffled mutants after 2-4 rounds of selection on Fn14 antigen. The full wildtype (wt) sequence of 6.5 is shown and areas of sequence homology of 6.5 and the mutants are shown with a dot (.) and a dash (-) represents areas where the sequence is shorter and denotes missing amino acids. The largest sequence deviation from the 6.5 sequence occurred in round 2 with a smaller number of mutations in the CDR regions in later rounds of Fn14 selection in rounds 3 and 4.

DETAILED DESCRIPTION

General

Figure 1:
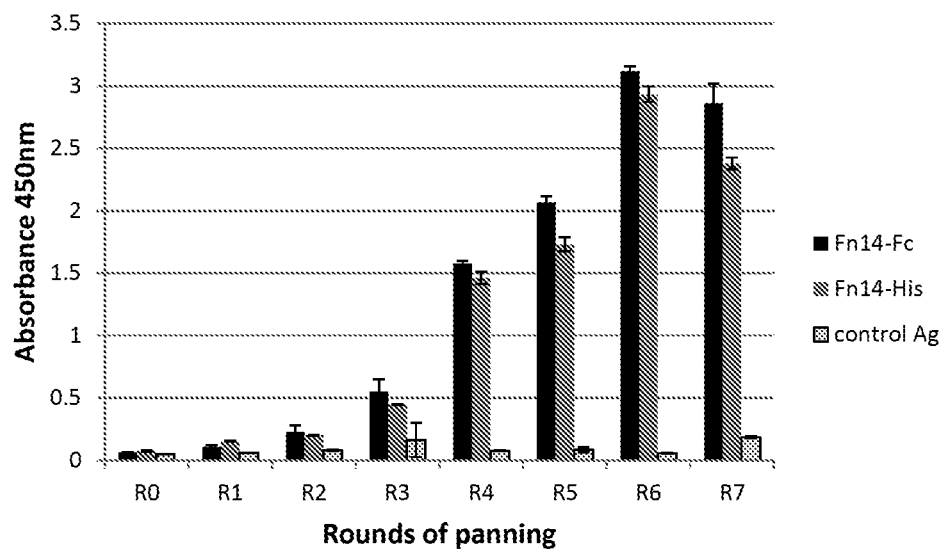
FIG. 1: Isolation of hFabs from the phage display library with high reactivity to recombinant Fn14-Fc and Fn14-His. The reactivity of selected phages from each round of panning was analysed by ELISA. Analysis was performed in duplicate, error bars represent ranges of individual values. The control antigen is a irrelevant Fc-tagged recombinant antigen.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, Perbal (1984), Sambrook et al., (1989), Brown (1991), Glover and Hames (1995 and 1996), and Ausubel et al., (1988, including all updates until present), Harlow and Lane, (1988), Coligan et al., (including all updates until present) and Zola (1987).

The description and definitions of variable regions and parts thereof, immunoglobulins, antibodies and fragments thereof herein may be further clarified by the discussion in Kabat, 1987 and/or 1991, Bork et al., 1994 and/or Chothia and Lesk, 1987 and/or 1989 or Al-Lazikani et al., 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Any example of the disclosure herein shall be taken to apply mutatis mutandis to a Fn14-binding protein or anti-Fn14 antibody comprising a $V_H$ comprising a sequence set forth in SEQ ID NO:9 or comprising the CDRs of the $V_H$ and a $V_L$ comprising a sequence set forth in SEQ ID NO:42 or comprising the CDRs of the $V_L$ or use thereof.

Any example of the disclosure herein shall be taken to apply mutatis mutandis to a $V_H$ comprising a sequence set forth in SEQ ID NO:9 or comprising the CDRs of the $V_H$ and a $V_L$ comprising a sequence set forth in SEQ ID NO:43 or comprising the CDRs of the $V_L$ or use thereof.

Any example of the disclosure herein shall be taken to apply mutatis mutandis to a Fn14-binding protein or anti-Fn14 antibody comprises a heavy chain comprising a sequence set forth in SEQ ID NO:68 and a light chain comprising a sequence set forth in SEQ ID NO:65.

Any example of the disclosure herein shall be taken to apply mutatis mutandis to a Fn14-binding protein or anti-Fn14 antibody comprises a heavy chain comprising a sequence set forth in SEQ ID NO:68 and a light chain comprising a sequence set forth in SEQ ID NO:66.

In one example, reference to CDRs herein is according to the numbering system of Kabat.

Selected Definitions

As used herein, the term "Fn14" collectively refers to Fn14 from all mammals, such as from humans and from rodents. The term "hFn14" or "human Fn14" refers to Fn14 from humans. For the purpose of nomenclature and not limitation, an amino acid sequence of an hFn14 is set forth in SEQ ID NO:1. In the context of the present application, a protein or antibody that binds or binds specifically to Fn14 can also bind to a mutant forms thereof or a mutant ectodomain thereof, e.g., comprising an alanine at a position corresponding to position 58 of human Fn14.

As used herein, the term "Fn14 ectodomain" refers to residues 2 to 51 as set forth in SEQ ID NO:1.

For the purposes for the present disclosure, the term "antibody" includes four chain protein comprising e.g., two light chains and two heavy chains including recombinant or modified antibodies (e.g., chimeric antibodies, humanized antibodies, primatized antibodies, de-immunized antibodies and half antibodies, bispecific antibodies) capable of specifically binding to one or a few closely related antigens (e.g., Fn14) by virtue of a Fv. An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50-70 kDa) covalently linked and two light chains (~23 kDa each). A light chain generally comprises a variable region and a constant domain and in mammals is either a κ light chain or a λ, light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain (CL which is ~110 amino acids in length) is aligned with and disulfide bonded to the first constant domain of the heavy chain (CH which is –330-440 amino acids in length). The light chain variable region is aligned with the variable region of the heavy chain. The antibody heavy chain can comprise 2 or more additional CH domains (such as, CH2, CH3 and the like) and can comprise a hinge region between the CH1 and CH2 constant domains. Antibodies can be of any type (e.g., IgG, IgE, IgM, IgD, IgA, and IgY), class (e.g., IgG1, IgG2, IgG3, IgG4, IgA1 and IgA2) or subclass. In one example, the antibody is a human antibody or a deimmunized or germlined version thereof, or an affinity matured version thereof.

The terms "full-length antibody," or "whole antibody" are used interchangeably to refer to an antibody in its substantially intact form, as opposed to an antigen binding fragment of an antibody. Specifically, whole antibodies include those with heavy and light chains including a constant region. The constant region may be wild-type sequence constant regions (e.g., human wild-type sequence constant regions) or amino acid sequence variants thereof.

The term "Fn14-binding protein" shall be taken to include a single polypeptide chain, (i.e., a series of contiguous amino acids linked by peptide bonds), or a series of polypeptide chains covalently or non-covalently linked to one another (i.e., a polypeptide complex) capable of binding to Fn14 in the manner described and/or claimed herein. For example, the series of polypeptide chains can be covalently linked using a suitable chemical or a disulphide bond. Examples of non-covalent bonds include hydrogen bonds, ionic bonds, Van der Waals forces, and hydrophobic interactions. A non-covalent bond contemplated by the present disclosure is the interaction between a $V_H$ and a $V_L$, e.g., in some forms of diabody or a triabody or a tetrabody or a Fv.

The term "polypeptide chain" will be understood to mean from the foregoing paragraph to mean a series of contiguous amino acids linked by peptide bonds.

As the term suggests, "anti-Fn14 antibody" means an antibody that specifically binds to Fn14, subject to the discussion herein regarding additionally binding to mutant forms of Fn14.

As used herein, "variable region" refers to the portions of the light and/or heavy chains of an antibody as defined herein or of a heavy chain only antibody (e.g., camelid antibodies or cartilaginous fish immunoglobulin new antigen receptors (IgNARs)) that is capable of specifically binding to an antigen and includes amino acid sequences of complementary determining regions "CDRs"; i.e., CDR1, CDR2, and CDR3, and FRs. For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region typically has three CDR regions identified as CDR1, CDR2 and CDR3. Each complementarity determining region may comprise amino acid residues from a "complementarity determining region" as defined by Kabat et al., (1987 and/or 1991). For example, in a heavy chain variable region CDRH1 is between residues 31-35, CDRH2 is between residues 50-65 and CDRH3 is between residues 95-102. In a light chain CDRL1 is between residues 24-34, CDRL2 is between residues 50-56 and CDRL3 is between residues 89-97. These CDRs can also comprise numerous insertions, e.g., as described in Kabat (1987 and/or 1991). The present disclosure is not limited to FRs and CDRs as defined by the Kabat numbering system, but includes all numbering systems, including the canonical numbering system or of Chothia and Lesk (1987): Chothia et al. (1989); and/or Al-Lazikani et al., (1997); the numbering system of Honnegher and Pliikthun (2001): the IMGT system discussed in Giudicelli et al., (1997); or the Enhanced Chothia Numbering Scheme (accessible at hypertext transfer protocol and world wide web, bioinfo.org.uk/mdex.html). In one example, the CDRs and/or FRs are defined according to the Kabat numbering system, e.g., as depicted in FIGS. 9A-9D in bold text. Optionally, heavy chain CDR2 according to the Kabat numbering system does not comprise the five C-terminal amino acids listed herein or any one or more of those amino acids are substituted with another naturally-occurring amino acid. In an additional, or alternative, option, light chain CDR1 does not comprise the four N-terminal amino acids listed herein or any one or more of those amino acids are substituted with another naturally-occurring amino acid. In this regard, Padlan et al., 1995 established that the five C-terminal amino acids of heavy chain CDR2 and/or the four N-terminal amino acids of light chain CDR1 are not generally involved in antigen binding. In one example, the CDRs and/or FRs are defined according to the Chothia numbering system, e.g., as depicted in FIGS. 9A-9D in underlined text.

As used herein, the term "Kabat numbering system" refers to the scheme for numbering antibody variable regions and identifying CDRs (hypervariable regions) as set out in Kabat et al., (1987 and/or 1991).

As used herein, the term "Chothia numbering system" refers to the scheme for numbering antibody variable regions and identifying CDRs (structural loops) as set out in of Chothia and Lesk (1987) or Al-Lazikani et al., (1997).

"Framework regions" (hereinafter FR) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding domain, i.e., capable of specifically binding to an antigen (e.g., Fn14). The $V_H$ and the $V_L$ which form the antigen binding domain can be in a single polypeptide chain or in different polypeptide chains. Furthermore an Fv of the disclosure (as well as any protein of the disclosure) may have multiple antigen binding sites which may or may not bind the same antigen. This term shall be understood to encompass fragments directly derived from an antibody as well as proteins produced using recombinant means. In some examples, the $V_H$ is not linked to a heavy chain constant domain CH1 and/or the $V_L$ is not linked to a light chain constant domain (CL), e.g., a domain antibody. Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., CH2 or CH3 domain, e.g., a minibody. A "hFab" is reference is reference to a human Fab. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A Fab fragment generally comprises or consists of a $V_H$ and $C_H1$ and a $V_L$ and $C_L$. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. An "F(ab')2 fragment" of an antibody consists of a dimer of two Fab' fragments held together by two disulfide bonds, and is obtained by treating a whole antibody molecule with the enzyme pepsin, without subsequent reduction. An "Fab2" fragment is a recombinant fragment comprising two Fab fragments linked using, for example a leucine zipper or a CH3 domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker. A discussion of exemplary Fv containing proteins falling within the scope of this term is provided herein below.

As used herein, the term "antigen binding domain" shall be taken to mean a region of an antibody that is capable of specifically binding to an antigen, i.e., a $V_H$ or a $V_L$ or a Fv or a variable region as defined herein. The antigen binding domain need not be in the context of an entire antibody, e.g., it can be in isolation (e.g., a domain antibody) or in another form, e.g., as described herein, such as a scFv.

The term "constant region" (syn. CR) as used herein, refers to a portion of an antibody comprising at constant domains and which is generally (though not necessarily) glycosylated and which binds to one or more Fc receptors and/or components of the complement cascade (e.g., confers effector functions). The heavy chain constant region can be selected from any of the five isotypes: α, δ, ε, γ, or μ. Furthermore, heavy chains of various subclasses (such as the IgG subclasses of heavy chains) are responsible for different effector functions and thus, by choosing the desired heavy chain constant region, proteins with desired effector function can be produced. Exemplary heavy chain constant regions are gamma 1 (IgG1), gamma 2 (IgG2), gamma 3 (IgG3) and gamma 4 (IgG4).

A "constant domain" is a domain in an antibody the sequence of which is highly similar in antibodies/antibodies of the same type, e.g., IgG or IgM or IgE. A constant region of an antibody generally comprises a plurality of constant domains, e.g., the constant region of γ, α and δ heavy chains comprise three constant domains and the Fc of γ, α and δ heavy chains comprise two constant domains. A constant region of μ and ε heavy chains comprises four constant domains and the Fc region comprises two constant domains.

As used herein, the term "binds" in reference to the interaction of a protein or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the antibody, will reduce the amount of labeled "A" bound to the antibody.

As used herein, the term "specifically binds" shall be taken to mean a protein of the disclosure reacts or associates more frequently, more rapidly, with greater duration and/or with greater affinity with a particular antigen or antigens or cell expressing same than it does with alternative antigens or cells. For example, a protein that specifically binds to an antigen binds that antigen with greater affinity (e.g., 20 fold or 40 fold or 60 fold or 80 fold to 100 fold or 150 fold or 200 fold greater affinity), avidity, more readily, and/or with greater duration than it binds to other antigens, e.g., to other TNF superfamily receptors or to antigens commonly recognized by polyreactive natural antibodies (i.e., by naturally occurring antibodies known to bind a variety of antigens naturally found in humans). It is also understood by reading this definition that, for example, a protein that specifically binds to a first antigen may or may not specifically bind to a second antigen. As such "specific binding" does not necessarily require exclusive binding or non-detectable binding of another antigen, this is meant by the term "selective binding".

By "isolated" is meant that the protein is substantially removed from its naturally-occurring environment, e.g., is in a heterologous environment and/or that it is substantially free of contaminating agents, e.g., at least about 70% or 75% or 80% or 85% or 90% or 95% or 96% or 97% or 98% or 99% free of contaminating agents. The term "competitively inhibits" shall be understood to mean that a protein of the disclosure reduces or prevents binding of a recited antibody produced to Fn14 or a fragment thereof. It will be apparent from the foregoing that the protein need not completely inhibit binding of the antibody, rather it need only reduce binding by a statistically significant amount, for example, by at least about 10% or 20% or 30% or 40% or 50% or 60% or 70% or 80% or 90% or 95%. Methods for determining competitive inhibition of binding are known in the art and/or described herein. For example, the antibody is exposed to Fn14 or a fragment thereof either in the presence or absence of the protein. If less antibody binds in the presence of the protein than in the absence of the protein, the protein is considered to competitively inhibit binding of the antibody. In one example, the protein and antibody are exposed to Fn14 substantially simultaneously. Additional methods for determining competitive inhibition of binding will be apparent to the skilled artisan and/or described herein. In one example, the antigen binding domain of the protein competitively inhibits binding of the antibody.

The term "Fn14-mediated condition" shall be taken to encompass any disease or disorder caused by or associated with excess numbers of cells expressing Fn14 and/or overexpression of Fn14 and/or excess activity of Fn14 and/or an excess level of Tweak, e.g., in serum or tissue of a subject. Exemplary Fn14-mediated conditions are cancer, metastasis, excessive vascularization or angiogenesis, autoimmune diseases, inflammatory diseases, neurodegenerative diseases, keloid scarring, graft versus host disease, graft rejection, cardiovascular disease and ischemia (including stroke).

As used herein, the term "wasting disorder" refers to a disorder which involves, results at least in part from, or includes loss of weight, muscle atrophy, fatigue, weakness in someone who is not actively trying to lose weight. Wasting disorders are commonly characterized by inadvertent and/or uncontrolled (in the absence of medical intervention) loss of muscle and/or fat. The term encompasses cachexia or other forms of wasting, e.g., denervation-induced wasting.

As used herein, the term "cachexia" will be understood to refer to metabolic condition associated with an underlying (or another) condition, wherein cachexia is characterized by loss of body weight and loss of muscle with or without loss of fat mass. Cachexia is generally associated with increased protein catabolism due to underlying disease(s). Contributory factors to the onset of cachexia are anorexia and metabolic alterations (e.g., increased inflammatory status, increased muscle proteolysis and impaired carbohydrate, protein and lipid metabolism). A prominent clinical feature of cachexia is weight loss in adults (optionally, corrected for fluid retention) or growth failure in children (excluding endocrine disorders). Anorexia, inflammation, insulin resistance and increased muscle protein breakdown are frequently associated with cachexia. Cachexia is distinct from starvation, primary depression, malabsorption and hyperthyroidism and is associated with increased morbidity. Cachexia can be associated with or result from (directly or indirectly) various underlying disorders including cancer, metabolic acidosis (from decreased protein synthesis and increased protein catabolism), certain infectious diseases (e.g. bacterial infections, including tuberculosis, AIDS), some autoimmune disorders, addiction to drugs such as amphetamines or cocaine, chronic alcoholism and/or cirrhosis of the liver, chronic inflammatory disorders, anorexia, neurological conditions and/or neurodegenerative disease. In one example, cachexia is cancer cachexia (cachexia associated with cancer).

In other examples, muscle wasting and/or unintended body weight loss associated with neurological conditions, immobility or impaired mobility due to various diseases such as neurodegenerative disease, multiple sclerosis, spinal cord injury, are included in the term. Cachexia can be diagnosed based on one or more of the following:

Weight loss of at least 5% over a period of six months (in the absence of starvation);
A BMI <20 together with weight loss; or
Appendicular skeletal muscle index consistent with sarcopenia (males <7.26 kg/m$^2$; females <5.45 kg/m$^2$) together with weight loss.

As used herein, the terms "preventing", "prevent" or "prevention" include administering a therapeutically effective amount of a binding protein or antibody of the disclosure sufficient to stop or hinder the development of at least one symptom of a specified disease or condition.

As used herein, the terms "treating", "treat" or "treatment" include administering a therapeutically effective amount of a protein described herein sufficient to reduce or eliminate at least one symptom of a specified disease or condition.

As used herein, the term "subject" shall be taken to mean any animal including mammals. Exemplary subjects include humans or non-human primates. In one example, the subject is a human.

The term "sample" shall be taken to encompass the recited sample (e.g., a blood, tissue or urine sample) and any fraction thereof (e.g., plasma, serum or buffy coat) or cells derived therefrom (e.g., peripheral blood mononuclear cells) or processed forms thereof.

Fn14-Binding Proteins
Antibodies

Methods for generating antibodies are known in the art and/or described in Harlow and Lane (1988) or Zola (1987). Generally, in such methods an Fn14 protein or immunogenic fragment or epitope-containing thereof or a cell expressing and displaying same (i.e., an immunogen), optionally formulated with any suitable or desired carrier, adjuvant, or pharmaceutically acceptable excipient, is administered to a non-human animal subject, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are exemplary antibodies contemplated by the present disclosure. The term "monoclonal antibody" or "mAb" or "MAb" refers to a homogeneous antibody population capable of binding to the same antigen(s) and, for example, to the same epitope within the antigen. This term is not intended to be limited with respect to the source of the antibody or the manner in which it is made.

For the production of mAbs any one of a number of known techniques may be used, such as, for example, the procedure exemplified in U.S. Pat. No. 4,196,265 or Harlow and Lane (1988) or Zola (1987).

For example, a suitable animal is immunized with an effective amount of the protein or immunogenic fragment or epitope thereof or cell expressing same under conditions sufficient to stimulate antibody producing cells. Rodents such as rabbits, mice and rats are exemplary animals, with mice being most commonly used. Mice genetically-engineered to express human immunoglobulin proteins, and not express murine immunoglobulin proteins, can also be used to generate an antibody of the present disclosure (e.g., as described in WO2002/066630).

Following immunization, somatic cells with the potential for producing antibodies, specifically B lymphocytes (B cells), are selected for use in the MAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen. B cells and immortal cells are fused by incubating a mixture of the cells types in the presence of an agent or agents (chemical or electrical) that promote the fusion of cell membranes. Fusion methods using Sendai virus have been described by Kohler and Milstein, (1975); and Kohler and Milstein, (1976). Methods using polyethylene glycol (PEG), such as 37% (v/v) PEG, are described by Gefter et al, (1977). The use of electrically induced fusion methods is also appropriate.

Hybrids are amplified by culture in a selective medium comprising an agent that blocks the de novo synthesis of nucleotides in the tissue culture media. Exemplary and exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like). The present disclosure also contemplates sub-cloning of antibody producing cells, e.g., as exemplified herein.

Alternatively, ABL-MYC technology (NeoClone, Madison Wis. 53713, USA) is used to produce cell lines secreting MAbs (e.g., as described in Kumar et al, 1999).

Antibodies can also be produced or isolated by screening a display library, e.g., a phage display library, e.g., as described in U.S. Pat. No. 6,300,064 EP0368684 and/or U.S. Pat. No. 5,885,793.

De-Immunized Antibodies and Proteins

The present disclosure also contemplates a de-immunized antibody or Fn14-binding protein. De-immunized antibodies and Fn14-binding proteins have one or more epitopes, e.g., B cell epitopes or T cell epitopes removed (i.e., mutated) to thereby reduce the likelihood that a subject will raise an immune response against the antibody or protein. Methods for producing de-immunized antibodies and proteins are known in the art and described, for example, in WO00/34317, WO2004/108158 and WO2004/064724.

Methods for introducing suitable mutations and expressing and assaying the resulting protein will be apparent to the skilled artisan based on the description herein.

Human Antibody

The term "human antibody" as used herein refers to antibodies having variable regions (e.g. $V_H$, $V_L$) and, optionally constant regions derived from or corresponding to sequences found in humans, e.g. in the human germline or somatic cells. The "human" antibodies can include amino acid residues not encoded by human sequences, e.g. mutations introduced by random or site directed mutations in vitro (in particular mutations which involve conservative substitutions or mutations in a small number of residues of the antibody, e.g. in 1, 2, 3, 4, 5 or 6 of the residues of the antibody, e.g. in 1, 2, 3, 4, 5 or 6 of the residues making up one or more of the CDRs of the antibody). These "human antibodies" do not actually need to be produced by a human, rather, they can be produced using recombinant means and/or isolated from a transgenic animal (e.g., mouse) comprising nucleic acid encoding human antibody constant and/or variable regions (e.g., as described above). Human antibodies can be produced using various techniques known in the art, including phage display libraries (e.g., as described in U.S. Pat. No. 5,885,793).

Human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope (e.g., as described in U.S. Pat. No. 5,565,332).

Germlined Antibodies

As discussed above a "human antibody" is derived from or corresponding to sequences for in humans e.g. germ line or somatic cells which can include amino acids residues not encoded by human sequences e.g. in some instances a mutation may be introduced for example by affinity maturation or light chain shuffling or as a result of a use of a synthetic library that is not encoded by human species. As referred to herein a "germlined" antibody is a human antibody in which one or more amino acids in a chain which are not encoded by the human species are replaced or substituted with an amino acids from the germline species.

Deimmunized Antibodies

"Deimmunized" binding proteins and antibodies have one or more epitopes, e.g., B cell epitopes or T cell epitopes removed (i.e., mutated) to thereby reduce the likelihood that a subject will raise an immune response against the antibody or protein. For example, a Fn14-binding protein of the disclosure is analyzed to identify one or more B or T cell epitopes and one or more amino acid residues within the epitope is mutated to thereby reduce the immunogenicity of the Fn14-binding protein.

Variable Region Containing Proteins

Heavy Chain Antibodies

Heavy chain antibodies differ structurally from many other forms of antibodies, in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain antibodies are generally referred to as "$V_{HH}$ domains" in camelid antibodies and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

A general description of heavy chain antibodies from camelids and the variable regions thereof and methods for their production and/or isolation and/or use is found inter alia in the following references WO94/04678 or WO97/49805.

A general description of heavy chain immunoglobulins from cartilaginous fish and the variable regions thereof and methods for their production and/or isolation and/or use is found in WO2005/118629.

Single-Domain Antibodies

In some examples, a Fn14-binding protein of the disclosure is a single-domain antibody (which is used interchangeably with the term "domain antibody" or "dAb"). A single-domain antibody is a single polypeptide chain comprising all or a portion of the heavy chain variable region of an antibody. In certain example, a single-domain antibody is a human single-domain antibody (Domantis, Inc., Waltham, Mass.; see, e.g., U.S. Pat. No. 6,248,516; WO90/05144 and/or WO2004/058820).

Diabodies, Triabodies, Tetrabodies

Exemplary Fn14-binding proteins comprising an antibody antigen binding domain are diabodies, triabodies, tetrabodies and higher order protein complexes such as those described in WO98/044001 and WO94/007921.

For example, a diabody is a protein comprising two associated polypeptide chains, each polypeptide chain comprising the structure $V_L$-X-$V_H$ or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form an Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

Single Chain Fv (scFv) Fragments

The skilled artisan will be aware that scFvs comprise $V_H$ and $V_L$ regions in a single polypeptide chain. The polypeptide chain further comprises a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with (Gly$_4$Ser)$_3$ being one of the more favored linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv (see, for example, Brinkmann et al., 1993).

Alternatively, or in addition, the present disclosure provides a dimeric scFv, i.e., a protein comprising two scFv molecules linked by a non-covalent or covalent linkage, e.g., by a leucine zipper domain (e.g., derived from Fos or Jun) (see, for example, Kruif and Logtenberg, 1996). Alternatively, two scFvs are linked by a peptide linker of sufficient length to permit both scFvs to form and to bind to an antigen, e.g., as described in US20060263367.

For a Review of scFv, see Plückthun (1994).

Minibodies

The skilled artisan will be aware that a minibody comprises the $V_H$ and $V_L$ domains of an antibody fused to the $C_H2$ and/or $C_H3$ domain of an antibody. Optionally, the minibody comprises a hinge region between the $V_H$ and a $V_L$, sometimes this conformation is referred to as a Flex Minibody. A minibody does not comprise a $C_H1$ or a $C_L$. In one example, the $V_H$ and $V_L$ domains are fused to the hinge region and the $C_H3$ domain of an antibody. At least one of the variable regions of said minibody binds to Fn14 in the manner of the disclosure. Exemplary minibodies and methods for their production are described, for example, in WO94/09817.

Other Variable Region Containing Proteins

The present disclosure also contemplates other variable region containing Fn14-binding proteins, such as:
(i) "key and hole" bispecific proteins as described in U.S. Pat. No. 5,731,168;
(ii) heteroconjugate proteins, e.g., as described in U.S. Pat. No. 4,676,980;
(iii) heteroconjugate proteins produced using a chemical cross-linker, e.g., as described in U.S. Pat. No. 4,676,980;
(iv) Fab'-SH fragments, e.g., as described in Shalaby (1992);
(v) single chain Fab; or
(vi) Fab$_3$ (e.g., as described in EP19930302894).

Constant Regions

The present disclosure encompasses Fn14-binding proteins comprising a variable region and a constant region or a domain(s) thereof, e.g., Fc, $C_H2$ and/or $C_H3$ domain. The skilled artisan will be aware of the meaning of the terms constant region and constant domain based on the disclosure herein and references discussed herein.

Constant region sequences useful for producing the Fn14-binding proteins of the present disclosure may be obtained from a number of different sources. In some examples, the constant region or portion thereof of the Fn14-binding protein is derived from a human antibody. Moreover, the constant domain or portion thereof may be derived from any antibody class, including IgM, IgG, IgD, IgA and IgE, and any antibody isotype, including IgG1, IgG2, IgG3 and IgG4. In one example, the human isotype IgG1 or IgG4 is used.

A variety of constant region gene sequences are available in the form of publicly accessible deposits or the sequence thereof is available from publicly available databases. Constant regions can be selected having a particular effector function (or lacking a particular effector function) or with a particular modification to reduce immunogenicity.

Suitably, a protein of the present disclosure has or displays an effector function that facilitates or enables at least partial depletion, substantial depletion or elimination of cells expressing Fn14. Such an effector function may be enhanced binding affinity to Fc receptors, antibody-dependent cell-mediated cytotoxicity (ADCC), antibody-dependent cell mediated phagocytosis (ADCP) and/or complement dependent cytotoxicity (CDC).

In one example, the Fn14-binding protein is capable of inducing an enhanced level of effector function.

In one example, the level of effector function induced by the constant region is enhanced relative to a wild-type Fc region of an IgG1 antibody or a wild-type Fc region of an IgG3 antibody.

In another example, the constant region is modified to increase the level of effector function it is capable of inducing compared to the constant region without the modification. Such modifications can be at the amino acid level and/or the secondary structural level and/or the tertiary structural level and/or to the glycosylation of the Fc region.

The skilled addressee will appreciate that greater effector function may be manifested in any of a number of ways, for example as a greater level of effect, a more sustained effect or a faster rate of effect.

Exemplary constant region modifications include amino acid substitutions, such as, S239D/I332E, numbered according to the EU index of Kabat or S239D/A330L/I332E, numbered according to the EU index of Kabat. Additional amino acid substitutions that increase ability of an Fc region to induce effector function are known in the art and/or described, for example, in U.S. Pat. Nos. 6,737,056 or 7,317,091.

In one example, the glycosylation of the constant region is altered to increase its ability to induce enhanced effector function. In some examples, Fc regions according to the present disclosure comprise a carbohydrate structure that lacks fucose attached (directly or indirectly) to an Fc region, i.e., the Fc region is "afucosylated". Such variants may have an improved ability to induce ADCC. Methods for producing afucosylated antibodies include, expressing the Fn14-binding protein in a cell line incapable of expressing α-1, 6-fucosyltransferase (FUT8) (e.g., as described in Yumane-Ohnuki et al., 2004). Other methods include the use of cell lines which inherently produce antibodies capable of inducing enhanced effector function (e.g. duck embryonic derived stem cells for the production of viral vaccines, WO2008/129058; Recombinant protein production in avian EBX® cells, WO 2008/142124).

Fn14-binding proteins can also comprise an Fc region capable of inducing enhanced levels of CDC. For example, hybrids of IgG1 and IgG3 produce antibodies having enhanced CDC activity (Natsume et al., 2008).

Methods for determining the ability of an antibody or antigen binding fragment thereof to induce effector function and known in the art and/or described herein.

Neutralizing Fn14-binding proteins of the present disclosure can comprise an IgG4 constant region or a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat. This position corresponds to position 228 of the hinge region according to the EU numbering system. In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Mutant Proteins

The present disclosure provides a Fn14-binding protein having at least 70% identity to a sequence of the disclosure and having the same functional characteristics described or claimed herein.

In one example, a Fn14-binding protein of the disclosure comprises a sequence having at least 70%, or 75%, or 80%, or 85%, or 90%, or 91%, or 92%, or 93%, or 94%, or 95%, or 96%, or 97%, or 98%, or 99% identity, or is identical to a $V_H$ sequence disclosed herein.

In one example, a Fn14-binding protein of the disclosure comprises a sequence having at least 70%, or 75%, or 80%, or 85%, or 90%, or 91%, or 92%, or 93%, or 94%, or 95%, or 96%, or 97%, or 98%, or 99% identity, or is identical to a $V_L$ sequence disclosed herein.

In one example, a Fn14-binding protein of the disclosure comprises a sequence having at least 70%, or 75%, or 80%, or 85%, or 90%, or 91%, or 92%, or 93%, or 94%, or 95%, or 96%, or 97%, or 98%, or 99% identity, or is identical to a CDR sequence disclosed herein.

Affinity Maturation

In a further example, an existing Fn14-binding protein of the disclosure is affinity matured to produce an antibody capable of binding to Fn14 with increased affinity. For example, the sequence encoding the $V_L$ and/or $V_H$ is isolated and the CDR encoding region (e.g., the region encoding CDR3 of the $V_L$ and/or $V_H$) is mutated such that one or more amino acid substitutions is introduced. The resulting mutant Fn14-binding protein is then screened for binding to Fn14, e.g., in a competitive assay.

The Fn14-binding proteins according to the disclosure may be soluble secreted proteins or may be presented as a fusion protein on the surface of a cell, or particle (e.g., a phage or other virus, a ribosome or a spore). Exemplary phage display methods are described, for example, in U.S. Pat. Nos. 5,821,047; 6,248,516 and 6,190,908. Phage display particles produced using these methods are then screened to identify a displayed Fn14-binding protein having a conformation sufficient for binding to a target antigen e.g., Fn14.

Protein Production

In one example, a Fn14-binding protein of the disclosure is produced by culturing a cell line under conditions sufficient to produce the protein, e.g., as described herein and/or as is known in the art.

Recombinant Expression

In the case of a recombinant protein, nucleic acid encoding same is placed into one or more expression construct, e.g., expression vector(s), which is/are then transfected into host cells, such as cells that can produce a disulphide bridge or bond, such as E. coli cells, yeast cells, insect cells, or mammalian cells. Exemplary mammalian cells include simian COS cells, Chinese Hamster Ovary (CHO) cells, or myeloma cells that do not otherwise produce immunoglobulin protein. Molecular cloning techniques to achieve these ends are known in the art and described, for example in Ausubel or Sambrook. A wide variety of cloning and in vitro amplification methods are suitable for the construction of recombinant nucleic acids. Methods of producing recombinant antibodies are also known in the art. See U.S. Pat. Nos. 4,816,567; 7,923,221 and 7,022,500.

Following isolation, the nucleic acid encoding a protein of the disclosure is inserted into an expression construct or replicable vector for further cloning (amplification of the DNA) or for expression in a cell-free system or in cells. For example, the nucleic acid is operably linked to a promoter, As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Cell free expression systems are also contemplated by the present disclosure.

Isolation of Proteins

A Fn14-binding protein of the present disclosure is can be isolated or purified.

Methods for purifying a Fn14-binding protein of the disclosure are known in the art and/or described herein.

When using recombinant techniques, the Fn14-binding protein of the disclosure can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Where the protein is secreted into the medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Zola (1997).

The skilled artisan will also be aware that a Fn14-binding protein of the disclosure can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. For example, the tag is a hexa-his tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Conjugates

The present disclosure also provides conjugates of Fn14-binding proteins described herein according to any example. Examples of compounds to which a protein can be conjugated are selected from the group consisting of a radioisotope, a detectable label, a therapeutic compound, a colloid, a toxin, a nucleic acid, a peptide, a protein, a compound that increases the half life of the protein in a subject and mixtures thereof. Exemplary therapeutic agents include, but are not limited to an anti-angiogenic agent, an anti-neovascularization and/or other vascularization agent, an anti-proliferative agent, a pro-apoptotic agent, a chemotherapeutic agent or a therapeutic nucleic acid.

A toxin includes any agent that is detrimental to (e.g., kills) cells. For a description of these classes of drugs which are known in the art, and their mechanisms of action, see Goodman et al., (1990). Additional techniques relevant to the preparation of immunoglobulin-immunotoxin conjugates are provided in for instance in U.S. Pat. No. 5,194,594. Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO93/21232.

Suitable chemotherapeutic agents for forming immunoconjugates of the present disclosure include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)).

In one example, a Fn14-binding protein as described herein according to any example is conjugated or linked to another protein, including another Fn14-binding protein of the disclosure or a protein comprising an antibody variable region, such as an antibody or a protein derived therefrom, e.g., as described herein. Other proteins are not excluded. Additional proteins will be apparent to the skilled artisan and include, for example, an immunomodulator or a half-life extending protein or a peptide or other protein that binds to serum albumin amongst others.

Exemplary serum albumin binding peptides or protein are described in US20060228364 or US20080260757.

A variety of radionuclides are available for the production of radioconjugated proteins. Examples include, but are not limited to, low energy radioactive nuclei (e.g., suitable for diagnostic purposes), such as $^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like. For example, the radionuclide is a gamma, photon, or positron-emitting radionuclide with a half-life suitable to permit activity or detection after the elapsed time between administration and localization to the imaging site. The present disclosure also encompasses high energy radioactive nuclei (e.g., for therapeutic purposes), such as $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{158}Re$. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic. Alternatively, high-energy isotopes may be generated by thermal irradiation of an otherwise stable isotope, for example as in boron neutron-capture therapy (Guan et al., 1998).

In another example, the protein is conjugated to a "receptor" (such as streptavidin) for utilization in cell pretargeting wherein the conjugate is administered to the patient, followed by removal of unbound conjugate from the circulation using a clearing agent and then administration of a "ligand" (e.g., avidin) that is conjugated to a therapeutic agent (e.g., a radionucleotide).

The Fn14-binding proteins of the present disclosure can be modified to contain additional nonproteinaceous moieties that are known in the art and readily available. For example, the moieties suitable for derivatization of the protein are physiologically acceptable polymer, e.g., a water soluble polymer. Such polymers are useful for increasing stability and/or reducing clearance (e.g., by the kidney) and/or for reducing immunogenicity of a Fn14-binding protein of the disclosure. Non-limiting examples of water soluble polymers include, but are not limited to, polyethylene glycol (PEG), polyvinyl alcohol (PVA), or propropylene glycol (PPG).

In one example, a Fn14-binding protein as described herein according to any example comprises one or more detectable markers to facilitate detection and/or isolation. For example, the compound comprises a fluorescent label such as, for example, fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7, fluorescein (5-carboxyfluorescein-N-hydroxysuccinimide ester), rhodamine (5,6-tetramethyl rhodamine). The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm).

Alternatively, or in addition, the Fn14-binding protein as described herein according to any example is labeled with, for example, a fluorescent semiconductor nanocrystal (as described, for example, in U.S. Pat. No. 6,306,610).

Alternatively, or in addition, the Fn14-binding protein is labeled with, for example, a magnetic or paramagnetic compound, such as, iron, steel, nickel, cobalt, rare earth materials, neodymium-iron-boron, ferrous-chromium-cobalt, nickel-ferrous, cobalt-platinum, or strontium ferrite.

Immobilized Proteins

In one example a Fn14-binding protein is immobilized on a solid or semi-solid matrix. The term "immobilization" is to be understood to involve various methods and techniques to fix proteins onto specific matrices, e.g. as described in WO99/56126 or WO02/26292. For example, immobilization can serve to stabilize the proteins so that its activity is not reduced or adversely modified by biological, chemical or physical exposure, especially during storage or in single-batch use.

Assaying Activity of a Protein of the Disclosure

Binding Assays

One form of such an assay is an antigen binding assay, e.g., as described in Scopes (1994). Such a method generally involves labeling the Fn14-binding protein and contacting it with immobilized antigen or a fragment thereof, e.g., a protein comprising an extracellular domain of Fn14 fused to an Fc region of an antibody or to an ectodomain of Fn14 or a mutant form thereof, e.g., as described herein. Following washing to remove non-specific bound protein, the amount of label and, as a consequence, bound protein is detected. Of course, the Fn14-binding protein can be immobilized and the antigen labeled. Panning-type assays, e.g., as described or exemplified herein can also be used.

Cell Killing Assays

In another example, the ability of a Fn14-binding protein of the disclosure (e.g., linked to a toxic compound or a constant region) is assessed by determining their ability to induce death of a cell. In the case of a constant region-linked Fn14-binding protein it is desirable to perform such an assay in the presence of immune effector cells and/or complement (e.g., to facilitate ADCC/CDC).

In Vivo Therapeutic Efficacy Assays

A Fn14-binding protein of the disclosure can also be tested in vivo. For example, a Fn14-binding protein can be tested in an animal model of a wasting disorder as described herein, e.g., in which a non-human mammal is administered a tumor cell expressing Fn14 under conditions for a wasting disorder to develop. A Fn14-binding protein of the disclosure is then administered and the effect on the wasting disorder is assessed, e.g., by monitoring body weight changes. A Fn14-binding protein that reduces or prevents loss of body weight or induces a gain in body weight is selected as a potential therapeutic agent.

A Fn14-binding protein of the disclosure can also be selected on the basis of its ability to reduce or prevent invasiveness of a tumor cell. For example, a tumor cell is implanted into a subject, e.g., into a muscle, and the subject is administered a test Fn14-binding protein (or for controls, no Fn14-binding protein is administered). A reduction in invasion of tissue surrounding the tumor cell (e.g., as assessed using histopathology) in the presence of the Fn14-binding protein compared to in the absence of the Fn14-binding protein indicates that the Fn14-binding protein reduces or prevent invasiveness of a tumor cell.

A Fn14-binding protein of the disclosure can also be assessed for therapeutic efficacy by determining its ability to slow or prevent development of a tumor in a xenograft model.

A Fn14-binding protein of the disclosure can also be assessed for therapeutic efficacy by determining it ability to reduce the amount of angiogenesis or vasculogenesis in a tumor in a xenograft model.

Therapeutic efficacy can also be assessed in animal models of rheumatoid arthritis e.g., a SKG strain of mouse (Sakaguchi et al.), rat type II collagen arthritis model, mouse type II collagen arthritis model; a mouse model of GVHD (e.g., as described in Trenado (2002)) or a model of ischemic stroke, e.g., aorta/vena cava occlusion, external neck torniquet or cuff, hemorrhage or hypotension, intracranial hypertension or common carotid artery occlusion, two-vessel occlusion and hypotension, four-vessel occlusion, unilateral common carotid artery occlusion (in some species only), endothelin-1-induced constriction of arteries and veins, middle cerebral artery occlusion, spontaneous brain infarction (in spontaneously hypertensive rats), macrosphere embolization, blood clot embolization or microsphere embolization.

Competitive Binding Assays

Assays for determining a Fn14-binding protein that competitively inhibits binding of an antibody of the disclosure will be apparent to the skilled artisan. For example, the antibody of the disclosure is conjugated to a detectable label, e.g., a fluorescent label or a radioactive label. The labeled antibody and the test Fn14-binding protein are then mixed and contacted with Fn14 or an extracellular domain thereof fused to an Fc region of an antibody or a peptide comprising an epitope thereof. The level of labeled antibody is then determined and compared to the level determined when the labeled antibody is contacted with the Fn14 or Fn14-Fc fusion or a peptide comprising an epitope thereof in the absence of the Fn14-binding protein. If the level of labeled antibody is reduced in the presence of the test Fn14-binding protein compared to the absence of the Fn14-binding protein, the Fn14-binding protein competitively inhibits binding of the antibody.

Optionally, the test Fn14-binding protein is conjugated to a different label than the antibody. This permits detection of the level of binding of the test Fn14-binding protein to the protein or epitope.

In another example, the test Fn14-binding protein is permitted to bind to Fn14 or Fn14-Fc fusion or a peptide comprising an epitope thereof prior to contacting the Fn14 or Fn14-Fc fusion or a peptide comprising an epitope thereof with an antibody described herein. A reduction in the amount of bound antibody in the presence of the Fn14-binding protein compared to in the absence of the Fn14-binding protein indicates that the Fn14-binding protein competitively inhibits binding of the antibody to Fn14. A reciprocal assay can also be performed using labeled Fn14-binding protein and first allowing the antibody to bind to Fn14 or Fn14-Fc fusion or a peptide comprising an epitope thereof. In this case, a reduced amount of labeled Fn14-binding protein bound to Fn14 or Fn14-Fc fusion or a peptide comprising an epitope thereof in the presence of the antibody compared to in the absence of antibody indicates that the Fn14-binding protein competitively inhibits binding of the antibody to Fn14.

Affinity Assays

Optionally, the dissociation constant (Kd) or association constant (Ka) or binding constant ($K_D$, i.e., Ka/Kd) of a Fn14-binding protein for Fn14 or an epitope containing peptide thereof is determined. These constants for a Fn14-binding protein is, in one example, measured by a radiolabeled or fluorescently-labeled Fn14-binding assay. This assay equilibrates the Fn14-binding protein with a minimal concentration of labeled Fn14 in the presence of a titration series of unlabeled Fn14. Following washing to remove unbound Fn14, the amount of label is determined. According to another example the constants are measured by using surface plasmon resonance assays, e.g., using BIAcore surface plasmon resonance (BIAcore, Inc., Piscataway, N.J.) with immobilized Fn14 or a region thereof.

Pharmaceutical Compositions and Methods of Treatment

Fn14-binding proteins of the disclosure (syn. active ingredients) are useful for formulations into a pharmaceutical composition for parenteral, topical, oral, or local administration, aerosol administration, or transdermal administration, for prophylactic or for therapeutic treatment. The pharmaceutical compositions can be administered in a variety of unit dosage forms depending upon the method of administration. For example, unit dosage forms suitable for oral administration include powder, tablets, pills, capsules and lozenges.

The pharmaceutical compositions of this disclosure are useful for parenteral administration, such as intravenous administration or subcutaneous administration or administration into a body cavity or lumen of an organ or joint. The compositions for administration will commonly comprise a solution of the Fn14-binding protein of the disclosure dissolved in a pharmaceutically acceptable carrier, such as an aqueous carrier. A variety of aqueous carriers can be used, e.g., buffered saline and the like. The compositions may contain pharmaceutically acceptable carriers as required to approximate physiological conditions such as pH adjusting and buffering agents, toxicity adjusting agents and the like, for example, sodium acetate, sodium chloride, potassium chloride, calcium chloride, sodium lactate and the like. The concentration of Fn14-binding proteins of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

The Fn14-binding protein of the disclosure can be formulated for parenteral administration, e.g., formulated for injection via the intravenous, intramuscular, subcutaneous, transdermal, or other such routes, including peristaltic administration and direct instillation into a tumor or disease site (intracavity administration). The preparation of an aqueous composition that contains the compounds of the present disclosure as an active ingredient will be known to those of skill in the art.

Suitable pharmaceutical compositions in accordance with the disclosure will generally include an amount of the Fn14-binding protein of the present disclosure admixed with an acceptable pharmaceutical carrier, such as a sterile aqueous solution, to give a range of final concentrations, depending on the intended use. The techniques of preparation are generally known in the art as exemplified by Remington's Pharmaceutical Sciences, 16th Ed. Mack Publishing Company, 1980.

Upon formulation, compounds of the present disclosure will be administered in a manner compatible with the dosage formulation and in such amount as is therapeutically/prophylactically effective. Suitable dosages of compounds of the present disclosure will vary depending on the specific compound, the condition to be treated and/or the subject being treated. It is within the ability of a skilled physician to determine a suitable dosage, e.g., by commencing with a sub-optimal dosage and incrementally modifying the dosage to determine an optimal or useful dosage.

Exemplary dosages and timings of administration will be apparent to the skilled artisan based on the disclosure herein.

In some examples, a Fn14-binding protein of the disclosure is administered with, prior to or after treatment for a condition, e.g., cancer. Exemplary treatments include radiation therapy, chemotherapy (e.g., caboplatin, siplatin, cyclophosphamide, docetaxal, doxorubicin, erlotinib, etoposide, fluorouracil, irinotecan, methotrexate, paclitaxel, topotecan, vincristine or vinblastine) or administration of another drug to treat a condition, e.g., a biologic such as rituximab, trastuzumab, bevacizumab, alemtuzumab, panitumumab, or cetuximab.

In one example, a Fn14-binding protein of the disclosure is administered with an appetite stimulant (e.g., a melanocortin-4 receptor antagonist, a ghrelin receptor agonist, megestrol acetate or a cannabinoid), a drug targeting an inflammatory cytokine (e.g., a TNF antagonist (e.g., etanercept, adalimumab, golimumab, infliximab), an anti-IL-6 antibody (e.g., CNTO-328, ALD-518), a β-adrenoreceptor antagonist, an anabolic steroid, myostatin, an ACE inhibitor or eicosapentaenoic acid).

Diagnostic/Prognostic Assays

It will be apparent from the description herein that the present disclosure provides various methods for diagnosing/prognosing conditions associated with Fn14 expression.

Protein Detection Assays

One example of the disclosure detects the presence of Fn14 or a cell expressing same. The amount, level or presence of a protein or cell is determined using any of a variety of techniques known to the skilled artisan such as, for example, a technique selected from the group consisting of flow cytometry, immunohistochemistry, immunofluorescence, an immunoblot, a Western blot, a dot blot, an enzyme linked immunosorbent assay (ELISA), radioimmunoassay (RIA), enzyme immunoassay, fluorescence resonance energy transfer (FRET), matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or protein chip technology.

In one example, the assay used to determine the amount or level of a protein is a semi-quantitative assay.

In another example the assay used to determine the amount or level of a protein is a quantitative assay.

For example, the protein is detected with an immunoassay, e.g., using an assay selected from the group consisting of, immunohistochemistry, immunofluorescence, enzyme linked immunosorbent assay (ELISA), fluorescence linked immunosorbent assay (FLISA), Western blotting, radioimmunoassay (RIA), a biosensor assay, a protein chip assay and an immunostaining assay (e.g. immunofluorescence).

Standard solid-phase ELISA or FLISA formats are particularly useful in determining the concentration of a protein from a variety of samples.

In one form, an ELISA or FLISA comprises of immobilizing a Fn14-binding protein of the disclosure or a protein that binds to a different epitope of Fn14 on a solid matrix, such as, for example, a membrane, a polystyrene or polycarbonate microwell, a polystyrene or polycarbonate dipstick or a glass support. A sample is then brought into physical relation with the immobilized protein, Fn14 is bound or 'captured'. The bound Fn14 is then detected using a second labeled compound that binds to a different epitope of Fn14 (e.g., the Fn14-binding protein of the disclosure). Alternatively, a third labeled antibody can be used that binds the second (detecting) antibody.

It will be apparent to the skilled person that the assay formats described herein are amenable to high throughput formats, such as, for example automation of screening processes or a microarray format. Furthermore, variations of the above-described assay will be apparent to those skilled in the art, such as, for example, a competitive ELISA.

In an alternative example, a polypeptide is detected within or on a cell, using methods known in the art, such as, for example, immunohistochemistry or immunofluorescence. Methods using immunofluorescence are exemplary, as they are quantitative or at least semi-quantitative. Methods of quantitating the degree of fluorescence of a stained cell are known in the art and described, for example, in Cuello, 1984.

Biosensor devices generally employ an electrode surface in combination with current or impedance measuring elements to be integrated into a device in combination with the assay substrate (such as that described in U.S. Pat. No. 5,567,301). A Fn14-binding protein of the disclosure is incorporated onto the surface of a biosensor device and a biological sample contacted to said device. A change in the detected current or impedance by the biosensor device indicates protein binding to said Fn14-binding protein. Some forms of biosensors known in the art also rely on surface plasmon resonance to detect protein interactions, whereby a change in the surface plasmon resonance surface of reflection is indicative of a protein binding to a ligand or antibody (U.S. Pat. Nos. 5,485,277 and 5,492,840).

Biosensors are of particular use in high throughput analysis due to the ease of adapting such systems to micro- or nano-scales. Furthermore, such systems are conveniently adapted to incorporate several detection reagents, allowing for multiplexing of diagnostic reagents in a single biosensor unit. This permits the simultaneous detection of several proteins or peptides in a small amount of body fluids.

Imaging Methods

As will be apparent to the skilled artisan from the foregoing, the present disclosure also contemplates imaging methods using a Fn14-binding protein of the disclosure. For imaging, a Fn14-binding protein is generally conjugated to a detectable label, which can be any molecule or agent that can emit a signal that is detectable by imaging. However, a secondary labeled compound that specifically binds to a Fn14-binding protein of the disclosure may also be used. Exemplary detectable labels include a protein, a radioisotope, a fluorophore, a visible light emitting fluorophore, infrared light emitting fluorophore, a metal, a ferromagnetic substance, an electromagnetic emitting substance a substance with a specific magnetic resonance (MR) spectroscopic signature, an X-ray absorbing or reflecting substance, or a sound altering substance.

The Fn14-binding protein of the disclosure (and, if used the labeled secondary compound) can be administered either systemically or locally to an organ, or tissue (or tumor, in the case of a cancer) to be imaged, prior to the imaging procedure. Generally, the Fn14-binding protein is administered in doses effective to achieve the desired optical image of a tumor, tissue, or organ. Such doses may vary widely, depending upon the particular Fn14-binding protein employed, condition to be imaged, tissue, or organ subjected to the imaging procedure, the imaging equipment being used, and the like.

In some examples of the disclosure, the Fn14-binding protein is used as in vivo optical imaging agents of tissues and organs in various biomedical applications including, but not limited to, imaging of tumors, tomographic imaging of organs, monitoring of organ functions, coronary angiography, fluorescence endoscopy, laser guided surgery, photoacoustic and sonofluorescence methods, and the like.

Examples of imaging methods include magnetic resonance imaging (MRI), MR spectroscopy, radiography, computerized tomography (CT), ultrasound, planar gamma camera imaging, single-photon emission computed tomography (SPECT), positron emission tomography (PET), other nuclear medicine-based imaging, optical imaging using visible light, optical imaging using luciferase, optical imaging using a fluorophore, other optical imaging, imaging using near infrared light, or imaging using infrared light.

In some examples, an imaging agent is tested using an in vitro or in vivo assay prior to use in humans, e.g., using a model described herein.

Samples

To the extent that the method of the present disclosure is performed in vitro, on an isolated tissue sample, rather than as an in vivo based screen, reference to "sample" should be understood as a reference to any sample of biological material derived from an animal such as, but not limited to, a body fluid (e.g., blood or synovial fluid or cerebrospinal fluid), cellular material (e.g. tissue aspirate), tissue biopsy specimens or surgical specimens.

The sample which is used according to the method of the present disclosure may be used directly or may require some form of treatment prior to use. For example, a biopsy or surgical sample may require homogenization or other form of cellular dispersion prior to use. Furthermore, to the extent that the biological sample is not in liquid form, (if such form is required or desirable) it may require the addition of a reagent, such as a buffer, to mobilize the sample.

As will be apparent from the preceding description, such an assay may require the use of a suitable control, e.g. a normal or healthy individual or a typical population, e.g., for quantification.

As used herein, the term "normal individual" shall be taken to mean that the subject is selected on the basis that they do not have abnormal numbers of Fn14 expressing cells or abnormal levels of Tweak.

A "healthy subject" is one that has not been diagnosed as suffering from a condition, e.g., an Fn14-mediated condition and/or is not at risk of developing the condition.

Fn14-Mediated Conditions

The present disclosure encompasses the use of a Fn14-binding protein or antibody or composition described herein to treat any Fn14-mediated condition. Exemplary conditions include cancer, metastasis, excessive vascularization or angiogenesis, an autoimmune disease, an inflammatory disease, a neurodegenerative diseases, keloid scarring, graft versus host disease, graft rejection or ischemia.

In one example, the Fn14-mediated condition is an inflammatory disease or an autoimmune disease. In one example, the condition is a connective tissue disease (including inflammatory arthritis, such as rheumatoid arthritis, psoriatic arthritis, reactive arthritis or gout), lupus (including systemic lupus erythematosus), type 1 diabetes, multiple sclerosis, vasculitis (including Wegener's granulomatosis and Henoch Schonlein Syndrome), nephritis (including glomerulonephritis and pneumonitis), atherosclerosis or inflammation of the eye (including uveitis).

In one example, the autoimmune condition is multiple sclerosis, neuritis, polymyositis, psoriasis, vitiligo, Sjogren's syndrome, arthritis (such as rheumatoid arthritis), Type 1 diabetes, autoimmune pancreatitis, inflammatory bowel diseases, Crohn's disease, ulcerative colitis, celiac disease, glomerulonephritis, scleroderma, sarcoidosis, autoimmune thyroid diseases, Hashimoto's thyroiditis, Graves disease, myasthenia gravis, Addison's disease, autoimmune uveoretinitis, pemphigus vulgaris, primary biliary cirrhosis, pernicious anemia, or systemic lupus erythematosis (SLE). In one example, the condition is rheumatoid arthritis or SLE.

In one example, the condition is a connective tissue disease, such as rheumatoid arthritis. In this regard, Dharmapatni et al., (2011) have shown that Tweak/Fn14 play a role in rheumatoid arthritis.

In one example, the condition is scleroderma (including systemic scleroderma).

In another example, the condition is graft rejection (e.g., allograft rejection) or graft versus host disease (including weight loss associated with graft versus host disease). In this regard, Tweak/Fn14 have been show to play a role in pathogenesis of graft versus host disease, e.g., by Zhao et al., (2007).

In another example, the condition is cardiac allograft vasculopathy.

In one example, the condition is graft rejection associated intimal thickening.

In another example the condition is intramyocardial infarction or ischemic repurfusion injury. In this regard, Tweak/Fn14 has been shown to play a role in ischemia by, e.g., Frauenknecht et al., (2010) and Inta et al., (2008).

In another example, the condition is associated with excessive angiogenesis and/or neovascularization, e.g., cancer (including solid tumors, leukemias, lymphoma, melanoma, glioma, breast cancer, colonic cancer, gastric cancer, esophageal cancer, renal cell cancer, ovarian cancer, cervical cancer, carcinoid cancer, testicular cancer, prostate cancer, head and neck cancer and hepatocellular carcinoma), cancer metastasis, cancer neovascularization, autoimmune disease (including psoriasis), nephropathy, retinopathy, preeclampsia, hepatitis, sepsis and macular degeneration.

In one example, the condition is cancer or a metastasis thereof. The term "cancer" refers to or describes the physiological condition in mammals that is typically characterized by unregulated cell growth/proliferation. Examples of cancer include, but are not limited to, an adenocarcinoma, a squamous cell carcinoma, a digestive/gastrointestinal cancer, an endocrine cancer, an eye cancer, a musculoskeletal cancer, a breast cancer, a neurologic cancer, a genitourinary cancer, a germ cell cancer, a head and neck cancer, a hematologic/blood cancer, a respiratory cancer, a skin cancer, an AIDS-related malignancy or a gynelogic cancer.

An adenocarcinoma is a cancer of an epithelium that originates in glandular tissue. Exemplary adenocarcinomas include forms of colorectal cancer, lung cancer, cervical cancer, prostate cancer, urachus cancer, vulval cancer, breast cancer, esophageal cancer, pancreatic cancer and gastric cancer.

Digestive/gastrointestinal cancers include anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including childhood hepatocellular (liver) cancer; pancreatic cancer including childhood pancreatic cancer; sarcoma, rhabdomyosarcoma; rectal cancer; and small intestine cancer.

Endocrine cancers include islet cell carcinoma (endocrine pancreas); adrenocortical carcinoma including childhood adrenocortical carcinoma; gastrointestinal carcinoid tumor; parathyroid cancer; pheochromocytoma; pituitary tumor; thyroid cancer including childhood thyroid cancer; childhood multiple endocrine neoplasia syndrome; and childhood carcinoid tumor.

Eye cancers include intraocular melanoma; and retinoblastoma.

Musculoskeletal cancers include Ewing's family of tumors; osteosarcoma/malignant fibrous histiocytoma of the bone; rhabdomyosarcoma including childhood rhabdomyosarcoma; soft tissue sarcoma including childhood soft tissue sarcoma; clear cell sarcoma of tendon sheaths; and uterine sarcoma.

Neurologic cancers include childhood brain stem glioma; brain tumor; childhood cerebellar astrocytoma; childhood cerebral astrocytoma/malignant glioma; childhood ependymoma; childhood medulloblastoma; childhood pineal and supratentorial primitive neuroectodermal tumors; childhood visual pathway and hypothalamic glioma; other childhood brain cancers; adrenocortical carcinoma; central nervous system lymphoma, primary; childhood cerebellar astrocytoma; neuroblastoma; craniopharyngioma; spinal cord tumors; central nervous system atypical teratoid/rhabdoid tumor; central nervous system embryonal tumors; and supratentorial primitive neuroectodermal tumors including childhood and pituitary tumor.

Genitourinary cancers include bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor;

Germ cell cancers include childhood extracranial germ cell tumor; extragonadal germ cell tumor; ovarian germ cell tumor; and testicular cancer.

Head and neck cancers include lip and oral cavity cancer; childhood oral cancer; hypopharyngeal cancer; laryngeal cancer including childhood laryngeal cancer; metastatic squamous neck cancer with occult primary; mouth cancer; nasal cavity and paranasal sinus cancer; nasopharyngeal cancer including childhood nasopharyngeal cancer; oropharyngeal cancer; parathyroid cancer; pharyngeal cancer; salivary gland cancer including childhood salivary gland cancer; throat cancer; and thyroid cancer.

Hematologic/blood cell cancers include leukemia (e.g., acute lymphoblastic leukemia in adults and children; acute myeloid leukemia, e.g., in adults and children; chronic lymphocytic leukemia; chronic myelogenous leukemia; and hairy cell leukemia); a lymphoma (e.g., AIDS-related lymphoma; cutaneous T-cell lymphoma; Hodgkin's lymphoma including Hodgkin's lymphoma in adults and children; Hodgkin's lymphoma during pregnancy; non-Hodgkin's lymphoma including non-Hodgkin's lymphoma in adults and children; non-Hodgkin's lymphoma during pregnancy; mycosis fungoides; Sezary syndrome; Waldenstrom's macroglobulinemia; and primary central nervous system lymphoma); and other hematologic cancers (e.g., chronic myeloproliferative disorders; multiple myeloma/plasma cell neoplasm; myelodysplastic syndromes; and myelodysplastic/myeloproliferative disorders).

Respiratory cancers include non-small cell lung cancer; small cell lung cancer; malignant mesothelioma including malignant mesothelioma in adults and children; malignant thymoma; childhood thymoma; thymic carcinoma; bronchial adenomas/carcinoids including childhood bronchial adenomas/carcinoids; pleuropulmonary blastoma.

Skin cancers include Kaposi's sarcoma; Merkel cell carcinoma; melanoma; basal cell carcinoma and childhood skin cancer.

In a further example, the condition is a wasting disorder, such as cachexia as described in more detail herein. In one example, the wasting disorder is associated with a condition, such as, cancer, metabolic acidosis, infectious diseases, diabetes, autoimmune immune deficiency syndrome (AIDS), autoimmune disorders, addiction to drugs, cirrhosis of the liver, chronic inflammatory disorders, anorexia, chronic heart failure, chronic kidney disease, osteoporosis, skeletal muscle disease, motor neuron disease, multiple sclerosis, muscle atrophy and neurodegenerative disease.

In one example, the wasting disorder is cachexia or sarcopenia (e.g., wasting associated with aging).

In one example, the wasting disorder is cachexia.

In one example, the cachexia is associated with cancer, infectious disease (e.g., tuberculosis or leprosy), AIDS, autoimmune disease (including rheumatoid arthritis or type 1 diabetes), cystic fibrosis, drug addiction, alcoholism or liver cirrhosis.

In one example, the cachexia is associated with an autoimmune disease. In one example, the cachexia is associated with rheumatoid arthritis. In one example, the cachexia is associated with type 1 diabetes.

In one example, the cachexia is associated with cardiac disease.

In one example, the cachexia is associated with chronic kidney disease.

In one example, the cachexia is associated with chronic pulmonary inflammation.

In one example, the cachexia is associated with instestinal inflammation.

In one example, the cachexia is associated with inflammatory bowel disease.

In one example, the cachexia is associated with aging.

In one example, the cachexia is associated with sepsis.

In one example, the cachexia is associated with AIDS.

In one exemplary form of the present disclosure the wasting disorder is cachexia associated with cancer. Exemplary cancers are described supra.

In one example, the method additionally comprises identifying a subject suffering from cachexia. Such a subject can be identified, for example, based on detection of unintentiaonal weight loss following diagnosis of another condition (e.g., cancer). For example, the subject can lose at least 5% of their body weight following diagnosis of another condition (e.g., cancer) or within the previous 30 days.

Kits

The present disclosure also provides therapeutic/prophylactic/diagnostic kits comprising compounds of the present disclosure for use in the present detection/isolation/diagnostic/prognostic/treatment/prophylactic methods. Such kits will generally contain, in suitable container means, a Fn14-binding protein of the present disclosure. The kits may also contain other compounds, e.g., for detection/isolation/diagnosis/imaging or combined therapy. For example, such kits may contain any one or more of a range of anti-inflammatory drugs and/or chemotherapeutic or radiotherapeutic drugs; anti-angiogenic agents; anti-tumor cell antibodies; and/or anti-tumor vasculature or anti-tumor stroma immunotoxins or coaguligands or vaccines.

In one example, the kit is for detecting Fn14 and additionally comprises a reagent to facilitate detection (a detectable label and/or a substrate of a detectable label. Such kits may additionally comprise a positive control.

In another example, the kit is for isolating a cell or a population of cells. In such kits a Fn14-binding protein of the disclosure may be labeled with a detectable label to facilitate FACS. The Fn14-binding protein may also be labeled with a magnetic or paramagnetic particle to facilitate MACS. The Fn14-binding protein may also be immobilized on a solid or semi-solid substrate to facilitate isolation.

In a further example, the kit is for treatment or prevention of a condition. In such kits, the Fn14-binding protein may be provided in solution or in a lyophilized form, optionally with a solution for resuspension. The Fn14-binding protein may be conjugated to a therapeutic compound or the kit may include a therapeutic compound for conjugation thereto. As discussed above, the kit may also comprise additional therapeutic or prophylactic compounds.

The present disclosure includes the following non-limiting examples.

Methods i) Phage Display Library

The phage display library was prepared and expanded using similar techniques to the methods described in detail by Hans de Haard (1999).

ii) Selection of Human Fabs from the Phage Library Specific for hFn14

One phage aliquot of the phage library (>1012 phage per ml) was used for selection of human Fabs specific for the ectodomain of hFn14. Several rounds of selection in solution using magnetic beads and on solid phase using microtitre plates was performed using a combination of His-Tagged hFn14 and Fc-tagged hFn14 to enrich for hFn14 specific hFabs. The Fc-tag allowed attachment of the Fn14-Fc antigen to Protein A/G beads and the phage library was allowed to incubate in solution.

For the first round of panning 1 ml of 10 m/ml solution of Fn14-Fc was allowed to incubate with 50 µl (pre-washed 3 times in PBS) protein A dynabeads (Invitrogen) in PBS containing 5% milk powder for 1 hour at room temperature with gentle mixing. The phage library was pre-absorbed with the protein A beads to remove any Fabs which could bind strongly to the beads by incubating 0.5 ml of the phage library with 50 µl pre-washed beads for 20 mins with gentle mixing. Excess or unbound antigen was removed by placing the tube on a magnet allowing the beads to settle to the bottom of the tube and removing the wash solution by pipetting. The beads were resuspended with 1-2 mls of PBS, mixed and the process repeated twice. The washed beads coupled with Fn14-Fc were then incubated with the pre-absorbed phage library in PBS containing 5% milk for 1-2 hours mixing at room temperature. After 1-2 hours the unbound Fabs were removed by washing the beads as above five times with PBS containing 0.1% Tween20 (PBST) and once with PBS. The bound Fabs were eluted from the beads by adding 1 ml 0.1M Glycine pH2.2 for 10 minutes for the last minute the solution was placed on the magnet and the eluted phage was equilibrated with 1.5M Tris solution. An aliquot of the phage (0.75 ml) was allowed to re-infect a 10 ml stationary culture of log phase TG1 cells for 30 minutes at 37° C. Then the culture was rescued by adding 1013 helper phage for 30 minutes at 37° C. gently mixing and leaving the culture stationary. The re-infected rescued culture was amplified by adding to 200 ml 2YT/Carb/Kan and incubating overnight at 37° C. The next day the culture was centrifuged at 8000 rpm for 10 minutes and the supernatant removed for PEG precipitation. 50 mls of PEG solution was added the solution mixed and incubated on ice at 4° C. for 2 hours. The mixture was centrifuged at 10,000 rpm for 30 minutes and the phage pellet was resuspended in 1 ml of PBS. This was centrifuged and the 0.5 ml of the phage supernatant used for the next round of panning. The remaining phage was stored in 20% Glycerol at −80° C.

The procedure above was repeated for subsequent rounds of panning alternating between use of protein A beads and protein G beads to further reduce the chances of isolating non-specific binding Fabs. The amount of Fn14-Fc antigen for subsequent rounds was reduced to 5 µg/ml and the washing stringency was increased per round in attempt to isolate the higher affinity Fabs specific for Fn14 from the phage library. Twelve PBST washes for round 2, twenty in round 3, thirty in round 4 and round 5, and for each round a final wash in PBS prior to elution was performed.

A further 2 rounds of panning were performed using Fn14-His, to ensure Fabs would be selected against the ectodomain of Fn14 and not to the Fc tag. The same procedure was used except Fn14-His antigen was coated onto ten wells (100 µl/well) of a Maxisorp microtiter plate at 5 µg/ml for 1 hour, the wells were washed 3 times to remove unbound antigen with 200 µl PBS, plates tapped dry and blocked with PBS containing 5% milk powder for 1 hour. Phage from round 5 was incubated with the Fn14-His coated and blocked wells for 2 hours, and the wells were washed twenty-five times with PBST and twice with PBS, the phage was eluted by adding 100 µl per well of Glycine buffer as described above. The phage was reinfected, rescued and amplified as described above for the previous rounds.

iii) Analysis of Single Clones

To identify individual Fab clones with high reactivity to hFn14 single clones were isolated from rounds 5-7 and the binding assessed by ELISA. The heavy chain of individual clones was sequenced and clones with different $V_H$ sequences were analysed further. Clones with different Fab sequences were sub-cloned into an *E. coli* expression vector to remove the phage framework and assess the reactivity of soluble Fabs to Fn14.

a) Single clone ELISA

Phage pools from round 7 were re-infected by incubating with log-phase TG1 cells as described above and plated onto 2YT/Carb/2% Glu solid media (2YTmedia containing 15 g bactoagar). Twenty four single colonies were picked and used to inoculate 10 ml 2YT/Carb/2% Glu media, which was allowed to incubate shaking overnight at 37° C. The next day 50 µl of the overnight cultures was used to inoculate 10 ml 2YT/Carb media and the cultures were allowed to grow to log-phase. The cultures were allowed to settle and 10 µl of helper phage was added to rescue the phage and incubated as above. 200 µl of the rescued phage preparations were used to inoculate fresh 10 ml 2YT/Carb/Kan cultures and allowed to incubate at 37° C. overnight in a shaking incubator. The phage was harvested by spinning the culture and PEG precipitation as described above. Pellets were resuspended in 1 ml PBS.

To analyse the binding of individual phage clones an ELISA was performed. Wells of a maxisorp microtitre plate were coated with (100 µl per well) 2 µg/ml Fn14-Fc, Fn14-His, 9E10 (anti-Myc tag) and a control antigen, for 1 hour. Unbound antigen was washed twice with PBS (200 µl/well) and wells were blocked with PBS containing 5% milk powder for 2 hours. The wells were washed twice with PBS and phage single colony preparations were allowed to incubate (100 µl/well) for 1 hour on the plate shaker. The plate was washed 5 times with PBST and 100 µl/per well of goat anti-human kappa chain antibody conjugated to horse radish peroxidise (HRP; Bethyl labs, US) at 0.25 µg/ml in PBST was added to the wells for 1 hour shaking. A further 5 washes with PBST and one wash with PBS was performed and the ELISA was developed by adding 100 µl per well of 3,3',5,5'-Tetramethylbenzidine (TMB, Pierce) and allowing the colour to develop. To stop the reaction, 50 µl per well of 2M H2SO4 was added and the absorbance readings measured at 450 nM in a plate reader (Spectromax).

b) DNA Sequencing

Individual colonies from rounds 5-7 were picked and placed into PCR tubes containing 50 µl sterile milli Q water. Primarily $V_H$ sequencing was performed to identify novel clones followed by $V_L$ sequencing. PCR reactions were set up to individually amplify the variable heavy chain ($V_H$) and variable kappa light chain ($V_L$) using the following conditions. Template DNA (5 µl of the colony mix), 1×PCR buffer, 10 mM DNTP's, 1 mMol suitable primers, 0.5 µl Amplitaq (Life Technologies), using the following amplification cycle, 94° C. 10 minutes, 30 cycles of 94° C. 30 seconds, 60° C. 30 seconds, 72° C. 1 minute, then a final 7 minute 72° C. extension time. PCR reactions were run out on 1% Agarose gels to identify amplified $V_H$ and $V_L$. PCR reactions were purified using Qiagen PCR clean up kit and purified DNA was sequenced by AGRF facility (WEHI, Melbourne).

c) Sub-Cloning to pGC *E. coli* Expression Vector

Positive clones were sub-cloned into an *E. coli* expression vector pGC (a derivative of pUC18) to remove the phage framework (Coia et al., 1996). Positive clones were expressed, purified and characterised for binding specifically to hFn14

Cultures were grown by inoculating 5 ml LB/Carb (LB: 10 g Tryptone, 5 g Yeast extract, 10 g Sodium chloride pH 7.5) with a colony and incubating at 37° C. overnight in a shaking incubator. Cells were pelleted by centrifugation at 8,000 rpm for 5 minutes and the DNA was extracted using a Qiagen Miniprep kit. A restriction enzyme digest was performed to remove the Fab ($V_H$ and $V_L$ region) from pCES1 vector using AflIII restriction enzyme. This AflIII site is compatible in pGC vector and also allows the signal sequence for the $V_L$ gene to be transferred into pGC to form a bicistronic vector, allowing co-expression of $V_L$ and $V_H$ genes to form Fabs. 1-2 µg of DNA was digested with 0.5-1 µl AflIII and 0.5 µl NotI, in the presence of 1× restriction enzyme buffer and 100 µg/ml bovine serum albumin (BSA) for 2 hours at 37° C. The digested pGC and Fab fragments were gel extracted and purified using a Qiagen gel extraction kit and a ligation reaction was set-up using a 3:1 molar ratio of insert:vector DNA and 1 µl T4 DNA ligase (NEB labs), overnight at 16° C. Ligation reactions were desalted using the Qiagen PCR clean up kit and 2 ml of the ligation reactions were transformed into chemically competent *E. coli* XL1blue cells according to the manufacturers recommended protocol (Stratagene). Following the gene expression period cells were pelleted and plated out on 2YT/Carb/ 2% Glu plates. PCR was performed on the colonies for the presence of Fab, using the same conditions as described above. Minipreps were prepared of the positive clones as described above and sent for DNA sequencing to confirm correct sequences of individual Fab clones.

iv) Expression of hFab Clones

Fabs were transformed into TG1 cells for protein expression. A single colony was used to inoculate 10 ml 2YT/Carb/2% Glu media and was cultured in a shaking incubator overnight at 37° C. For small scale expression, 10 µl of the overnight culture was added to fresh tube containing 10 ml 2YT/Carb and for large scale 0.5 ml was added to 0.5 L 2YT/Carb and cultured until late log phase (OD600 approximately 0.9-1.0). For the large scale culture, 1 mM Isopropyl thiogalactose (IPTG) and fresh antibiotic was added to the culture and for the 10 ml culture fresh 2YT/Carb/IPTG media was added to the pelleted culture. Cultures were incubated at 30° C. overnight in a shaking incubator. The cultures were spun at 8,000 rpm for 10 minutes and the supernatants removed. A sample of the supernatant was retained for analysis. The pellets were placed on ice and resuspended in cold periplasmic extraction buffer (0.1M Tris, 20% sucrose, 1 mM EDTA pH8) for 30 minutes on ice, to minimise degradation a complete protease inhibitor cocktail was added to the mix according to the manufacturers recommended protocol (Roche). The extract was centrifuged at 15,000 rpm for 15 minutes and the supernatant containing the periplasmic extract was filtered and stored at 4° C. An ELISA was performed to ensure the periplasmic preparations of hFab clones were functional and bound to Fn14-His and/or Fn14-Fc, using the same method as described above.

v) Purification of hFabs a) Affinity Purification Using Ni-NTA

Periplasmic extracts (large scale) were purified using Ni-NTA agarose (Qiagen) affinity chromatography via the 6× Histidine tag at the C-terminus of the hFab. Periplasmic extracts were dialysed into PBS with 3 buffer changes to remove the sucrose and EDTA. The dialysed material was diluted ½ in PBS containing 0.5M sodium chloride; PBS/NaCl). The resin (1-5 ml) was washed into PBS/NaCl and allowed to incubate with the periplasmic extract for 1-2 hours or overnight at 4° C. on a rotator. The periplasmic/resin mixture was poured into an empty column allowed to settle and the periplasmic preparation was allowed to flow through the column slowly. The flow through fraction was collected for analysis. The column was eluted in a competitive step-wise manner by adding increasing concentrations of Imidazole (20 mM, 50 mM and 250 mM) which competes for the Histidine tag. The column was washed with 30-50 ml PBS/NaCl containing 20 mM Imidazole, followed by 50 mM Imidazole and finally 10 ml of 250 mM Imiadazole. All fractions were collected and analysed by SDS-PAGE. Fractions containing purified hFab were dialysed into PBS with 3 buffer changes and concentrated using a Centricon concentrator 10 kDa cut-off (Millipore).

b) Gel Filtration of hFabs

To further purify hFabs to remove any bacterial impurities, aggregates and breakdown products gel filtration chromatography was performed using an FPLC 200 ml Superose S-200HR (GE) column run in PBS at 0.4 ml/minute on an Agilent FPLC. Fractions were collected and analysed for purity on SDS-PAGE. Fractions containing pure hFab were pooled and concentrated as above.

vi) Affinity Maturation of Clone 6.5 hFab

The process of light chain shuffling is an established successful method for affinity maturation of Fabs (Marks et al., 1992). This involves isolating the optimal $V_L$ chain from the original gene pool to pair with a specific $V_H$ chain. In order to carry out this process the $V_H$ gene pool from the library is replaced with the specific $V_H$ (i.e clone 6.5) and is paired with each member of the phage display $V_L$ library pool. A stringent selection process should be performed to identify the highest binding mutants to hFn14.

A maxi-preparation of the phage display library DNA was prepared according to the manufacturer's instructions (Qiagen Maxi-prep kit). The $V_H$ chain library was sequentially digested SfiI and NotI restriction enzymes and replaced by 6.5 $V_H$ clone. The final digests were gel extracted and a ligation reaction was performed to introduce the 6.5 $V_H$ fragment, using similar methods as described previously. To prepare the light chain library twenty transformations were performed pooled and the library expanded using the method described above. Phage aliquots and glycerol stocks of the library were prepared. DNA sequencing was performed to ensure the correct $V_H$ sequence was inserted and individual clones contained a good variety of $V_L$ chains. The final library size was established by titering the transformed pool 3 times prior to amplification.

To select for higher affinity clones 4 rounds of panning were performed: 2 rounds with Fn14-Fc and 2 further rounds with Fn14-His using similar methods as described above, except 15 washes were performed with PBST in rounds 3 and 4 followed by 2 PBS washes. An ELISA was performed to monitor the panning success, single clones in rounds 4-6 were analysed individually for binding to hFn14, the highest binders were analysed further and all clones were DNA sequenced using methods described previously.

vii) Affinity measurement

The affinity of wildtype Fab clone 6.5 and the light chain shuffled mutants was measured by surface Plasmon resonance (SPR) using the ProteOn XPR36™ instrument (Bio-Rad). Individual channels of a six channel GLC chip were coupled with the relevant hFab ligand at 5 µg/ml in 0.1M sodium acetate buffer pH 4.5 using amine coupling according to the manufacturer's instructions. Five dilutions of analyte hFn14-Fc were prepared in PBS containing 0.005% Tween20 (running buffer) and allowed to flow over the coupled hFab at 30 sec/min flow rate for 500 seconds to evaluate the "on rate" (ka). This was followed by flow with the running buffer for 1200 seconds to evaluate the "off rate" (kd). This process was repeated until the analyte dilution series allowed a good kinetic fit using the Langmuir statistical model for analysing the ka and kd, where the affinity constant (KD) is the kd/ka. The best fit data was analysed using the ProteOn software measured by Chi2, where the lowest value is the best fit of the model to the SPR binding curves. For all affinity measurements the data with a Chi2 value of <5, showing a good fit was used in this analysis.

viii) Reformating hFab Clones to IgG1 and IgG4

The $V_L$ and $V_H$ genes of select affinity matured hFab clones were sub-cloned into the plasmids pFUSEss-CHIg-hG1, pFUSEss-CHIg-hG4 and pFUSE2ss-CLIg-hk (InvivoGen) for generation of whole human IgG1 and IgG4 antibodies. Oligonucleotides were designed to introduce the relevant restriction sites into the N' and C'-terminal ends of the variable heavy ($V_H$) or variable light ($V_L$) chains suggested in the manufacturer's protocol. The fragments were amplified using the relevant forward and reverse primers by PCR using the same conditions as for DNA sequencing above (section iii. b). Plasmids and PCR products were digested and ligated with the relevant restriction enzymes using a similar protocol described in section iv. C. Ligation products were transformed into chemically competent DH5α cells by standard heat shock method. For $V_H$ cloning low salt LB agar (10 g Tryptone, 5 g Yeast extract, 5 g sodium chloride, 15 g bactoagar) with Zeocin resistance (25 µg/ml) was used for plating transformed colonies and for VL low salt LB agar with Blasticidin S resistance at 10 µg/ml. Transformants were analysed by PCR and DNA sequencing to confirm presence of the correct in-frame $V_H$ or $V_L$ chain (AGRF sequencing facility, WEHI). To synthesise transfection-grade DNA, Maxiprep's (Qiagen) were performed.

Co-transfection of $V_H$Ig1 or $V_H$Ig4 and $V_L$Igkappa was carried out using the recommended 2:3 ratio in HEK-293T cells using Lipofectamine 2000 (Invitrogen). Hek293T cells were cultured in DMEM complete media: 5% fetal calf serum, 1× penicillin/streptomycin (pen/strep; Life technologies) and 1× GlutaMAX (4 mM final concentration) at 37° C. in the presence of 5% CO2. Cells were seeded at 3×106 on 25 cm plates in complete DMEM media for 24 hours. 20 µg of a 3:2 ratio of $V_H$:$V_L$ DNA was mixed with 1.6 ml pre-warmed incomplete DMEM media (no additives) for 20 minutes. Concurrently 1.6 ml incomplete DMEM plus 40 µl Lipofectamine 2000 was mixed in a separate tube and incubated. The DNA and lipofectamine were then mixed together and incubated for 30 minutes and 10 mls of pre-warmed incomplete DMEM was added to the mixture. The complete DMEM media was carefully aspirated from the cells and the 5 ml DNA/lipofectamine mixture was poured carefully onto the plate. The cells were returned to the incubator for 4-6 hours after which the media was aspirated and 25 ml s of complete DMEM added. Approximately 24 hours later the media was changed to CD 293 AGT™ media (Gibco) containing pen/strep and GlutaMAX to promote the optimal growth of 293 cells. After 3-4 days the media supernatant was harvested, cells pelleted at 4000 rpm for 5 minutes and the supernatant filtered with a 0.2 µm disk filter. The supernatant was purified using MabSelect Protein A resin (GE) using the manufacturers recommended instructions and analysed for the presence of full length IgG by SDS-PAGE and reactivity to hFn14 analysed by ELISA.

ix) Expression and Purification of R58A mutant Fn14

Recombinant human Fn14 R58A mutant (SEQ ID NO: 82) was expressed as a His-tagged fusion protein from pET-15b in Shuffle T7 Express *E. coli* (New England BioLabs). Expression was induced by 1 mM IPTG at 30° C. for four hours. Pellets were lysed (137 mM NaCl, 2.7 mM KCl, 10 mM $Na_2PO_4$, 2 mM $KH_2PO_4$, 0.67 mg/ml lysozyme, pH7.4) and cleared lysate was loaded onto a 0.5 ml $Ni^{2+}$-nitrilotriacetic acid ($Ni^{2+}$-NTA)-agarose (Qiagen) column equilibrated with binding buffer (137 mM NaCl, 2.7 mM KCl, 10 mM $Na_2PO_4$, 2 mM $KH_2PO_4$, pH7.4). The column was first washed with 10 ml of binding buffer and recombinant proteins were eluted by 250 mM imidazole. Purified protein was buffer exchanged into binding buffer using Nanosep 3K centrifuge filter (Pall).

x) Analytical Gel Filtration Chromatography

The human Fn14 R58A protein was further purified by gel filtration. Protein samples were loaded onto a Superdex200 10/300 GL column (GE Healthcare) equilibrated with PBS (137 mM NaCl, 2.7 mM KCl, 10 mM $Na_2PO_4$, 2 mM $KH_2PO_4$, pH8) at room temperature and were chromatographed at a flow rate of 0.4 ml/min on an ÄKTAxpress system (GE Healthcare). Elution profile detected at 280 nm and 0.5 ml fractions were collected.

xi) ELISA Screening of antibody Binding to Human Fn14 R58A Mutant

The wells of Maxisorp immunoplates (Nunc) were coated overnight at 4° C. with 1 µg/ml of purified human Fn14 R58A mutant. The plates were blocked with 5% milk in phosphate-buffered saline (PBS) for 2 hours at room temperature. Plates were washed with PBST (PBS [137 mM NaCl, 2.7 mM KCl 10 mM $Na_2PO_4$, 2 mM $KH_2PO_4$, pH7.4], 0.1% Triton-x 100). Antibodies were serially diluted (0.5-0.008 µg/ml) in PBS, added to the plate and incubated at room temperature for 1.5 hours. After washing with PBST, human antibodies were incubated with goat anti-human at 2 µg/ml while mouse antibodies were incubated in PBST for 1 hr. After washing, a 1:15,000 dilution of peroxidase-conjugated goat anti-mouse IgG (H+L) or rabbit anti-goat IgG (H+L) (Sigma) was added for 1 hour at room temperature. ELISAs were developed using TMB substrate and the reaction was stopped using 2 M $H_2SO_4$ solution. Optical density at 450 nm was quantified using a Spectramax absorbance spectrophotometer.

xii) Expression and Purification of antibodies

Where antibodies were generated from hybridomas (antibodies designated herein as 001, 002, 004 and ITEM1), approximately 2 L of serum-free conditioned medium was collected per antibody over 5 days from 4 Triple Flasks 500 cm2 (Thermo Scientific) of hybridomas cultured in Hybridoma Serum Free Media (Invitrogen) supplemented with penicillin-streptomycin. Medium was filtered through a 0.45 µm filter prior to purification.

Heavy and light chain antibody constructs for human antibodies 3.6 and 3.9, as well as a recombinant version of the previously described mouse antibody 19.2.1 were used to express antibody in the Expi293 antibody expression system (Life technologies) essentially according to the manufacturer's instructions. Between 30-200 ml of Expi293 medium was collected per antibody and was filtered through a 0.45 µm filter prior to purification.

Antibodies were purified by affinity chromatography using a 1 ml column of Protein A Sepharose HiTrap MabSelect Xtra (28-4082-58, GE Healthcare, Aus). The Protein A column was equilibrated with buffer containing 137 mM NaCl, 2 mM KCl, 10 mM phosphate buffer, pH7.4, and the antibodies were eluted with 0.1 M Glycine/HCl pH 3.0, followed by neutralization with 1 M Tris/HCl pH 9.0. The neutralized eluate was concentrated and the buffer was exchanged with PBS using a vivaspin 20 column (VS2021, Sartorius, Aus). Endotoxin levels were tested using Charles River PTS system according to manufacturer's instructions. Endotoxin levels of all final antibody preparations used for in vivo experiments was determined to be below the level of detection of the assay (less than 0.05 EU/mg of antibody). ITEM1 was purchased from Biolegend.

xiii) Assessment of anti-Fn14 Human Antibodies in Mouse Cachexia Model

Antibody efficacy was assessed in an in vivo cancer-cachexia model comprising human Fn14 expressed in mouse embryonic fibroblast cells transformed with H-Ras V12 oncogene (Johnston et al., 2015). Wildtype C57BL/6 mice were inoculated subcutaneously with tumor cells in the flank and treated ±antibody (10 mg/kg) on day 6. Mouse body weight and health state were monitored daily.

RESULTS

Example 1: Isolation of hFab Clones Specific for hFn14-Fc and hFn14-His

Human Fabs were selected from the phage display library by multiple rounds of panning in solution using magnetic beads to capture the Fc-tag of Fn14-Fc for five rounds, followed by two rounds coating Fn14-His to microtiter plates. Both tagged antigens were used in the selection process to ensure hFabs were reactive with both forms of Fn14 antigen. To bias selection towards hFabs with high affinity the stringency of washing was increased with successive rounds of panning. An increased number of bound phage was detected after the fourth round of panning with further increases in subsequent rounds (FIG. 1).

Example 2: Identification of Monoclonal hFabs Specific for hFn14-Fc and hFn14-His Single clones from round 6 and 7 were found to be highly reactive to both Fn14-Fc and Fn14-His by ELISA and did not react with an irrelevant Fc-tagged antigen. Primarily $V_H$ sequencing was performed to identify clones from rounds 5-7 with different sequences (FIG. 2). Individual clones in FIGS. 2 and 3 were analysed for binding to Fn14-His, Fn14-Fc and an irrelevant antigen and the data clearly revealed that some clones had significant binding to Fn14-His.

Example 3: Analysis of Blone hFab 6.5

Figure 4:
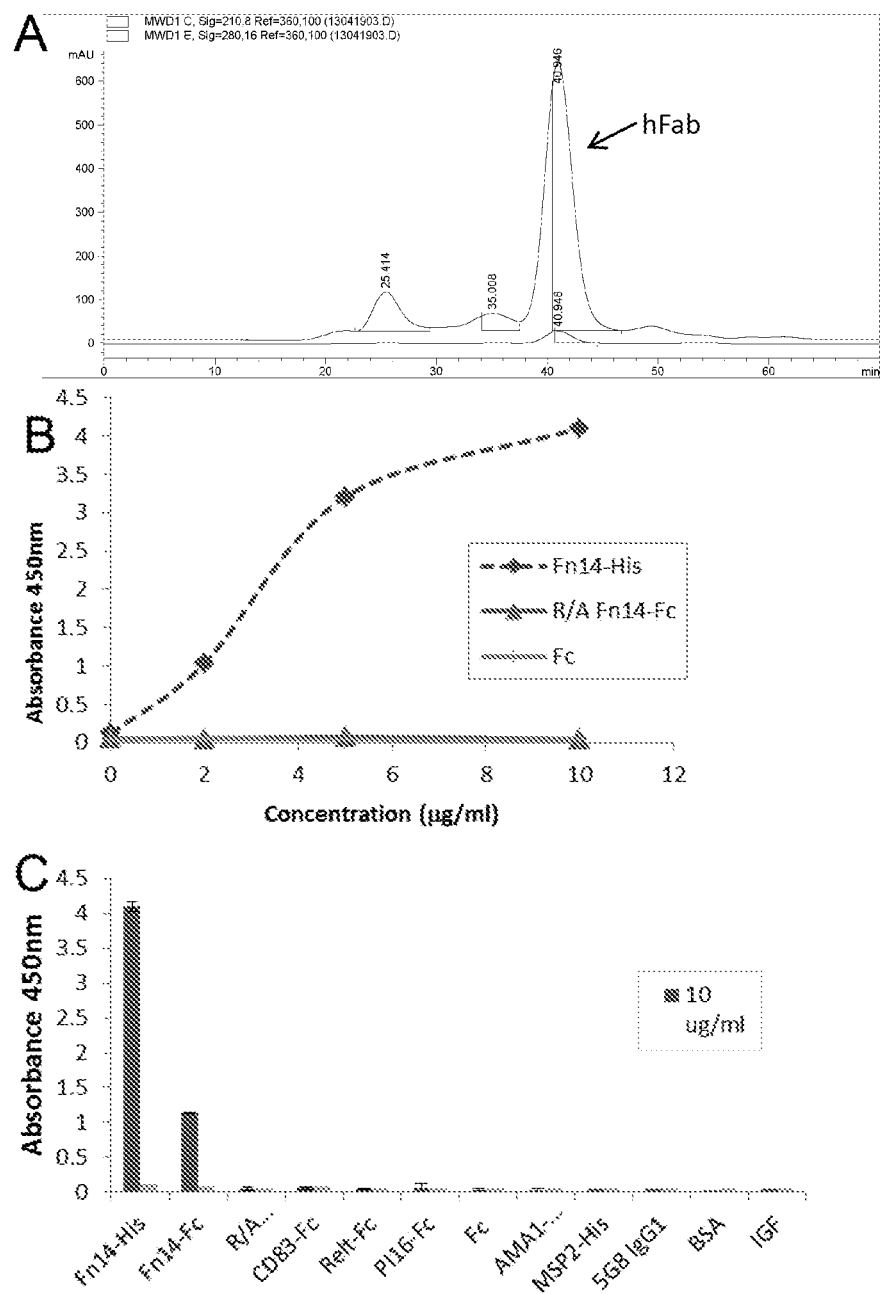
FIG. 4: Purification and characterization of hFab 6.5. (A) The hFab was purified using Ni-NTA chromatography. The eluted 250 mM fractions were further purified by S-200 gel filtration. The FPLC trace is shown. Purified hFab* is shown by an arrow. (B) The Fab clone was expressed in E. coli and purified using Ni-NTA chromatography from the periplasmic fraction. The clone binds specifically to hFn14 ectodomain (Fc and His tagged) and does not recognise the reduced and alkylated form of the antigen (R/A) indicating it has a conformational epitope. (C) The clone binds specifically to Fn14 and does react non-specifically to 9 other antigens analysed.

Clone 6.5 was sub-cloned into the *E. coli* expression vector pGC to remove the phage framework and allow the expression and purification of soluble hFab. The $V_H$ and $V_L$ chains folded correctly to form a whole Fab determined by the approximate molecular weight of 48 kDa with SDS-PAGE. Other bands on the SDS-PAGE gel were bacterial proteins in the periplasmic fraction and some free $V_L/V_H$ chains at 28 kDa. To further purify the hFab gel filtration was performed, fractions were re-analysed by SDS-PAGE and the purified hFab pooled and concentrated the final purified material shown in FIG. 4. SDS-PAGE and Western blot analysis confirmed the identity of the hFab by detecting the kappa light chain at the expected hFab molecular weight 48 kDa using an anti-human kappa antibody conjugated to HRP. The reactivity of purified hFab 6.5 to Fn14 was analysed by ELISA. Dilutions of the hFab were allowed to react with Fn14-His and the binding curve is shown in FIG. 4B. There was little reactivity to the Fc tag alone and the reduced and alkylated antigen indicating hFab 6.5 is reactive with a conformational epitope. To further analyse the specificity of hFab 6.5 an ELISA was performed (FIG. 4C), the binding data proves that hFab 6.5 is highly specific binding only to Fn14-Fc and Fn14-His and is not reactive with the other control antigens.

Example 4: Affinity Maturation of Clone hFab 6.5

Figure 5:
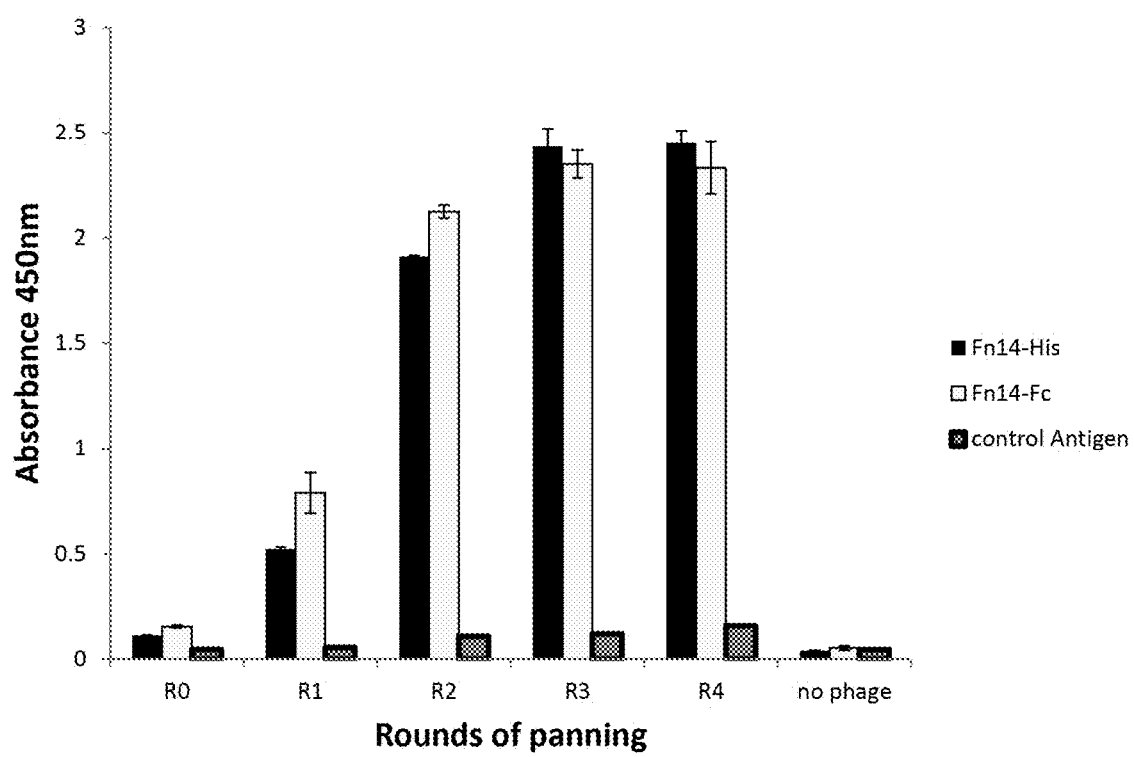
FIG. 5: (A) Isolation of higher affinity clones by light chain shuffling. Four rounds of selection were performed on Fn14 antigen with stringent washing to select higher affinity light chain partners to 6.5 $V_H$. Enrichment in the binding to Fn14 was observed after 2 rounds of panning with further increases in binding in round 3 and 4 determined by ELISA. Analysis was performed in duplicate, error bars indicate ranges of individual values.
Figure 6:
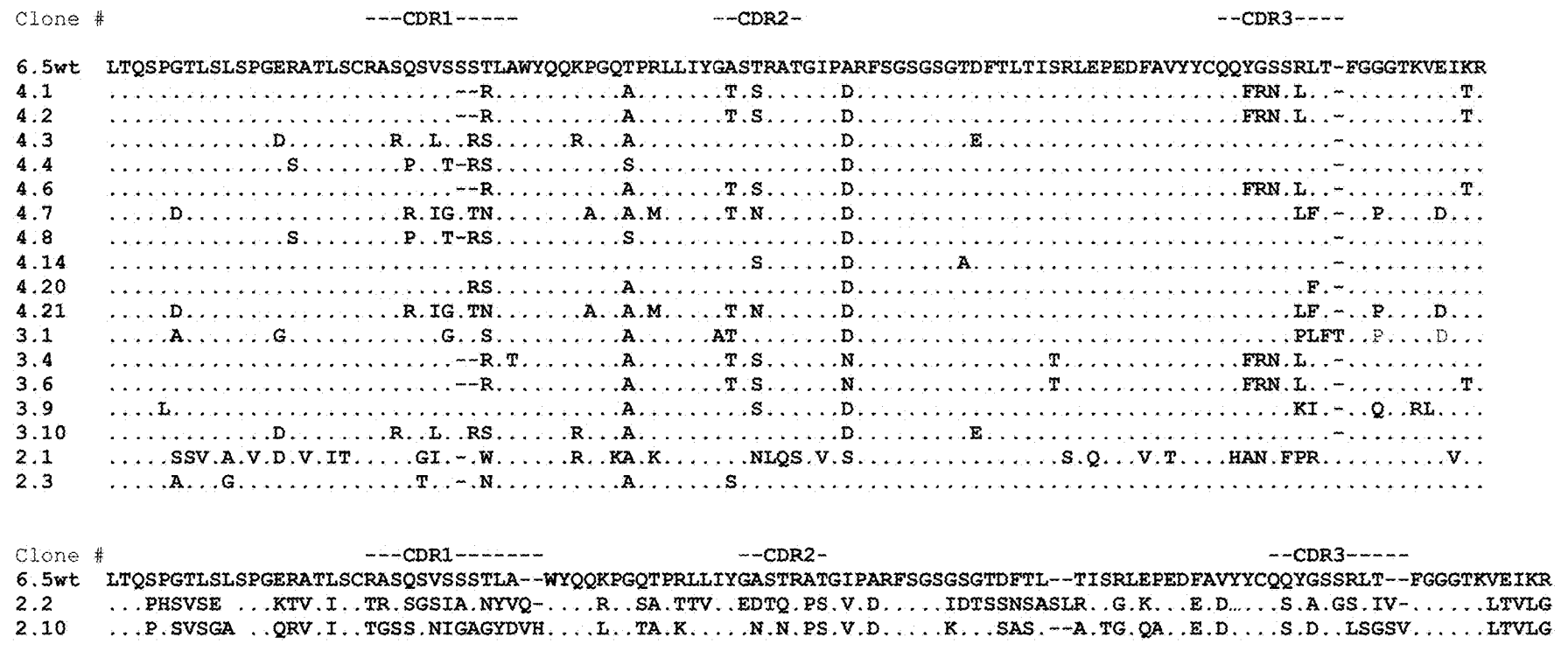

Titration of the light chain shuffled library resulted in a final library size of $>1\times10^7$ which is an acceptable size for affinity maturation. The library was expanded to $10^{13}$/ml for panning and 4 rounds of selection on Fn14 were performed to isolate higher affinity clones. Phages from rounds 2-4 reacted strongly to Fn14-Fc and Fn14-His by ELISA (FIG. 5) with no reactivity to a control antigen. Individual clones from rounds 2-4 were DNA sequenced and assessed by ELISA. Not all clones showed higher relative binding when compared directly to the native clone. When comparing the sequences (FIG. 6) of the shuffled light chains it was found that clones in round 2 had more mutations than clones in round 3 and 4. The binding of affinity matured mutants and wildtype 6.5 Fab periplasmic extracts to Fn14-Fc using similar concentrations of Fab was assessed. A dilution series for each periplasmic extract was analysed for binding to Fn14-Fc by ELISA at equivalent concentrations as detected via the Myc tag at the C-terminus of the Fabs binding to the anti-Myc antibody 9E10. Some clones showed superior binding to Fn14-Fc when compared to the other mutants and wildtype 6.5.

Binding of periplasmic extracts of wildtype 6.5 and affinity matured mutants to Fn14-Fc by ELISA at approximately the same level detected via the Myc-tag at the C-terminus of the Fab binding to the anti-Myc antibody 9E10. Some purified mutants show superior binding to Fn14-Fc by ELISA when compared with the wildtype Fab 6.5. Some of the hFab binders were expressed and purified to high purity using Ni-NTA affinity and gel filtration chromatography as described for the wildtype 6.5 clone for accurate affinity measurement using surface plasmon resonance (SPR).

The light chain shuffling process for affinity maturation was successful as the affinity constants as some mutant clones were shown to be approximately 40-fold higher than for the wildtype non-matured Fab 6.5. Some affinity clone Fabs were reformatted for in vitro experiments. Analyses used for affinity constant determinations had Chi2 level <3 and residual levels <5 indicating a good fit of the data to the Langmuir model. Based on average values are from 5 measurements in 4 different experiments, the affinity constants for wild type 6.5 are $0.94\times10^5$ $k_{on}$ or ka ($M^{-1}$ $s^{-1}$); $2.073\times10^{-3}$ $k_{off}$ or kd ($s^{-1}$); $2.205\times10^{-8}$ $K_D$ (M); 220 nM Affinity (nM). Affinity constants for a subset of light chain shuffled mutants were determined to be: between $1.503\times10^5$ $k_{on}$ or ka ($M^{-1}$ $s^{-1}$) and $1.685\times10^5$ $k_{on}$ or ka ($M^{-1}$ $s^{-1}$); between $8.158\times10^{-4}$ $k_{off}$ or kd ($s^{-1}$) and $9.785\times10^{-4}$ $k_{off}$ or kd ($s^{-1}$); and between $5.43\times10^{-9}$ $K_D$ (M) or 5.42 nM Affinity (nM) and $5.91\times10^{-9}$ $K_D$ (M); 5.91 nM Affinity (nM).

Example 5: Analysis of Antibody Binding to Human Fn14 R58A Mutant

Figure 7:
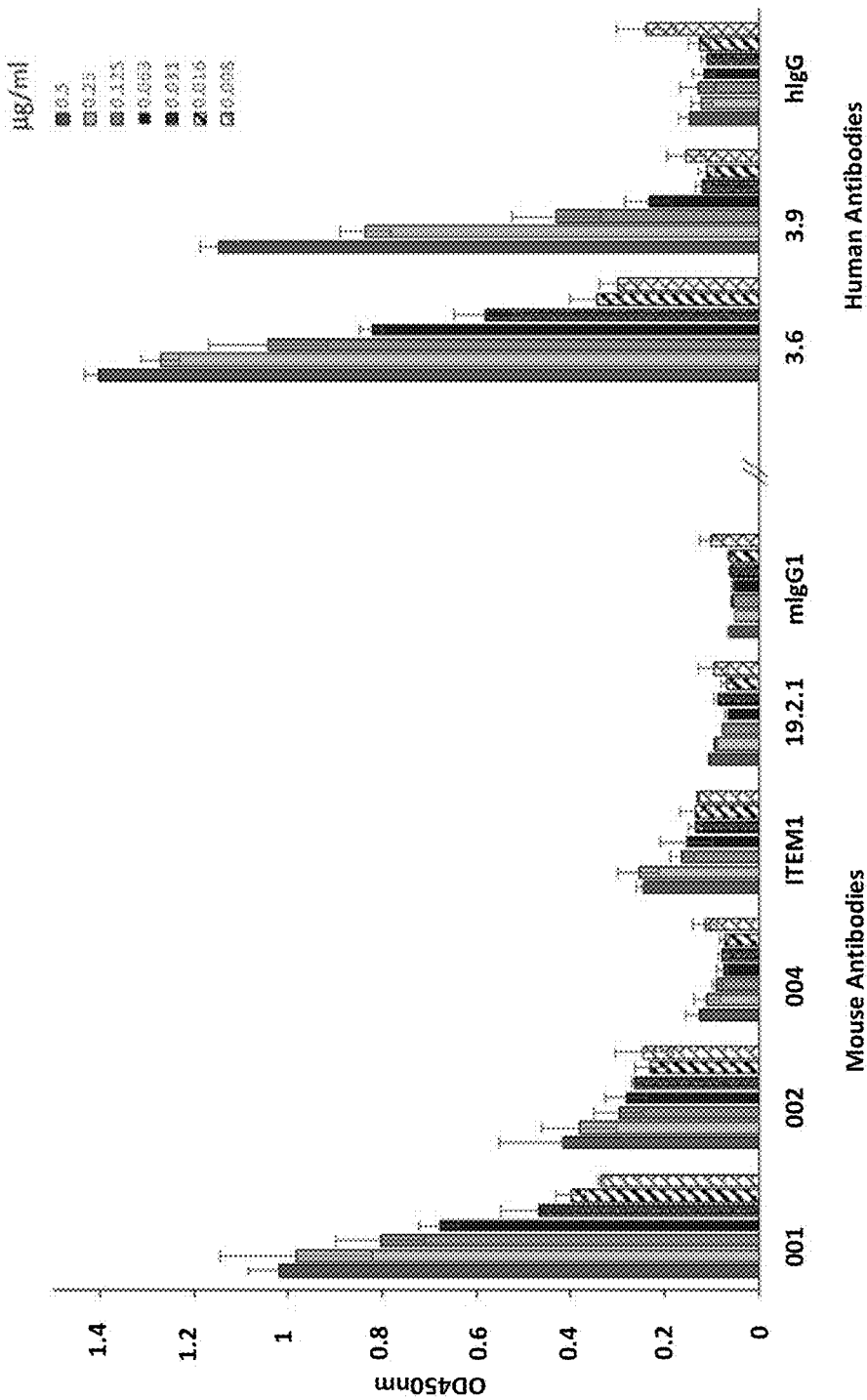
FIG. 7: is a graphical representation showing binding of anti-Fn14 mAbs to purified hFn14 mutant R58A. Results of ELISA showing the reactivity of anti-Fn14 antibodies to purified hFn14 mutant R58A are depicted. Optical density at 450 nm. Antibody concentration in μg/ml. Double forward slash (//) separates samples where different secondary antibody detection reagent was used.

Binding of the human antibodies to recombinant purified human Fn14 extracellular domain mutant R58A was assessed at a range of antibody concentrations (FIG. 7) to determine if binding was dependant on residue R58. As expected, mouse monoclonal antibodies 001 and 002 which have been previously described (Johnston et al., 2015) bind to the human Fn14 R58A mutant whereas antibodies 004, ITEM1, 19.2.1 or a mouse IgG1 control do not bind. Human antibodies 3.6 and 3.9 demonstrate efficient binding to recombinant hFn14 R58A mutant.

Example 6: Antibody Treatment of hFn14 Cachexia-Inducing Tumors

Figure 8A:
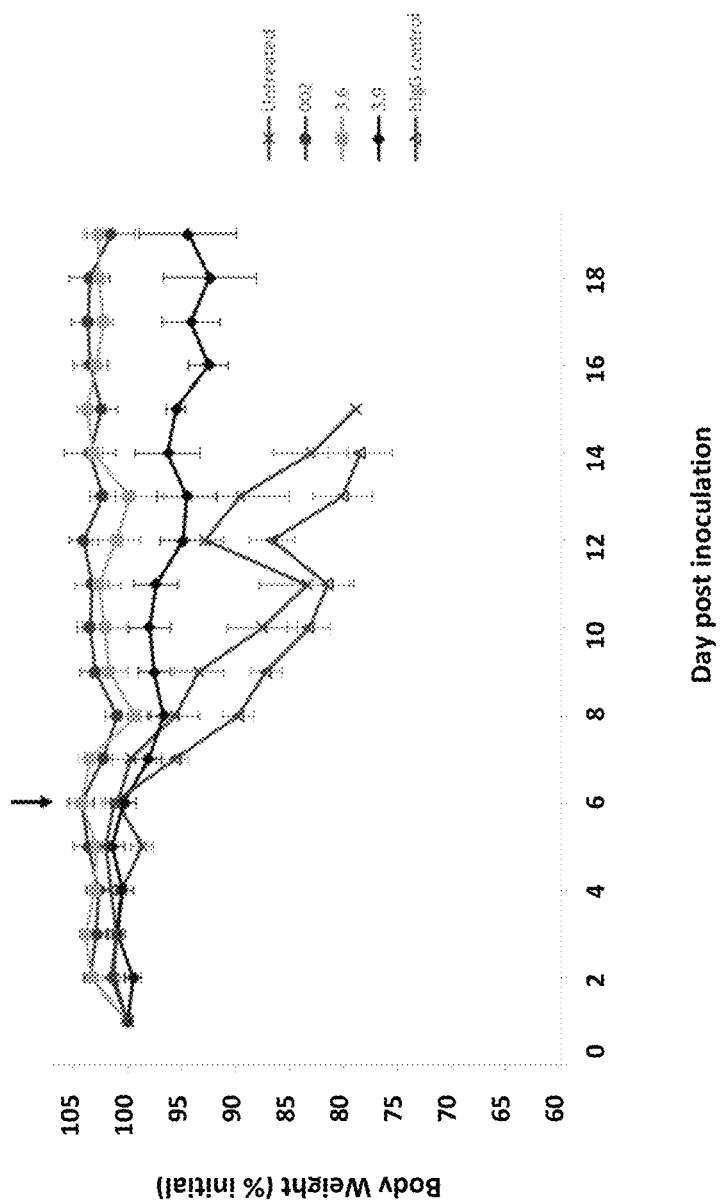
FIG. 8A is a graphical representation showing group average body weight of mice having Fn14 expressing tumours treated with human antibodies 3.6 and 3.9. Female C57BL/6 mice were injected with Fn14 tumour cells on day 1. On day 6, mice (n=8) were given a single IP injection of purified antibody (10 mg/kg) or no treatment. Body weight is depicted as % of initial weight. Antibody treatment=1. Error bars represent±SEM.
Figure 8B:
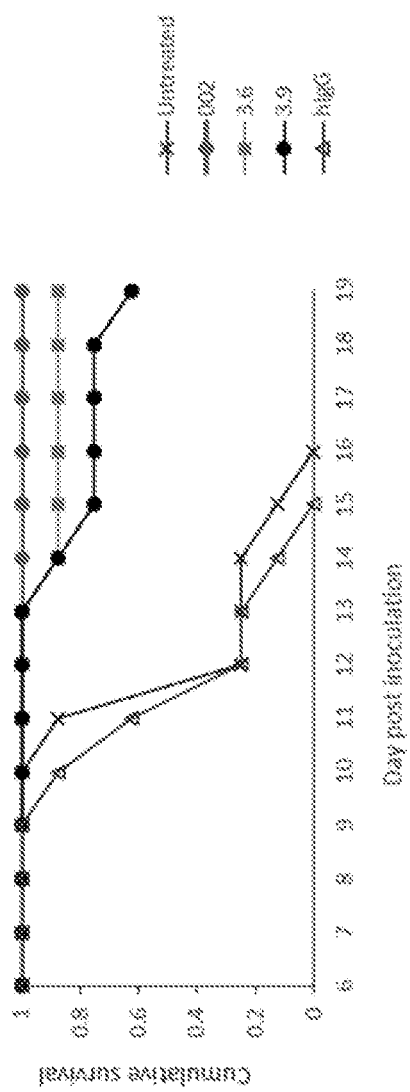
FIG. 8B is a graphical representation showing survival of mice having Fn14 expressing tumours treated with human antibodies 3.6 and 3.9. Female C57BL/6 mice were injected with Fn14 tumour cells on day 1. On day 6, mice (n=8) were given a single IP injection of purified antibody (10 mg/kg) or no treatment. Survival is depicted as a Kaplan-Meier curve.

The ability of the human antibodies 3.6 and 3.9 to block cachexia was assessed in the human Fn14 MEF tumor model previously described (Johnston et al., 2015). Mice were inoculated with Fn14 expressing tumor cells on day 1 and body weight and overall health of mice was assessed daily. Mice were treated with antibodies on day 6 (10 mg/kg). Onset of weight loss in this model occurs on average on day 8. Control mice received no treatment and as expected exhibited weight loss from day 8. Antibody 002 has previously been shown to efficiently block cachexia in this model and increase survival. Fn14 tumor-bearing mice that received antibody treatment with human antibodies 3.6 or 3.9 maintained body weight and displayed increased survival. These data clearly demonstrate the anti-cachectic ability of human antibodies 3.6 and 3.9 (FIG. 8).

The ability of other Fn14 antibodies to block cachexia was also assessed and where 001 and 002 clearly show anti-cachectic ability, antibodies 004, ITEM1 and 19.2.1 do not block the loss of body mass, nor do they increase survival. These data demonstrate that not all antibodies targeting Fn14 have the ability to block cachexia.

REFERENCES

Al-Lazikani et al., *J Mol Biol* 273: 927-948, 1997;
Ausubel et al., (editors), Current Protocols in Molecular Biology, Greene Pub. Associates and Wiley-Interscience (1988, including all updates until present);
Brinkmann et al., *Proc. Natl. Acad. Sci. USA,* 90: 7538-7542, 1993;
Coia et al., *J. Immunol. Meth.,* 192: 13-23, 1996;
Coligan et al., (editors) Current Protocols in Immunology, John Wiley & Sons (including all updates until present);
Bork et al., *J Mol. Biol.* 242: 309-320, 1994;
Chothia and Lesk, *J. Mol Biol.* 196: 901-917, 1987;
Chothia et al., *Nature* 342: 877-883, 1989;
Dharmapatni et al., *Arthritis Res Ther,* 13: R51, 2011;
Frauenknecht et al., *J Neuroimmunol,* 227: 1-9, 2010;
Gefter et al, *Somatic Cell Genet.,* 3: 231-236, 1977;
Giudicelli et al., *Nucleic Acids Res.,* 25: 206-211 1997
Glover and Hames (editors), DNA Cloning: A Practical Approach, Volumes 1-4, IRL Press (1995 and 1996);
Goodman et al., Goodman and Gilman's The Pharmacological Basis of Therapeutics, 8th Ed., Macmillan Publishing Co., 1990;
Guan et al., *Proc. Natl. Acad. Sci. USA* 95: 13206-13210, 1998;
Brown (editor), Essential Molecular Biology: A Practical Approach, Volumes 1 and 2, IRL Press (1991);
de Haard et al., *J. Biol Chem,* 182: 172-184, 1999;
Harlow and Lane (editors) Antibodies: A Laboratory Manual, Cold Spring Harbor Laboratory, (1988);
Honnegher and Plückthun, *J. Mol. Biol.,* 309: 657-670, 2001;
Johnston et al., *Cell,* 162: 1365-1378, 2015;
Kabat *Sequences of Proteins of Immunological Interest,* National Institutes of Health, Bethesda, Md., 1987 and 1991;
Kohler and Milstein, *Nature,* 256: 495-497, 1975;
Kohler and Milstein, *Eur. J. Immunol.* 6: 511-519, 1976;
Kumar et al, *Immuno. Letters,* 65: 153-159, 1999;
Marks et al., *Nature Biotechnology,* 10: 779-783, 1992;
Natsume et al., *Cancer Res.,* 68: 3863-3872, 2008;
Perbal, A Practical Guide to Molecular Cloning, John Wiley and Sons (1984);
Plückthun in The Pharmacology of Monoclonal Antibodies, vol. 113, Rosenburg and Moore eds., Springer Verlag, New York, pp. 269-315, 1994;
Sambrook et al., Molecular Cloning: A Laboratory Manual, Cold Spring Harbour Laboratory Press (1989);
Scopes In: Protein purification: principles and practice, Third Edition, Springer Verlag, 1994;
Sakaguchi et al, *Nature* 426: 454-460, 1995
Shalaby et al, *J. Exp. Med.,* 175: 217-225, 1992;
Trenado et al., *J. Clin. Invest.,* 112: 1688-1696, 2002;
Vince et al., *J. Cell. Biol,* 182: 172-184, 2008;
Yumane-Ohnuki et al., *Biotechnol Bioeng.* 87: 614-22, 2004;
Zhao et al., *J Immunol,* 179: 7949-7958, 2007; and
Zola, "Monoclonal Antibodies: A Manual of Techniques", CRC Press, 1987.

The invention claimed is:

1. An isolated or recombinant Fn14-binding protein comprising an antigen binding domain, wherein the antigen binding domain binds specifically to Fn14 or a cell expressing Fn14, and wherein the antigen binding domain comprises:
   i) a heavy chain variable region ($V_H$) comprising CDRs 1, 2 and 3 in the sequence set forth in SEQ ID NO:9; and
   ii) a light chain variable region ($V_L$) comprising CDRs 1, 2 and 3 in the sequence set forth in any one of SEQ ID NOs: 24, 30 to 48 or 70 to 75.

2. The Fn14-binding protein of claim 1, wherein the Fn14-binding protein when tested as a Fab binds to Fn14 with a $K_D$ of between 5 and 220 nM and/or wherein the Fn14-binding protein when tested as a Fab binds to Fn14 with a Kd of between $8 \times 10^{-4} s^{-1}$ to $2.1 \times 10^{-3} s^{-1}$.

3. The Fn14-binding protein of claim 1, wherein the antigen binding domain comprises:
   i) a $V_H$ comprising a sequence set forth in SEQ ID NO:9 and a $V_L$ comprising a sequence set forth in SEQ ID NO:24;
   ii) a $V_H$ comprising a sequence set forth in SEQ ID NO:9 and a $V_L$ comprising a sequence set forth in SEQ ID NO:30;
   iii) a $V_H$ comprising a sequence set forth in SEQ ID NO:9 and a $V_L$ comprising a sequence set forth in SEQ ID NO:31;
   iv) a $V_H$ comprising a sequence set forth in SEQ ID NO:9 and a $V_L$ comprising a sequence set forth in SEQ ID NO:32;
   v) a $V_H$ comprising a sequence set forth in SEQ ID NO:9 and a $V_L$ comprising a sequence set forth in SEQ ID NO:33;
   vi) a $V_H$ comprising a sequence set forth in SEQ ID NO:9 and a $V_L$ comprising a sequence set forth in SEQ ID NO:34;
   vii) a $V_H$ comprising a sequence set forth in SEQ ID NO:9 and a $V_L$ comprising a sequence set forth in SEQ ID NO:35;
   viii) a $V_H$ comprising a sequence set forth in SEQ ID NO:9 and a $V_L$ comprising a sequence set forth in SEQ ID NO:36;
   ix) a $V_H$ comprising a sequence set forth in SEQ ID NO:9 and a $V_L$ comprising a sequence set forth in SEQ ID NO:37;
   x) a $V_H$ comprising a sequence set forth in SEQ ID NO:9 and a $V_L$ comprising a sequence set forth in SEQ ID NO:38;
   xi) a $V_H$ comprising a sequence set forth in SEQ ID NO:9 and a $V_L$ comprising a sequence set forth in SEQ ID NO:39;
   xii) a $V_H$ comprising a sequence set forth in SEQ ID NO:9 and a $V_L$ comprising a sequence set forth in SEQ ID NO:40;
   xiii) a $V_H$ comprising a sequence set forth in SEQ ID NO:9 and a $V_L$ comprising a sequence set forth in SEQ ID NO:41;
   xiv) a $V_H$ comprising a sequence set forth in SEQ ID NO:9 and a $V_L$ comprising a sequence set forth in SEQ ID NO:42;
   xv) a $V_H$ comprising a sequence set forth in SEQ ID NO:9 and a $V_L$ comprising a sequence set forth in SEQ ID NO:43;
   xvi) a $V_H$ comprising a sequence set forth in SEQ ID NO:9 and a $V_L$ comprising a sequence set forth in SEQ ID NO:44;
   xvii) a $V_H$ comprising a sequence set forth in SEQ ID NO:9 and a $V_L$ comprising a sequence set forth in SEQ ID NO:45;
   xviii) a $V_H$ comprising a sequence set forth in SEQ ID NO:9 and a $V_L$ comprising a sequence set forth in SEQ ID NO:46;
   xix) a $V_H$ comprising a sequence set forth in SEQ ID NO:9 and a $V_L$ comprising a sequence set forth in SEQ ID NO:47;
   xx) a $V_H$ comprising a sequence set forth in SEQ ID NO:9 and a $V_L$ comprising a sequence set forth in SEQ ID NO:48;
   xxi) a $V_H$ comprising a sequence set forth in SEQ ID NO:9 and a $V_L$ comprising a sequence set forth in SEQ ID NO:70;
   xxii) a $V_H$ comprising a sequence set forth in SEQ ID NO:9 and a $V_L$ comprising a sequence set forth in SEQ ID NO:71;
   xxiii) a $V_H$ comprising a sequence set forth in SEQ ID NO:9 and a $V_L$ comprising a sequence set forth in SEQ ID NO:72;
   xxiv) a $V_H$ comprising a sequence set forth in SEQ ID NO:9 and a $V_L$ comprising a sequence set forth in SEQ ID NO:73;
   xxv) a $V_H$ comprising a sequence set forth in SEQ ID NO:9 and a $V_L$ comprising a sequence set forth in SEQ ID NO:74; or
   xxvi) a $V_H$ comprising a sequence set forth in SEQ ID NO:9 and a $V_L$ comprising a sequence set forth in SEQ ID NO:75.

4. The Fn14-binding protein of claim 1, (1) wherein the $V_H$ and the $V_L$ are in a single polypeptide chain and the Fn14-Binding protein is:
   a) a single chain Fv fragment (scFv);
   b) a dimeric scFv (di-scFV);
   c) at least one of a) and/or b) linked to a heavy chain constant region or an Fc or a heavy chain constant domain ($C_H$) 2 and/or $C_H$3; or
   d) at least one of a) and/or b) linked to a protein that binds to an immune effector cell; or
(2) wherein the $V_L$ and $V_H$ are in separate polypeptide chains and the Fn14-binding protein is:
   i) a diabody;
   ii) a triabody;
   iii) a tetrabody;
   iv) a Fab;
   v) a F(ab')2;
   vi) a Fv;
   vii) at least one of i) to vi) linked to a heavy chain constant region or an Fc or a heavy chain constant domain ($C_H$)2 and/or $C_H$3;
   viii) at least one of i) to vi) linked to a protein that binds to an immune effector cell;
   ix) an antibody;
   x) comprises an IgG1 constant region or an IgG4 constant region or a stabilized IgG4 constant region.

5. The Fn14-binding protein of claim 1, which is an antibody, wherein the antibody comprises any one of the following:
   i) a $V_H$ comprising a sequence set forth in SEQ ID NO:9 and a $V_L$ comprising a sequence set forth in SEQ ID NO:24;
   ii) a $V_H$ comprising a sequence set forth in SEQ ID NO:9 and a $V_L$ comprising a sequence set forth in SEQ ID NO:30;

iii) a $V_H$ comprising a sequence set forth in SEQ ID NO:9 and a $V_L$ comprising a sequence set forth in SEQ ID NO:31;
iv) a $V_H$ comprising a sequence set forth in SEQ ID NO:9 and a $V_L$ comprising a sequence set forth in SEQ ID NO:32;
v) a $V_H$ comprising a sequence set forth in SEQ ID NO:9 and a $V_L$ comprising a sequence set forth in SEQ ID NO:33;
vi) a $V_H$ comprising a sequence set forth in SEQ ID NO:9 and a $V_L$ comprising a sequence set forth in SEQ ID NO:34;
vii) a $V_H$ comprising a sequence set forth in SEQ ID NO:9 and a $V_L$ comprising a sequence set forth in SEQ ID NO:35;
viii) a $V_H$ comprising a sequence set forth in SEQ ID NO:9 and a $V_L$ comprising a sequence set forth in SEQ ID NO:36;
ix) a $V_H$ comprising a sequence set forth in SEQ ID NO:9 and a $V_L$ comprising a sequence set forth in SEQ ID NO:37;
x) a $V_H$ comprising a sequence set forth in SEQ ID NO:9 and a $V_L$ comprising a sequence set forth in SEQ ID NO:38;
xi) a $V_H$ comprising a sequence set forth in SEQ ID NO:9 and a $V_L$ comprising a sequence set forth in SEQ ID NO:39;
xii) a $V_H$ comprising a sequence set forth in SEQ ID NO:9 and a $V_L$ comprising a sequence set forth in SEQ ID NO:40;
xiii) a $V_H$ comprising a sequence set forth in SEQ ID NO:9 and a $V_L$ comprising a sequence set forth in SEQ ID NO:41;
xiv) a $V_H$ comprising a sequence set forth in SEQ ID NO:9 and a VI, comprising a sequence set forth in SEQ ID NO:42;
xv) a $V_H$ comprising a sequence set forth in SEQ ID NO:9 and a $V_L$ comprising a sequence set forth in SEQ ID NO:43;
xvi) a $V_H$ comprising a sequence set forth in SEQ ID NO:9 and a $V_L$ comprising a sequence set forth in SEQ ID NO:44;
xvii) a $V_H$ comprising a sequence set forth in SEQ ID NO:9 and a $V_L$ comprising a sequence set forth in SEQ ID NO:45;
xviii) a $V_H$ comprising a sequence set forth in SEQ ID NO:9 and a $V_L$ comprising a sequence set forth in SEQ ID NO:46;
xix) a $V_H$ comprising a sequence set forth in SEQ ID NO:9 and a $V_L$ comprising a sequence set forth in SEQ ID NO:47;
xx) a $V_H$ comprising a sequence set forth in SEQ ID NO:9 and a $V_L$ comprising a sequence set forth in SEQ ID NO:48;
xxi) a $V_H$ comprising a sequence set forth in SEQ ID NO:9 and a $V_L$ comprising a sequence set forth in SEQ ID NO:70;
xxii) a $V_H$ comprising a sequence set forth in SEQ ID NO:9 and a $V_L$ comprising a sequence set forth in SEQ ID NO:71;
xxiii) a $V_H$ comprising a sequence set forth in SEQ ID NO:9 and a $V_L$ comprising a sequence set forth in SEQ ID NO:72;
xxiv) a $V_H$ comprising a sequence set forth in SEQ ID NO:9 and a $V_L$ comprising a sequence set forth in SEQ ID NO:73;
xxv) a $V_H$ comprising a sequence set forth in SEQ ID NO:9 and a $V_L$, comprising a sequence set forth in SEQ ID NO:74;
xxvi) a $V_H$ comprising a sequence set forth in SEQ ID NO:9 and a $V_L$ comprising a sequence set forth in SEQ ID NO:75.

6. A composition comprising the Fn14-binding protein of claim 1 and a suitable carrier.

7. A method for inhibiting Fn14-signaling in a subject, the method comprising administering to a subject the Fn14-binding protein of claim 1, or the composition of claim 6.

8. The method of claim 7, wherein the subject has a condition selected from: cancer, metastasis, excessive vascularization or angiogenesis, an autoimmune disease, an inflammatory disease, a neurodegenerative disease, a wasting disorder, a cardiovascular disease or ischemia.

9. The method of claim 8, wherein the condition is cancer.

10. The method of claim 8, wherein the wasting disorder is cachexia.

* * * * *